US010677782B2

(12) United States Patent
Wei

(10) Patent No.: US 10,677,782 B2
(45) Date of Patent: Jun. 9, 2020

(54) METHODS OF DETERMINING INTERFERON HAVING DIRECT INHIBITORY EFFECTS ON TUMORS AND USES THEREOF

(71) Applicants: Guangwen Wei, Chengdu (CN); SUPERLAB FAR EAST LIMITED, Tortola (VG)

(72) Inventor: Guangwen Wei, Chengdu (CN)

(73) Assignee: SUPERLAB FAR EAST LIMITED, Tortola (VG)

( * ) Notice: Subject to any disclaimer, the term of this patent is extended or adjusted under 35 U.S.C. 154(b) by 159 days.

(21) Appl. No.: 15/035,749

(22) PCT Filed: Nov. 12, 2014

(86) PCT No.: PCT/CN2014/090859
§ 371 (c)(1),
(2) Date: May 10, 2016

(87) PCT Pub. No.: WO2015/070751
PCT Pub. Date: May 21, 2015

(65) Prior Publication Data
US 2016/0258930 A1    Sep. 8, 2016

Related U.S. Application Data

(60) Provisional application No. 61/903,937, filed on Nov. 13, 2013.

(51) Int. Cl.
| | |
|---|---|
| *G01N 33/50* | (2006.01) |
| *G01N 33/68* | (2006.01) |
| *C12Q 1/6886* | (2018.01) |
| *A61K 38/00* | (2006.01) |
| *C07K 14/56* | (2006.01) |

(52) U.S. Cl.
CPC .......... *G01N 33/5011* (2013.01); *C07K 14/56* (2013.01); *C12Q 1/6886* (2013.01); *G01N 33/6866* (2013.01); *A61K 38/00* (2013.01); *C12Q 2600/136* (2013.01); *C12Q 2600/158* (2013.01)

(58) Field of Classification Search
CPC ............ C12Q 1/6886; C12Q 2600/158; C12Q 2600/136; A61K 38/00; C07K 14/56; G01N 33/5011; G01N 33/6866
See application file for complete search history.

(56) References Cited

U.S. PATENT DOCUMENTS

2009/0053147 A1*  2/2009 Gantier ............... C07K 14/475
                                                      424/45
2013/0273527 A1   10/2013 Wei et al.

OTHER PUBLICATIONS

Thompson MD et al. "Pegylated interferon alpha targets Wht signalling by inducing nuclear export of beta-catenin" Journal of Hepatology, 2010, 54(3): 506-512.
Feb. 6, 2015 PCT Written Opinion for PCT/CN2014/090859, filed Nov. 12, 2014.
Feb. 6, 2015 PCT International Search Report for PCT/CN2014/090859, filed Nov. 12, 2014.
Li HL, "The treatment of super interferon alpha on non-small cell lung cancer", Sep. 15, 2011, Chinese Master's Theses Full-text Database Medicine and Health Science, No. 9, p. 26-27.
European Office Action, dated May 7, 2018, Application No. 14861341 for Superlab Far East Limited.
European Search Report, dated Sep. 8, 2017, Application No. 14861341 for Superlab Far East Limited.
Australian Office Action, dated Jul. 12, 2018, Application No. 2014350714 for Superlab Far East Limited.
Japanese Office Action, dated Aug. 14, 2018, Application No. 2016-531672 for Superlab Far East Limited.
Nakajima, Terumi et al. New basic biochemistry laboratory procedure 6 with restriction of measuring method using biological activity. Japan, Apr. 30, 1988, pp. 192-196.
Li Wei et al. Comparison of the regulation of β-catenin signaling by type I, type II and type III interferons in hepatocellular carcinoma cells. PLoS One. 2012;7(10):e47040.

* cited by examiner

*Primary Examiner* — Joanne Hama
*Assistant Examiner* — Bruce D. Hissong
(74) *Attorney, Agent, or Firm* — Law Offices of Albert Wai-Kit Chan, PLLC

(57) ABSTRACT

The invention provides novel methods of determining or comparing potency of a test interferon relative to rSIFN-co (an interferon having therapeutic effects on solid tumors); methods of establishing substantial equivalence between a test interferon and rSIFN-co; methods for down-regulation of expression of Wnt-related receptors or co-receptors, such as LRP6/FZD6; down-regulation of expression of Wnt-related target genes, such as, Axin2, CD24, Survivin and/or ID2; inhibition of beta-catenin/TCF transcriptional activities; suppression of expression of beta-catenin; up-regulation of tumor suppressor genes, such as DKK-3, BATF2 and/or KLF4; inhibition of tumor cell viability in vitro; inhibition of tumor growth and metastases in vivo; inhibition of tumor cell migration, pseudopod formation, and colony formation in vitro; as well as methods for determining potency of a test interferon, kits for determination of such methods, and an interferon or an interferon substitute having said activities.

11 Claims, 18 Drawing Sheets
Specification includes a Sequence Listing.

METHODS OF DETERMINING INTERFERON HAVING DIRECT INHIBITORY EFFECTS ON TUMORS AND USES THEREOF

CROSS-REFERENCE TO RELATED APPLICATIONS

This application is the National Phase of International Application No. PCT/CN2014/090859, filed Nov. 12, 2014, which claims the priority of U.S. Application No. 61/903,937, filed Nov. 13, 2013. The entire contents and disclosures of the preceding applications are hereby incorporated by reference into this application.

FIELD OF THE INVENTION

The invention herein relates to novel methods of determining potency of a test interferon relative to rSIFN-co, methods of establishing substantial equivalence between a test interferon and rSIFN-co, methods of inhibiting cancer cell migration, pseudopod formation, beta-catenin/TCF mediated transcriptional activity, and beta-catenin protein level, methods of down-regulating expression of Wnt-related receptors or co-receptors, methods of inhibiting expression of target genes of the Wnt signaling pathway, methods of up-regulating tumor suppressor genes, as well as assay kits for performance of any and all such methods. The invention also relates to interferons or interferon substitutes having said activities.

BACKGROUND OF THE INVENTION

Throughout this application, various publications are referenced. Disclosures of these publications in their entireties are hereby incorporated by reference into this application in order to more fully describe the state of the art to which this invention pertains.

Super Interferon (hereafter, "rSIFN-co" or "SIFN-I", an interferon having the therapeutic effect on solid tumors) has been described in U.S. Pat. No. 7,364,724 (Recombinant Super-Compound Interferon) and U.S. Pat. No. 7,585,647 (Nucleic Acid Encoding Recombinant Interferon), rSIFN-co is expressed from an engineered gene construct that encodes the same amino acid sequence as INFERGEN® (interferon alfacon-1), a consensus interferon alpha that was disclosed in U.S. Pat. No. 4,695,623. However, rSIFN-co is encoded by a novel nucleic acid sequence different from that encoding INFERGEN®. As compared to INFERGEN®, the rSIFN-co protein has a novel tertiary structure and has improved biological properties as well.

rSIFN-co also has a broader spectrum of biological activities as compared to INFERGEN®, including direct inhibitory effects on solid tumors as well as anti-viral activities, as described in U.S. Pat. Nos. 8,114,395, 8,287,852, and U.S. Pat. No. 8,425,896.

SUMMARY OF THE INVENTION

In view of the unique biological activities of rSIFN-co compared with other commercially available interferons and the potential of rSIFN-co for human use, it is desirable to provide for methods to assess the biological activity and/or potency of rSIFN-co and other test interferons, for example, for quality control purposes during the manufacturing process or otherwise, to ensure that the final product retains or has the desired activities and is different from the commercially available interferons. It is also desirable to provide further uses of rSIFN-co and interferons or interferon substitutes having the desired activities.

In one aspect, the present invention provides a method of determining or comparing potency of a test interferon relative to rSIFN-co or a rSIFN-co substitute comprising: (I) providing the test interferon and rSIFN-co or rSIFN-co substitute; and (2) determining any one or more of the following activities on the test interferon and rSIFN-co or rSIFN-co substitute under same specified conditions, respectively: (a) inhibition of in vivo cancer cell growth in any one or more tumor-bearing animal models; (b) Reduction in cancer cell viability; (c) Inhibition of cancer cell migration; (d) Inhibition of beta-catenin/TCF transcriptional activity in cancer cells; (e) Down-regulation of expression of LRP6 and/or FZD6 in cancer cells; (f) Inhibition of expression of any one or more of: Axin2, CD24, Survivin and ID2 in cancer cells; (g) Inhibition of pseudopod formation in cancer cells; (h) Inhibition of beta-catenin expression in cancer cells; and (i) Up-regulation of expression of any one or more of DKK-3, KLF-4, and BATF2 in cancer cells; whereby the presence in the test interferon of any 1, or 2, or 3, or 4, or 5, or 6 of the activities specified in (a), (b), (c), (d), (e), and (f), in a statistically significant manner, and/or the presence in the test interferon of any one or more of the activities specified in (g), (h) and (i), signifies that the test interferon and rSIFN-co or rSIFN-co substitute have substantially the same potency, that is, they have substantially the same effectiveness or can generate substantially the same result. For purposes herein, "substantially the same" means at least about 70% the same; optionally, at least about 80% the same; still optionally, at least about 90% the same; further optionally, at least about 95% the same.

In another aspect, the present invention provides a method of establishing substantial equivalence between a test interferon and rSIFN-co or a rSIFN-co substitute comprising: (1) providing the test interferon and rSIFN-co or rSIFN-co substitute; and (2) determining any one or more of the following activities on the test interferon and rSIFN-co or rSIFN-co substitute under same specified conditions, respectively: (a) Inhibition of in vivo cancer cell growth in any one or more tumor-bearing animal models; (b) Reduction in cancer cell viability; (c) Inhibition of cancer cell migration; (d) Inhibition of beta-catenin/TCF transcriptional activity in cancer cells; (e) Down-regulation of expression of LRP6 and/or FZD6 in cancer cells; (f) Inhibition of expression of any one or more of: Axin2, CD24, Survivin and ID2 in cancer cells; (g) inhibition of pseudopod formation in cancer cells; (h) Inhibition of beta-catenin expression in cancer cells; and (i) Up-regulation of expression of any one or more of: DKK-3, KLF-4, and BATF2 in cancer cells; whereby the presence in the test interferon of any 1, or 2, or 3, or 4, or 5, or 6 of the activities specified in (a), (b), (c), (d), (e), and (f), in a statistically significant manner, and/or the presence in the test interferon of any one or more of the activities specified in (g), (h) and (i), signifies that the test interferon and rSIFN-co or rSIFN-co substitute are substantial equivalence.

In some embodiments, the cancer cells employed in determining one or more activities comprise any one or more of: lung cancer cells, colon cancer cells, cervical cancer cells, liver cancer cells, breast cancer cells, and pancreatic cancer cells. In some embodiments, the cancer cells employed in determining one or more activities comprise any one or more of: A549 cells, Hela cells, CL-1 cells, Huh-7 cells, SW480 cells, MDA-MB-231 cells, Calu-1 cells, SMMC-7721 cells, PANC-1 cells, SW620 cells, SPC-A4 cells, H1299 cells, H460 cells, and HT-29 cells.

In some embodiments, the cancer cells employed in determining activity (a), inhibition of in vivo cancer cell growth, comprise any one or more of: liver cancer cells, cervical cancer cells, colon cancer cells, and lung cancer cells. In some embodiments, the cancer cells employed in determining activity (a) comprise any one or more of: SMMC-7721 cells, Hela cells, HT-29 cells, SPC-A4 cells, and A549 cells; optionally, comprise any one or more of: HT-29 cells, SPC-A4 cells, and A549 cells; further optionally, comprise A549 cells. In some embodiments, normal saline or PBS is used as control in determining inhibition in activity (a). In some embodiments, the test interferon and/or rSIFN-co or rSIFN-co substitute administered to a tumor-bearing animal model in determining activity (a), is administered in a range of about 0.02 mg to about 0.30 mg; optionally, about 0.05 mg to about 0.15 mg. In some embodiments, the test interferon and/or rSIFN-co or rSIFN-co substitute, administered to a tumor-bearing animal model in determining activity (a), is administered every other day. In some embodiments, the test interferon and/or rSIFN-co or rSIFN-co substitute, administered to a tumor-bearing animal model in determining activity (a), is administered for about 2 weeks to about 6 weeks; optionally, about 3 weeks to about 4 weeks.

In some embodiments, in determining activity (b), reduction in cancer cell viability, the test interferon and/or rSIFN-co or rSIFN-co substitute each causes about 50% reduction in viability of the cancer cells at a concentration in a range of between about 6.25 mcg/ml and about 25 mcg/ml; optionally, between about 10 mcg/ml and about 18 mcg/ml; more optionally, between about 10 mcg/ml and about 15 mcg/ml. In some embodiments, in determining activity (b), the test interferon and/or rSIFN-co or rSIFN-co substitute each causes reduction in cancer cell viability to a substantially undetectable level at a concentration in a range of at least about 25 mcg/ml; optionally, at least about 50 mcg/ml; further optionally, at least about 75 mcg/ml; more optionally, at least about 100 mcg/ml. In some embodiments, in determining activity (b), the concentrations of the test interferon and/or rSIFN-co or rSIFN-co substitute comprise concentrations in a range of between about 0.2 mcg/ml and about 100 mcg/ml. In some embodiments, in determining activity (b), the cancer cells are treated by the test interferon and/or rSIFN-co or rSIFN-co substitute for at least about 1 day; optionally, at least about 2 days. In some embodiments, the cancer cells employed in determining activity (b) comprise any one or more of: lung cancer cells, colon cancer cells, cervical cancer cells, liver cancer cells, breast cancer cells, and pancreatic cancer cells; optionally, comprise any one or more of lung cancer cells, colon cancer cells, liver cancer cells, breast cancer cells, and pancreatic cancer cells. In some embodiments, the cancer cells employed in determining activity (b) comprise any one or more of A549 cells, Hela cells, CL-1 cells, Huh-7 cells, SW480 cells, MDA-MB-231 cells, Calu-1 cells, SMMC-7721 cells, and PANC-1 cells; optionally comprise any one or more of: A549 cells, CL-1 cells, Huh-7 cells, SW480 cells, MDA-MB-231 cells, Calu-1 cells, SMMC-7721 cells, and PANC-1 cells.

In some embodiments, the cancer cells employed in determining activity (b) are treated by the test interferon and/or rSIFN-co or rSIFN-co substitute in a range of about 5 mcg/ml to about 20 mcg/ml; optionally, about 10 mcg/ml. In some embodiments, the cancer cells employed in determining activity (b) are treated for about 1 day to about 10 days; optionally, about 1 day to about 6 days. In some embodiments, the cancer cells employed in determining activity (b) comprise any one or more of lung cancer cells and colon cancer cells. In some embodiments, the cancer cells employed in determining activity (b) comprise any one or more of: A549 cells and SW620 cells.

In some embodiments, the cancer cells employed in determining activity (c), inhibition of cancer cell migration, comprise any one or more of: lung cancer cells, and colon cancer cells. In some embodiments, the cancer cells employed in determining activity (c) comprise any one or more of: A549 cells, and SW620 cells. In some embodiments, the inhibition of cancer cell migration in activity (c) is determined using Transwell method. In some embodiments, the cancer cells employed in determining activity (c) are treated by the test interferon and/or rSIFN-co or rSIFN-co substitute in a range of about 5 mcg/ml to about 20 mcg/ml; optionally, about 10 mcg/ml. In some embodiments, the cancer cells employed in determining activity (c) are treated by the test interferon and/or rSIFN-co or rSIFN-co substitute for at least about 20 hours; optionally, at least about 24 hours.

In some embodiments, the cancer cells employed in determining activity (d), inhibition of beta-catenin/TCF transcriptional activity in cancer cells, comprise any one or more of lung cancer cells, and colon cancer cells. In some embodiments, the cancer cells employed in determining activity (d) comprise any one or more of: A549 cells, H1299 cells, H460 cells, HT-29 cells, and SW620 cells; optionally, comprise any one or more of: A549 cells, H1299 cells, H460 cells, and SW620 cells. In some embodiments, the cancer cells in employed in determining activity (d) are treated by the test interferon and/or rSIFN-co or rSIFN-co substitute for at least about 20 hours; optionally, at least about 24 hours. In some embodiments, the cancer cells employed in determining activity (d) are treated by the test interferon and/or rSIFN-co or rSIFN-co substitute in a range of about 5 mcg/ml to about 20 mcg/ml; optionally, about 10 mcg/ml. In some embodiments, the transcriptional activity of beta-catenin/TCF is determined by use of a reporter system. In some embodiments, the reporter system comprises TOP-Flash or pSV40-RL plasmid.

In some embodiments, the cancer cells employed in determining activity (e), down-regulation of expression of LRP6 and/or FZD6 in cancer cells, comprise any one or more of: lung cancer cells, and colon cancer cells. In some embodiments, the cancer cells employed in determining activity (e) comprise any one or more of: A549 cells, H460 cells, SW620 cells, and HT-29 cells; optionally, comprise any one or more of: A549 cells, SW620 cells, and HT-29 cells; more optionally, comprise HT-29 cells. In some embodiments, the cancer cells employed in determining activity (e) are treated by the test interferon and/or rSIFN-co or rSIFN-co substitute for at least about 20 hours; optionally, at least about 24 hours. In some embodiments, the cancer cells employed in determining activity (e) are treated by the test interferon and/or rSIFN-co or rSIFN-co substitute in a range of about 5 mcg/ml to about 20 mcg/ml; optionally, about 10 mcg/ml. In some embodiments, in determining activity (e), the expression of LRP6 and/or FZD6 is determined by determining mRNA level of LRP6 and/or FZD6.

In some embodiments, the cancer cells employed in determining activity (f), inhibition of expression of any one or more of: Axin2, CD24, Survivin and ID2, comprise lung cancer cells; optionally, comprise A549 cells. In some embodiments, the cancer cells employed in determining activity (f) are treated by the test interferon and/or rSIFN-co or rSIFN-co substitute for at least about 20 hours; optionally, at least about 24 hours. In some embodiments, the cancer cells employed in determining activity (f) are treated by the test interferon and/or rSIFN-co or rSIFN-co substitute in a range of about 5 mcg/ml to about 20 mcg/ml; optionally, about 10 mcg/ml. In some embodiments, in determining activity (f) the expression of Axin2, CD24, Survivin and/or ID2 is determined by determining its corresponding mRNA level. In some embodiments, in determining activity (f), when the test interferon decreases at least about 30%; optionally, at least about 40%; more optionally, at least about 50%; still more optionally, at least about 60% in expression of any one or more of: Axin2, CD24, Survivin and ID2 in the cancer cells as compared to control, the test interferon and/or rSIFN-co or rSIFN-co substitute are considered to have substantially the same potency or substantial equivalence.

In some embodiments, the cancer cells employed in determining activity (g), inhibition of pseudopod formation, comprise lung cancer cells; optionally, A549 cells. In some embodiments, the cancer cells employed in determining activity (g) are treated by the test interferon and/or rSIFN-co or rSIFN-co substitute for at least about 4 days; optionally, at least about 8 days. In some embodiments, the cancer cells employed in determining activity (g) are treated by the test interferon and/or rSIFN-co or rSIFN-co substitute in a range of about 5 mcg/ml to about 20 mcg/ml; optionally, about 10 mcg/ml.

In some embodiments, the cancer cells employed in determining activity (h), inhibition of beta-catenin expression in cancer cells, comprise any one or more of: lung cancer cells and colon cancer cells. In some embodiments, the cancer cells employed in determining activity (h) comprise any one or more of: A549 cells and SW480 cells. In some embodiments, in determining activity (h) the inhibition of beta-catenin expression is determined by Western Blot. In some embodiments, the cancer cells employed in determining activity (h) are treated by the test interferon and/or rSIFN-co or rSIFN-co substitute for at least about 48 hours; optionally, at least about 72 hours. In some embodiments, the cancer cells employed in determining activity (h) are treated by the test interferon and/or rSIFN-co or rSIFN-co substitute in a range of about 5 mcg/ml to about 20 mcg/ml; optionally, about 10 mcg/ml.

In some embodiments, the cancer cells employed in determining activity (i), up-regulation of expression of any one or more of: DKK-3, KLF-4, and BATF2 in cancer cells, comprise any one or more of: lung cancer cells, and colon cancer cells. In some embodiments, the cancer cells employed in determining activity (i) comprise any one or more of: 1549 cells, H460 cells, SW620 cells, and HT-29 cells; optionally, comprise any one or more of: A549 cells, and SW620 cells. In some embodiments, the cancer cells employed in determining activity (i) are treated by the test interferon and/or rSIFN-co or rSIFN-co substitute for at least about 20 hours; optionally, at least about 24 hours. In some embodiments, the cancer cells employed in determining activity (i) are treated by the test interferon and/or rSIFN-co or rSIFN-co substitute in a range of about 5 mcg/ml to about 20 mcg/ml; optionally, about 10 mcg/ml. In some embodiments, in determining activity (i) the expression of DKK-3, KLF-4 and/or BATF2 is determined by determining its corresponding mRNA level.

In some embodiments, statistical significance means a p value of less than or equal to 0.05, or less than or equal to 0.01, or less than or equal to 0.005, or less than or equal to 0.001, or less than or equal to 0.0005, or less than or equal to 0.0001, when compared to a control.

In some embodiments, the control is not treated with the test interferon or rSIFN-co or rSIFN-co substitute, or is treated with normal saline or PBS, or is treated with IFNα-2b, or the control is untreated control (Mock).

In another aspect, the present invention provides a method of determining or comparing the potency of a compound, such as a test interferon, comprising: (a) providing a plurality of concentrations of the test interferon; (b) determining a first dose response of the test interferon, using the plurality of concentrations of the test interferon, on the viability of a first set of cancer cells under specified conditions; (c) providing a plurality of concentrations of rSIFN-co or rSIFN-co substitute; (d) determining a second dose response of the rSIFN-co or rSIFN-co substitute, using the plurality of concentrations of the rSIFN-co or the rSIFN-co substitute, on viability of a second set of cancer cells under the same specified conditions; and (e) comparing the first dose response with the second dose response. In such a manner, the potency of the compound, such as the test interferon, is determined relative to rSIFN-co or rSIFN-co substitute.

In some embodiments, the rSIFN-co comprises a specified specific activity, and the specific activity is in the range between about $4 \times 10^8$ IU/mg to about $1 \times 10^9$ IU/mg. In some embodiments, the specific activity is in the range between about $4.4 \times 10^8$ IU/mg to about $9 \times 10^8$ IU/mg. In some embodiments, the specific activity is in the range between about $5 \times 10^8$ IU/mg to about $8 \times 10^8$ IU/mg. In some embodiments, the specific activity is in the range between about $6 \times 10^8$ IU/mg to about $7.5 \times 10^8$ IU/mg. Optionally, the specific activity is in the range between about $4 \times 10^8$ IU/mg to $5 \times 10^8$ IU/mg.

In some embodiments, in the methods of determining or comparing the potency of a compound, the concentrations of the test interferon or rSIFN-co are in a range between about 0.2 mcg/ml and about 100 mcg/ml. In some embodiments, the concentrations of the test interferon or rSIFN-co are at least two or more of the following: 0.2 mcg/ml, 0.39 mcg/ml, 0.78 mcg/ml, 1.56 mcg/ml, 3.13 mcg/ml, 6.25 mcg/ml, 12.5 mcg/ml, 25 mcg/ml, 50 mcg/ml, and 100 mcg/ml.

In some embodiments, the cancer cells are treated with the test interferon or rSIFN-co for at least about 20 hr, optionally, at least about 24 hr, still optionally, at least about 48 hr, and more optionally, at least about 72 hr.

In some embodiments, the invention provides the methods as described herein, wherein the rSIFN-co has a potency of being able to reduce viability of the cancer cells by 50% at a concentration in the range of between about 6.25 mcg/ml and about 25 mcg/ml, depending on the cancer cell type. In some embodiments, the rSIFN-co is capable of reducing viability of the cells by 50% at a concentration in the range of between about 6.25 mcg/ml and 12.5 mcg/ml. In another embodiment, the rSIFN-co is capable of reducing viability of the cells by 50% at a concentration in the range of between about 12.5 mcg/ml and 25 mcg/ml. In some embodiments, the $IC_{50}$ of the rSIFN-co is in the range of about 10 mcg/ml to about 18 mcg/ml, optionally, about 10 mcg/ml to about 15 mcg/ml.

In another aspect, the present invention provides a method of determining or comparing potency of a compound, such as a test interferon, relative to rSIFN-co or rSIFN-co substitute, on viability of cancer cells, comprising: (a) providing a plurality of cancer cells; (b) testing a first set of the cancer cells with an amount of the test interferon under specified conditions to generate a first set of viability data; (c) treating a second set of the cancer cells with an effective amount of rSIFN-co or rSIFN-co substitute under the same specified conditions to generate a second set of viability data; and (d) comparing the first set of viability data with the second set of viability data, whereby the potency of the test interferon is determined.

In some embodiments, the cancer cells are treated for a range from about 1 day to about 6 days. In some embodiments, the rSIFN-co is used at a concentration in the range of about 6.25 mcg/ml to about 50 mcg/ml; optionally, about 7 mcg/ml to about 25 mcg/ml; further optionally, about 8 mcg/ml to about 12.5 mcg/ml; still optionally, about 10 mcg/ml. In some embodiments, the rSIFN-co is used at a concentration in the range of about 5 mcg/ml to about 20 mcg/ml. In some embodiments, the rSIFN-co comprises a specified specific activity.

In some embodiments, the cancer cells used herein are chosen from among human tumor cells and animal tumor cells. In some embodiments, the tumor cells are lung tumor cells, or cervical tumor cells, or liver tumor cells, or colon tumor cells, or breast tumor cells, or pancreatic tumor cells, or prostate tumor cells, or viral-induced tumor cells or virally transformed cells. In some embodiments, the cancer cells are chosen from at least one of: A549 cells, SPC-A4 cells, Calu-1 cells, CL-1 cells, H460 cells, H1299 cells, Hela cells, HT-29 cells, Huh-7 cells, MDA-MB-231 cells, PANC-1 cells, RAW264.7 cells, SMMC-7721 cells, SW480 cells, and SW620 cells.

In some embodiments, the test interferon is also an interferon, including an interferon obtained from a different manufacturing lot than the rSIFN-co. In some embodiments, the amino acid sequence of the test interferon is at least 90%, optionally, at least 95%, 96%, 97%, 98%, 99%, 100% identical to that of rSIFN-co (SEQ ID NO: 1). In some embodiments, the nucleotide sequence encoding the test interferon is at least 90%, optionally, at least 95%, 96%, 97%, 98%, 99%, 100% identical to that encoding rSFIN-co (SEQ ID NO: 2). In some embodiments, the test interferon and rSIFN-co have same amino acid sequence (SEQ ID NO: 1) and are encoding by same nucleotide sequence (SEQ ID NO: 2). In some embodiments, the test interferon and rSIFN-co have substantially the same specific activity. In some embodiments, the specific activity is in the range between about $4 \times 10^8$ IU/mg to about $1 \times 10^9$ IU/mg. In some embodiments, the test interferon is obtainable by a process comprising introducing into E. coli the polynucleotide sequence shown in SEQ ID NO:2. In some embodiments, the test interferon is made by expression of the polynucleotide (SEQ ID NO:2) in a E. coli host, optionally under the control of promoter $P_{BAD}$ in a E. coli host.

In another aspect, the present invention provides a method of inhibiting cell migration, such as that occurring in tumor metastases, comprising exposing the cells to an effective amount of rSIFN-co for a specified period of time, whereby cell migration is inhibited.

In some embodiments, the effective amount of the rSIFN-co comprises about 5 mcg/ml to about 100 mcg/ml; optionally, about 8 mcg/ml to about 50 mcg/ml; still optionally, about 10 mcg/ml to about 25 mcg/ml; further optionally, about 12 mcg/ml to about 18 mcg/ml. In some embodiments, the effective amount of the rSIFN-co comprises about 5 mcg/ml to about 20 mcg/ml; optionally, about 10 mcg/ml.

In another aspect, the invention provides a method of inhibiting pseudopod formation in cancer cells, comprising exposing the cancer cells to an effective amount of rSIFN-co, for a specified period of time, whereby pseudopod formation is inhibited. In some embodiments, the effective amount of the rSIFN-co comprises about 5 mcg/ml to about 20 mcg/ml; optionally, about 10 mcg/ml.

In a further aspect, the invention provides a method of inhibiting beta-catenin/TCF-mediated transcriptional activity in cells, comprising exposing the cells to an effective amount of rSIFN-co for a specified period of time. In some embodiments, the beta-catenin/TCF-mediated transcriptional activity is determined using a reporter system, optionally, a luciferase reporter system. In some embodiments, the reporter system is TOPFlash reporter. In some embodiments, the plasmid pSV40-RL is used.

In another aspect, the invention additionally provides a method of decreasing beta-catenin protein level in cells comprising exposing cells to an effective amount of rSIFN-co for a specified period of time. In some embodiments, the protein level of beta-catenin is detected by Western Blot using its specific antibody. In some embodiments, GAPDH is used as a control.

In another aspect, the invention provides a method for down-regulating expression of a Wnt-related receptor or co-receptor in cells, comprising exposing the cells to an effective amount of rSIFN-co for a specified time, whereby the Wnt-related receptor or co-receptor is down-regulated. In some embodiments, the Wnt-related receptor or co-receptor comprises a LRP protein, such as LRP6. In some embodiments, the Wnt-signaling receptor or co-receptor comprises a FZD protein, such as FZD6. In some embodiments, determining the expression of the Wnt-related receptor or co-receptor comprises determining the mRNA level of such receptor or co-receptor. In some embodiments, cDNA corresponding to such mRNA is made to determine such mRNA levels.

In a further aspect, the invention provides a method of inhibiting the expression of certain genes in cells, including at least one target gene of the Wnt-signaling pathway, such as for treatment of a disease or condition in which the target gene is over-active. Such down-regulated genes include Axin2, CD24, Survivin, and/or ID2. The method comprises exposing the cells to an effective amount of rSIFN-co for a specified period of time, whereby expression of the target gene is inhibited.

In some embodiments of the invention, the specified period of time for exposure of cells to rSIFN-co is at least about 12 hr; optionally, at least about 20 hr; further optionally, at least about 24 hr; more optionally, for at least about 36 hr; still optionally, at least for about 48 hr; yet still optionally, at least about 72 hr. In some embodiments, the cells being treated by rSIFN-co are cancer cells.

In a further aspect, the invention provides a method of up-regulating expression of certain genes in cells, including at least one tumor suppressor gene, comprising exposing the cells to an effective amount of rSIFN-co for a specified period of time, whereby up-regulation of expression at least one tumor suppressor gene is effected. In some embodiments, the up-regulated gene comprises at least one of DKK3, KLF4, and BATF2. In some embodiments, the expression of the up-regulated gene is determined by measuring such mRNA level. In some embodiments, cDNA is synthesized from such mRNA and is optionally amplified for such measurement purposes.

In another aspect, the invention provides a method of establishing substantial equivalence between a test compound and rSIFN-co or rSIFN-co substitute in at least one, optionally at least 2, 3, 4, 5, 6, 7, 8 or 9 of the following, comprising comparing the activities thereto and showing substantially the same responses: (a) inhibition of in vivo cancer cell growth in any one or more tumor-bearing animal models; (b) Reduction in cancer cell viability; (c) Inhibition of cancer cell migration; (d) Inhibition of beta-catenin/TCF transcriptional activity in cancer cells; (e) Down-regulation of expression of LRP6 and/or FZD6 in cancer cells; (f) Inhibition of expression of any one or more of: Axin2, CD24, Survivin and ID2 in cancer cells; (g) Inhibition of pseudopod formation in cancer cells; (h) Inhibition of beta-catenin expression in cancer cells; and (i) Up-regulation of expression of any one or more of: DKK-3, KLF-4, and BATF2 in cancer cells. In some embodiments, the invention provides establishing substantial equivalence in at least 2 of the fore-mentioned activities; optionally the invention provides establishing substantial equivalence in at least 3 of the fore-mentioned activities; optionally, in at least 4 of the fore-mentioned activities; still optionally, in at least 5 of the fore-mentioned activities; further optionally, in at least 6 of the fore-mentioned activities; still further optionally, in at least 7 or 8 or 9 of the fore-mentioned activities.

In another aspect, the present invention provides assay kits for assessing potency of a test interferon, for inhibiting expression of at least one Wnt-related target gene, for up-regulation of a tumor suppressor gene, and/or for down-regulating expression of LRP6 and/or FZD6, comprising (a) rSIFN-co or rSIFN-co substitute and (h) at least one of: instructions for performing one or more of the methods described herein and reagents for performing such methods. The reagent may include Phosphate Buffered Saline (PBS) or a buffer. In some embodiments, the rSIFN-co or rSIFN-co substitute in the assay kit comprises a specified specific activity.

In another aspect, the present invention provides an interferon or an interferon substitute, comprising any one or more activities, optionally 2, 3, 4, 5, 6, 7, 8, or 9 activities selected from: inhibition of in vivo cancer cell growth in any one or more tumor-bearing animal models; reduction in cancer cell viability; inhibition of cancer cell migration; inhibition of beta-catenin/TCF transcriptional activity in cancer cells; down-regulation of expression of LRP6 and/or FZD6 in cancer cells; inhibition of expression of any one or more of: Axin2, CD24, Survivin and ID2 in cancer cells; inhibition of pseudopod formation in cancer cells; inhibition of beta-catenin expression in cancer cells; and up-regulation of expression of any one or more of: DKK-3, KLF-4, and BATF2 in cancer cells.

DETAILED DESCRIPTION OF THE INVENTION

Definitions

Figure 1:
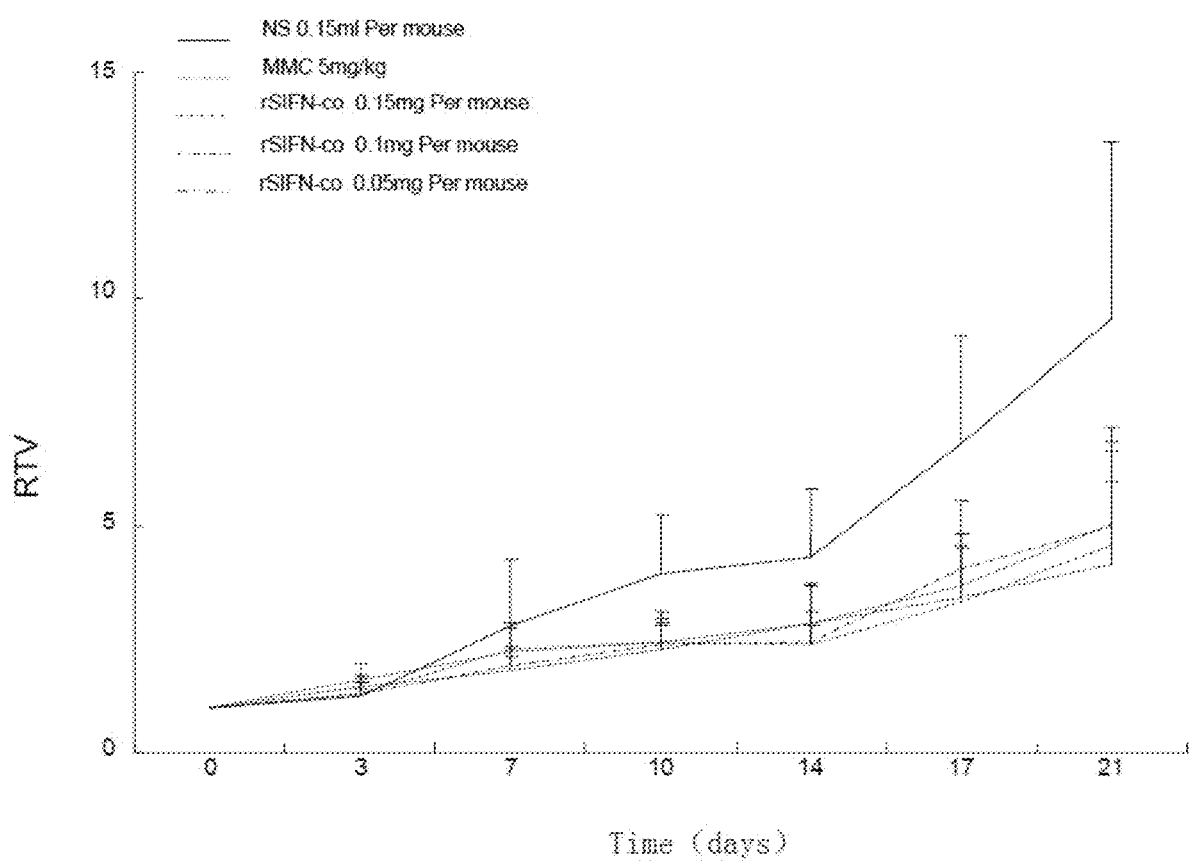
FIG. 1 shows the growth curves of human hepatoma tumors, SMMC-7721, in nude mice, as described in Example 1, as represented by mean relative tumor volume (RTV), for each of the groups treated with either MMC (at 5 mg/kg) or rSIFN-co at 0.15 mg/mouse, 0.10 mg/mouse or 0.05 mg/mouse, or was injected with vehicle, normal saline (NS) (0.15 ml/mouse), over the 21-day period after the start of treatment.

Unless otherwise indicated, scientific and technical terms used herein shall have the meanings given them by those of ordinary skill in the art or that are commonly understood by those of ordinary skill in the art.

Further, unless otherwise required by context, singular terms shall include pluralities and plural terms shall include the singular.

In addition, as used herein, the term "or" shall mean "and/or" unless otherwise stated.

As used herein, the term "compound" shall mean any protein (including any antibody, any active antibody fragment, and any dimeric or multimeric protein), polypeptide, small molecule, and other molecules having one or more biological activities.

The term "comprise" or "comprising" as used herein shall be read expansively and without limitation, and shall include "is" or "are."

The term "condition" and "disease" as used herein may be used interchangeably or together to indicate an illness, infection, inflammation, cancer, a side effect caused by treatment, or other causes of poor health in a subject.

The term "effective amount" as used herein shall mean an amount that produces the desired effect, such as for reduction of cell viability, down-regulation or up-regulation of expression or activity of a protein, or treatment of a disease or condition.

The term "establishing substantial equivalence" as used herein shall mean conducting certain test or tests to demonstrate substantially the same level of response, activity, effectiveness or result, within the limits of experimental error (such as ±standard deviation (SD)).

The term "substantially the same" as used herein shall mean at least about 70% the same; optionally, at least about 80% the same; still optionally, at least about 90% the same; further optionally, at least about 95% the same.

The terms "in the range of about" or "in the range between about" as used herein shall mean the number specified in the range plus all units and decimal points in-between such specified range. For example, "in the range between about $4 \times 10^8$ IU/mg to about $5 \times 10^8$ IU/mg" shall include $4 \times 10^8$ IU/mg, $4.1 \times 10^8$ IU/mg, $4.2 \times 10^8$ IU/mg, $4.3 \times 10^8$ IU/mg, $4.4 \times 10^8$ IU/mg, and the like, and "8 mcg/ml to 20 mcg/ml" shall include 9 mcg/ml, 10 mcg/ml and the like.

The term "include" or "including" as used herein shall be construed as non-limiting and embodies the elements specified as well as non-specified elements.

The term "interferon" or "IFN" as used herein shall mean any naturally occurring or artificially created interferon, including consensus interferon alpha, as described in U.S. Pat. No. 4,695,623, entitled "Consensus human leukocyte interferon," as well as rSIFN-co.

The term "interferon activity" as used herein shall mean one or more biological activities that characterize a naturally occurring interferon and rSIFN-co, such as, for example, anti-tumor activity and/or anti-viral activity.

The term "rSIFN-co" as used herein shall mean the protein or nucleic acid molecule, as the context requires, having the polynucleotide sequence and amino acid sequence as described in U.S. Pat. Nos. 7,364,724, 7,585,647, or an active fragment of such. Said polynucleotide sequence and amino acid sequence as described in U.S. Pat. Nos. 7,364,724, and 7,585,647 are follows:

```
             M   C   D   L   P   Q    T   H   S   L   G   N    R   R   A   L   I   L    L   A
   1 ATGTGCGACC TGCCGCAGAC CCACTCCCTG GGTAACCGTC GTGCTCTGAT CCTGCTGGCT

TACACGCTGG ACGGCGTCTG GGTGAGGGAC CCATTGGCAG CACGAGACTA GGACGACCGA

Q   M   R   R   I   S    P   F   S   C   L   K    D   R   H   D   F   G    F   P
  61 CAGATGCGTC GTATCTCCCC GTTCTCCTGC CTGAAAGACC GTCACGACTT CGGTTTCCCG

GTCTACGCAG CATAGAGGGG CAAGAGGACG GACTTTCTGG CAGTGCTGAA GCCAAAGGGC
```

-continued

```
       Q   E   E   F   D   G   N   Q   F   Q   K   A   Q   A   I   S   V   L   H   E
    121 CAGGAAGAAT TCGACGGTAA CCAGTTCCAG AAAGCTCAGG CTATCTCCGT TCTGCACGAA

GTCCTTCTTA AGCTGCCATT GGTCAAGGTC TTTCGAGTCC GATAGAGGCA AGACGTGCTT

M   I   Q   Q   T   F   N   L   F   S   T   K   D   S   S   A   A   W   D   E
    181 ATGATCCAGC AGACCTTCAA CCTGTTCTCC ACCAAAGACT CCTCCGCTGC TTGGGACGAA

TACTAGGTCG TCTGGAAGTT GGACAAGAGG TGGTTTCTGA GGAGGCGACG AACCCTGCTT

S   L   L   E   K   F   Y   T   E   L   Y   Q   Q   L   N   D   L   E   A   C
    241 TCCCTGCTGG AAAAATTCTA CACCGAACTG TACCAGCAGC TGAACGACCT GGAAGCTTGC

AGGGACGACC TTTTTAAGAT GTGGCTTGAC ATGGTCGTCG ACTTGCTGGA CCTTCGAACG

V   I   Q   E   V   G   V   E   E   T   P   L   M   N   V   D   S   I   L   A
    301 GTTATCCAGG AAGTTGGTGT TGAAGAAACC CCGCTGATGA ACGTTGACTC CATCCTGGCT

CAATAGGTCC TTCAACCACA ACTTCTTTGG GGCGACTACT TGCAACTGAG GTAGGACCGA

V   K   K   Y   F   Q   R   I   T   L   Y   L   T   E   K   K   Y   S   P   C
    361 GTTAAAAAAT ACTTCCAGCG TATCACCCTG TACCTGACCG AAAAAAAATA CTCCCCGTGC

CAATTTTTTA TGAAGGTCGC ATAGTGGGAC ATGGACTGGC TTTTTTTTAT GAGGGGCACG

A   W   E   V   V   R   A   E   I   M   R   S   F   S   L   S   T   N   L   Q
    421 GCTTGGGAAG TTGTTCGTGC TGAAATCATG CGTTCCTTCT CCCTGTCCAC CAACCTGCAG

CGAACCCTTC AACAAGCACG ACTTTAGTAC GCAAGGAAGA GGGACAGGTG GTTGGACGTC (SEQ ID NO: 1)
        E   R   L   R   R   K   E (SEQ ID NO: 2)
    481 GAACGTCTGC GTCGTAAAGA ATAA (SEQ ID NO: 3)
        CTTGCAGACG CAGCATTTCT TATT
```

The term "rSIFN-co substitute," as used herein shall mean any compound, the potency of which has been or will be measured against rSIFN-co and can be used in place of rSIFN-co for comparative purposes in the determination of potency or activity of a test compound. The rSIFN-co substitute may be an interferon or a compound having interferon properties.

As used herein, specific activity is the ratio of the biological activity and the content of protein. The biological activity can be any relevant biological activity as conventional in the art, such as the biological activity measured by cell lesion inhibition method published in Appendix X C in Chinese Pharmacopoeia (the 3$^{rd}$ book), 2010 edition. The protein content can be measured by any method conventional in the art, such as the Lowry method, published in Appendix VI B in Chinese Pharmacopoeia (the 3$^{rd}$ book), 2010 edition.

The ten "treatment" as used herein shall include causing a complete or partial cure of a disease, arresting or inducing non-progression of a disease, ameliorating or reducing the severity of a disease or symptoms, preventing the recurrence of a disease, reducing the frequency of recurrence of a disease, reducing side effects of a disease, placing a disease in remission, causing a general feeling of improved health and the like.

The term "Wnt-related receptor or co-receptor" shall include one or more molecules that individually or together binds to a Wnt family protein to initiate signaling in the canonical Wnt signaling pathway or non-canonical Wnt signaling pathway in cells. This term includes, for example, LRP6, a low density lipoprotein receptor-related protein 6, which is known to interact with DKK1, a Wnt-coreceptor and FZD6, a receptor for Wnt signaling and believed to be a receptor for Wnt-4 ligand.

The term "Wnt signaling activity" as used herein refers to the Wnt signaling cascade transduced through binding to Frizzled (FZD) family receptors and LRP5/LRP6 co-receptor, leading to the release of beta-catenin and its migration into the nucleus for cell activation.

The inventors herein discovered certain biological effects resulting from administration or treatment of rSIFN-co and that these biological effects can be employed to assess the potency of rSIFN-co and other compounds that may have similar properties, especially during the manufacturing process when consistency in potency is desired or in drug development process when improvement in potency is sought. The inventors have further discovered certain biological effects upon treatment with rSIFN-co, heretofore unknown, and that such biological effects may be employed for further uses of rSIFN-co, including for the treatment of other conditions or diseases where up-regulation or down-regulation of certain genes is desirable.

In one aspect, the present invention provides a method of determining or comparing potency of a test interferon relative to rSIFN-co or a rSIFN-co substitute comprising: (1) providing the test interferon and rSIFN-co or rSIFN-co substitute; and (2) determining any one or more of the following activities of the test interferon and rSIFN-co or rSIFN-co substitute under same specified conditions, respectively: (a) Inhibition of in vivo cancer cell growth in any one or more tumor-bearing animal models; (b) Reduction in cancer cell viability; (c) Inhibition of cancer cell migration; (d) Inhibition of beta-catenin/TCF transcriptional activity in cancer cells; (e) Down-regulation of expression of LRP6 and/or FZD6 in cancer cells; (f) Inhibition of expression of any one or more of: Axin2, CD24, Survivin and ID2 in cancer cells; (g) Inhibition of pseudopod formation in cancer cells; (h) Inhibition of beta-catenin expression in cancer cells; and (i) tip-regulation of expression of any one or more of: DKK-3, KU-4, and BATF2 in cancer cells; whereby the presence in the test interferon of any 1, or 2, or 3, or 4, or 5, or 6 of the activities specified in (a), (b), (c), (d), (e), and (f), in a statistically significant manner, and/or the presence in the test interferon of any one or more of the activities specified in (g), (h) and (i), signifies that the test interferon and rSIFN-co or rSIFN-co substitute have substantially the same potency.

In another aspect, the present invention provides a method of establishing substantial equivalence between a test interferon and rSIFN-co or a rSIFN-co substitute comprising: (1) providing the test interferon and rSIFN-co or rSIFN-co substitute; and (2) determining any one or more of the following activities of the test interferon and rSIFN-co or rSIFN-co substitute under same specified conditions, respectively: (a) Inhibition of in vivo cancer cell growth in any one or more tumor-bearing animal models; (b) Reduction in cancer cell viability; (c) inhibition of cancer cell migration; (d) Inhibition of beta-catenin/TCF transcriptional activity in cancer cells; (e) Down-regulation of expression of LRP6 and/or FZD6 in cancer cells; (f) Inhibition of expression of any one or more of: Axin2, CD24, Survivin and ID2 in cancer cells; (g) Inhibition of pseudopod formation in cancer cells; (h) Inhibition of beta-catenin expression in cancer cells; and (i) Up-regulation of expression of any one or more of: DKK-3, KLF-4, and BATF2 in cancer cells; whereby the presence in the test interferon of any 1, or 2, or 3, or 4, or 5, or 6 of the activities specified in (a), (b), (c), (d), (e), and (f), in a statistically significant manner, and/or the presence in the test interferon of any one or more of the activities specified in (g), (h) and (i), signifies that the test interferon and rSIFN-co or rSIFN-co substitute are substantial equivalence. Optionally, the presence of reduction in tumor cell viability in vitro, such as in A549 cells and/or SW620 cells, in combination with inhibition of transcriptional activity of beta-catenin/TCF, such as in any one or more of: A549 cells, H1299 cells, H460 cells and HT-29 cells, in a statistically significant manner, and optionally, the additional presence of JAK/STAT signaling, all upon treatment or administration of the test interferon, indicate substantial equivalence between the test interferon and rSIFN-co. Further optionally, the determination of cell viability can be conducted upon treatment of the appropriate cells with the test interferon for about 1 to about 6 days at, for example, about 10 mcg/ml. Optionally, the inhibition of beta-catenin/TCF transcriptional activity is determined in any one or more of cancer cells: A549, H1299, H460, or HT-29, for example, by treatment of these cells with about 10 mcg/ml of the test interferon for about 24 hr. Optionally, the JAK/STAT signaling is determined by determining the presence of phosphorylation of STAT proteins, such as STAT1, STAT2 and/or STAT3, such as upon treatment of A549 cells or Hela cells, with about 10 mcg/ml of the test interferon for various times, such as about 5, 15, 30, 60, 120, and/or 240 minutes.

In some embodiments, in step (2) of above methods, at least 2 of the fore-mentioned activities on the test interferon and rSIFN-co or rSIFN-co substitute under same specified conditions are determined, such as (a) and (b); (a) and (c); (a) and (d); (a) and (e); (a) and (f); (a) and (g); (a) and (b); (a) and (i); (b) and (c); (b) and (d); (b) and (e); (b) and (f); (b) and (g); (b) and (h); (b) and (i); (c) and (d); (c) and (e); (c) and (I); (c) and (g); (c) and (h); (c) and (i); (d) and (e); (d) and (f); (d) and (g); (d) and (h); (d) and (i); (e) and (f); (e) and (g); (e) and (h); (e) and (i); (f) and (g); (f) and (h); (f) and (i); (g) and (h); (g) and (i); (h) and (i).

In some embodiments, in step (2) of above methods, at least 3 of the fore-mentioned activities on the test interferon and rSIFN-co or rSIFN-co substitute under same specified conditions are determined, such as (a), (b) and (c); (a), (b) and (d); (a), (b) and (e); (a), (b) and (f); (a), (b) and (g); (a), (b) and (h); (a), (b) and (i); (a), (c) and (d); (a), (c) and (e); (a), (c) and (f); (a), (c) and (g); (a), (c) and (h); (a), (c) and (i); (a), (d) and (e); (a), (d) and (f); (a), (d) and (g); (a), (d) and (h); (a), (d) and (i); (a), (e) and (f); (a), (e) and (g); (a), (e) and (h); (a), (e) and (i); (a), (f) and (g); (a), (f) and (h); (a), (f) and (i); (a), (g) and (h); (a), (g) and (i), (a), (h) and (i); (b), (c) and (d); (b), (c) and (e); (b), (c) and (f); (b), (c) and (g); (b), (c) and (h); (b), (c) and (i); (b), (d) and (e); (b), (d) and (f); (b), (d) and (g); (b), (d) and (h); (b), (d) and (i); (b), (e) and (f); (b), (e) and (g); (b), (e) and (h); (b), (e) and (i); (b), (f) and (g); (b), (f) and (h); (b), (f) and (i); (b), (g) and (i); (b), (g) and (i); (b), (h) and (i); (c), (d) and (e); (c), (d) and (f); (c), (d) and (g); (c), (d) and (h); (c), (d) and (i); (c), (e) and (f); (c), (e) and (g); (c), (e) and (h); (c), (e) and (i); (c), (f) and (g); (c), (f) and (h); (c), (f) and (i); (c), (g) and (h); (c), (g) and (i); (c), (h) and (i); (d), (e) and (f); (d), (e) and (g); (d), (e) and (h); (d), (e) and (i); (d), (f) and (g); (d), (f) and (h); (d), (f) and (i); (d), (g) and (h); (d), (g) and (i); (d), (h) and (i); (e), (f) and (g); (e), (f) and (h); (e), (f) and (i); (e), (g) and (h); (e), (g) and (i); (e), (h) and (i); (f), (g) and (h); (f), (g) and (i); (g), (h) and (i).

In some embodiments, in step (2) of above methods, at least 4 of the fore-mentioned activities on the test interferon and rSIFN-co or rSIFN-co substitute under same specified conditions are determined, such as (a), (b), (c) and (d); (a), (b), (c), and (e); (a), (b), (c) and (f); (a), (b), (c) and (g); (a), (b), (c) and (h); (a), (b), (c) and (i); (a), (c), (d) and (e); (a), (c), (d) and (f); (a), (c), (d) and (g); (a), (c), (d) and (h); (a), (c), (d) and (i); (a), (d), (e) and (f); (a), (d), (e) and (g); (a), (d), (e) and (h); (a), (d), (e) and (i); (a), (e), (f) and (g); (a), (e), (f) and (h); (a), (e), (f) and (i); (a), (f), (g) and (h); (a), (f), (g) and (i); (a), (g), (h) and (i); (b), (c), (d) and (e); (b), (c), (d) and (f); (b), (c), (d) and (g); (b), (c), (d) and (h); (b), (c), (d) and (i); (b), (d), (e) and (f); (b), (d), (e) and (g); (b), (d), (e) and (h); (b), (d), (e) and (i); (b), (e), (f) and (g); (b), (e), (f) and (h); (b), (e), (f) and (i); (b) (f), (g), and (h); (b), (f), (g), and (i); (b) (g), (h), and (i); (c), (d) (e), and (f); (c), (d), (e), and (g); (c), (d), (e), and (h); (c), (d), (e), and (i); (c), (d), (f) and (g); (c), (d), (f) and (h); (c), (d), (f) and (i); (c), (d), (g) and (h); (c), (d), (g) and (i); (c), (d), (h) and (i); (c), (e), (f) and (g); (c), (e), (f) and (h); (c), (e), (f) and (i); (c), (f), (g) and (h); (c), (f), (g) and (i); (c), (g), (h) and (i); (d), (e), (f) and (g); (d), (e), (f) and (h); (d), (e), (f) and (i); (d), (f), (g), and (h); (d), (f) (g), and (i); (d), (g) (h) and (i), (e), (f), (g) and (h); (e), (f), (g) and (i), (e), (g), (h) and (i); (f), (g), (h) and (i).

In some embodiments, in step (2) of above methods, at least 5 of the fore-mentioned activities on the test interferon and rSIFN-co or rSIFN-co substitute under same specified conditions are determined, such as (a), (b), (c), (d), and (e); (a), (b), (c), (d), and (f); (a), (b), (c), (d), and (g); (a), (b), (c), (d), and (h); (a), (b), (c), (d), and (i); (a), (c), (d), (e) and (f); (a), (c), (d), (e) and (g); (a), (c), (d), (e) and (h); (a), (c), (d), (e) and (i); (a), (d), (e), (f) and (g); (a), (d), (e), (f) and (h); (a), (d), (e), (f) and (i); (a), (e), (f), (g) and (h); (a), (e), (f), (g) and (i); (a), (f), (g), (h) and (i); (b), (c), (d), (e) and (f); (b), (c), (d), (e) and (g); (b), (c), (d), (e) and (h); (b), (c), (d), (e) and (i); (b), (d), (e), (f) and (g); (b), (d), (e), (f) and (h); (b), (d), (e), (f) and (i); (b), (e), (f), (g) and (h); (b), (e), (f), (g) and (i); (b), (f), (g), (h) and (i); (c), (d), (e), (f) and (g); (c), (d), (e), (f) and (h); (c), (d), (e), (f) and (i); (c), (e), (f), (g) and (h); (c), (e), (f), (g) and (i); (c), (f), (g), (h) and (i); (d), (e), (f), (g), and (h); (d), (e), (f), (g), and (i); (d), (f), (g), (h) and (i).

In some embodiments, in step (2) of above methods, at least 6 of the fore-mentioned activities on the test interferon and rSIFN-co or rSIFN-co substitute under same specified conditions are determined, such as (a), (b), (c), (d), (e), and (f); (a), (b), (c), (d), (e), and (g); (a), (b), (c), (d), (e), and (h); (a), (b), (c), (d), (e), and (i); (a), (c), (d), (e), (f), and (g); (a), (c), (d), (e), (f), and (h); (a), (c), (d), (e), (f), and (i); (a), (d), (e), (f), (g) and (h); (a), (d), (e), (f), (g) and (i); (a), (e), (f), (g), (h) and (i); (b), (c), (d), (e), (f), and (g); (b), (c), (d), (e), (f), and (h); (b), (c), (d), (e), (f), and (i); (b), (d), (e), (f), (g) and (h); (b), (d), (e), (f), (g) and (i); (b), (e), (f), (g), (h) and (i); (c), (d), (e), (f), (g), and (h); (c), (d), (e), (f), (g), and (i); (c), (e), (f), (g), (h) and (i); (d), (e), (f), (g), (h) and (i).

In some embodiments, in step (2) of above methods, at least 7 of the fore-mentioned activities on the test interferon and rSIFN-co or rSIFN-co substitute under same specified conditions are determined, such as (a), (b), (c), (d), (e), (f), and (g); (a), (b), (c), (d), (e), (f), and (h); (a), (b), (c), (d), (e), (f), and (i); (a), (c), (d), (e), (f), (g) and (h); (a), (c), (d), (e), (f), (g) and (i); (a), (d), (e), (f), (g), (h) and (i); (b), (c), (d), (e), (f), (g) and (h); (b), (c), (d), (e), (f), (g) and (i); (b), (d), (e), (f), (g), (h) and (i); (c), (d), (e), (f), (g), (h) and (i).

In some embodiments, in step (2) of above methods, at least 8 of the fore-mentioned activities on the test interferon and rSIFN-co or rSIFN-co substitute under same specified conditions are determined, such as (a), (b), (c), (d), (e), (f), (g) and (h); (a), (b), (c), (d), (e), (f), (g) and (i); (b), (c), (d), (e), (g), (h) and (i); (a), (c), (d), (e), (f), (g), (h) and (i); (a), (b), (d), (e), (f), (g), (h) and (i); (a), (b), (c), (e), (f), (g), (h) and (i); (a), (b), (c), (d), (g), (h) and (i); (a), (b), (c), (d), (e), (g), (h) and (i); (a), (b), (c), (d), (e), (f), (h) and (i); (a), (b), (c), (d), (e), (f), (g) and (i).

In some embodiments, in step (2) of above methods, all 9 of the fore-mentioned activities on the test interferon and rSIFN-co or rSIFN-co substitute under same specified conditions are determined, such as (a), (b), (c), (d), (e), (f), (g), (h) and (i).

In some embodiments, in determining activity (a), when as compared to control, the presence in the test interferon of activity specified in (a) in a statistically significant manner (such as, $p<0.05$, optionally, $p<0.01$, further optionally, $p<0.005$, more optionally, $p<0.001$, still optionally, $p<0.0005$, still more optionally, $p<0.0001$), signifies that the test interferon and rSIFN-co or rSIFN-co substitute have substantially the same potency and/or are substantial equivalence.

In some embodiments, the tumor-bearing animal models employed in determining activity (a) comprise mice, optionally, nude mice, more optionally, BALB/cA nu/nu mice. In some embodiments, the mice, such as the BALB/cA nu/nu mice, comprise about 3 weeks old to about 7 weeks old mice, optionally, comprise about 4 weeks old to about 6 weeks old mice. In some embodiments, the body weight of the mice, such as the BALB/cA nu/nu mice, is in a range of about 15±2 g to about 30±2 g; optionally, in a range of about 19±2 g to about 23±2 g.

In some embodiments, the cancer cells employed in determining activity (a), inhibition of in vivo cancer cell growth, comprise any one or more of: liver cancer cells, cervical cancer cells, colon cancer cells, and lung cancer cells. In some embodiments, the cancer cells employed in determining activity (a) comprise any one or more of: SMMC-7721 cells, Hela cells, HT-29 cells, SPC-A4 cells, and A549 cells; optionally, comprise any one or more of: HT-29 cells, SPC-A4 cells, and A549 cells; further optionally, comprise A549 cells.

In some embodiments, normal saline or PBS, optionally, normal saline is used as control in determining inhibition in activity (a). In some embodiments, the test interferon and/or rSIFN-co or rSIFN-co substitute administered to a tumor-bearing animal model in determining activity (a), is administered in a range of about 0.02 mg to about 0.30 mg; optionally, about 0.05 mg to about 0.15 mg; further optionally, about 0.075 mg to about 0.10 mg. In some embodiments, the test interferon and/or rSIFN-co or rSIFN-co substitute, administered to a tumor-bearing animal model in determining activity (a), is administered every other day. In some embodiments, the test interferon and/or rSIFN-co or rSIFN-co substitute, administered to a tumor-bearing animal model in determining activity (a), is administered for about 2 weeks to about 6 weeks; optionally, about 3 weeks to about 4 weeks. In some embodiments, the control administered to a tumor-bearing animal model in determining activity (a), is administered in a range of about 0.05 ml to about 0.30 ml; optionally, about 0.10 ml to about 0.20 ml. In some embodiments, the control, administered to a tumor-bearing animal model in determining activity (a), is administered every other day. In some embodiments, the control, administered to a tumor-bearing animal model in determining activity (a), is administered for about 2 weeks to about 6 weeks; optionally, about 3 weeks to about 4 weeks. In some embodiments, the test interferon and/or control is administered intratumorally.

In some embodiments, in determining activity (a), when SMMC-7721 cells are employed in determining activity (a), as compared to control (such as normal saline), the presence in the test interferon of activity specified in (a) in a statistically significant ma (such as $p<0.05$ for about 0.05 mg and about 0.10 mg, optionally, $p<0.01$ for about 0.15 mg), signifies that the test interferon and rSIFN-co or rSIFN-co substitute have substantially the same potency and/or are substantial equivalence. In some embodiments, the test interferon and/or rSIFN-co or rSIFN-co substitute is administered every other day in a range of about 0.02 mg to about 0.30 mg; optionally, about 0.05 mg to about 0.15 mg; further optionally, about 0.075 mg to about 0.10 mg, for about 3 weeks.

In some embodiments, in determining activity (a), when Hela cells are employed in determining activity (a), as compared to control (such as normal saline), the presence in the test interferon of activity specified in (a) in a statistically significant manner (such as $p<0.05$ for about 0.15 mg, optionally, $p<0.01$ for about 0.05 mg and about 0.10 mg), signifies that the test interferon and rSIFN-co or rSIFN-co substitute have substantially the same potency and/or are substantial equivalence. In some embodiments, the test interferon and/or rSIFN-co or rSIFN-co substitute is administered every other day in a range of about 0.02 mg to about 0.30 mg; optionally, about 0.05 mg to about 0.15 mg; further optionally, about 0.075 mg to about 0.10 mg, for about 4 weeks.

In some embodiments, in determining activity (a), when HT-29 cells are employed in determining activity (a), as compared to control (such as normal saline), the presence in the test interferon of activity specified in (a) in a statistically significant manner (such as $p<0.01$ for about 0.10 mg and 0.15 mg, optionally, $p<0.001$ for about 0.05 mg), signifies that the test interferon and rSIFN-co or rSIFN-co substitute have substantially the same potency and/or are substantial equivalence. In some embodiments, the test interferon and/ or rSIFN-co or rSIFN-co substitute is administered every other day in a range of about 0.02 mg to about 0.30 mg; optionally, about 0.05 mg to about 0.15 mg; further optionally, about 0.075 mg to about 0.10 mg, for about 4 weeks.

In some embodiments, in determining activity (a), when SPC-A4 cells are employed in determining activity (a), as compared to control (such as normal saline), the presence in the test interferon of activity specified in (a) in a statistically significant manner (such as $p<0.01$ for about 0.05 mg, about 0.10 mg and about 0.15 mg), signifies that the test interferon and rSIFN-co or rSIFN-co substitute have substantially the same potency and/or are substantial equivalence. In some embodiments, the test interferon and/or rSIFN-co or rSIFN-co substitute is administered every other day in a range of about 0.02 mg to about 0.30 mg; optionally, about 0.05 mg to about 0.15 mg; further optionally, about 0.075 mg to about 0.10 mg, for about 3 weeks.

In some embodiments, in determining activity (a), when A549 cells are employed in determining activity (a), as compared to control (such as PBS), the presence in the test interferon of activity specified in (a) in a statistically significant manner (such as $p<0.0001$), signifies that the test interferon and rSIFN-co or rSIFN-co substitute have substantially the same potency and/or are substantial equivalence. In some embodiments, the test interferon and/or rSIFN-co or rSIFN-co substitute is administered every other day in a range of about 0.02 mg to about 0.30 g; optionally, about 0.05 mg to about 0.15 mg, more optionally, about 0.10 mg for at least about 3 weeks.

In some embodiments, in determining activity (b), reduction in cancer cell viability, when the test interferon causes about 50% reduction in viability of the cancer cells at a concentration in a range of between about 6.25 mcg/ml and about 25 mcg/ml; optionally, between about 10 mcg/ml and about 18 mcg/ml; more optionally, between about 10 mcg/ml and about 15 mcg/ml, signifies that the test interferon and rSIFN-co or rSIFN-co substitute have substantially the same potency and/or are substantial equivalence. In some embodiments, in determining activity (b), when the test interferon causes reduction in cancer cell viability to a substantially undetectable level at a concentration in a range of at least about 25 mcg/ml; optionally, at least about 50 mcg/ml; further optionally, at least about 75 mcg/ml; more optionally, at least about 100 mcg/ml, signifies that the test interferon and rSIFN-co or rSIFN-co substitute have substantially the same potency and/or are substantial equivalence.

In some embodiments, in determining activity (b), the concentrations of the test interferon and/or rSIFN-co or rSIFN-co substitute comprise concentrations in a range of between about 0.2 mcg/ml and about 100 mcg/ml. In some embodiments, the concentrations of the test interferon and/or rSIFN-co or rSIFN-co substitute are at least two or more of the following: 0.2 mcg/ml, 0.39 mcg/ml, 0.78 mcg/ml, 1.56 mcg/ml, 3.13 mcg/ml, 6.25 mcg/ml, 12.5 mcg/ml, 25 mcg/ml, 50 mcg/ml, and 100 mcg/ml. In some embodiments, in determining activity (b), the cancer cells are treated by the test interferon and/or rSIFN-co or rSIFN-co substitute for at least about 1 day; optionally, at least about 2 days.

In some embodiments, the cancer cells employed in determining activity (b) comprise any one or more of: lung cancer cells, colon cancer cells, cervical cancer cells, liver cancer cells, breast cancer cells, and pancreatic cancer cells; optionally, comprise any one or more of: lung cancer cells, colon cancer cells, liver cancer cells, breast cancer cells, and pancreatic cancer cells. In some embodiments, the cancer cells employed in determining activity (b) comprise any one or more of: A549 cells, Hela cells, CL-1 cells, Huh-7 cells, SW480 cells, MDA-MB-231 cells, Calu-1 cells, SMMC-7721 cells, and PANC-1 cells; optionally, comprise any one or more of: A549 cells, CL-1 cells, Huh-7 cells, SW480 cells, MDA-MB-231 cells, Calu-1 cells, SMMC-7721 cells, and PANC-1 cells.

In some embodiments, in determining activity (b), when the test interferon causes about 50% reduction in viability of any one or more of: SW480 cells, MDA-MB-231 cells, and PANC-1 cells at a concentration in a range of between about 6.25 mcg/ml and about 12.5 mcg/ml, signifies that the test interferon and rSIFN-co or rSIFN-co substitute have substantially the same potency and/or are substantial equivalence.

In some embodiments, in determining activity (b), when the test interferon causes about 50% reduction in viability of any one or more of: A549 cells, Hela cells, CL-1 cells, Huh-7 cells, Calu-1 cells, and SMMC-7721 cells at a concentration in a range of between about 12.5 mcg/ml and about 25 mcg/ml, signifies that the test interferon and rSIFN-co or rSIFN-co substitute have substantially the same potency and/or are substantial equivalence.

In some embodiments, in determining activity (b), when A549 cells and/or SW620 cells are employed in determining activity (b), as compared to control (such as IFNα-2b), the presence in the test interferon of activity specified in (b) in a statistically significant manner (such as $p<0.01$), signifies that the test interferon and rSIFN-co or rSIFN-co substitute have substantially the same potency and/or are substantial equivalence. In some embodiments, the cancer cells employed in determining activity (b) are treated by the test interferon and/or rSIFN-co or rSIFN-co substitute in a range of about 5 mcg/ml to about 20 mcg/ml; optionally, about 10 mcg/ml. In some embodiments, the cancer cells employed in determining activity (b) are treated for about 1 day to about 10 days; optionally, about 1 day to about 6 days.

In some embodiments, in determining activity (b), the cancer cell viability is determined by Am-Blue method or MTT method.

In some embodiments, in determining activity (c), when as compared to control, the presence in the test interferon of activity specified in (c) in a statistically significant manner (such as, $p<0.01$), signifies that the test interferon and rSIFN-co or rSIFN-co substitute have substantially the same potency and/or are substantial equivalence. In some embodiments, the control is untreated control (Mock).

In some embodiments, the cancer cells employed in determining activity (c), inhibition of cancer cell migration, comprise any one or more of: lung cancer cells, and colon cancer cells. In some embodiments, the cancer cells employed in determining activity (c) comprise any one or more of: A549 cells, and SW620 cells. In some embodiments, the inhibition of cancer cell migration in activity (c) is determined using Transwell method. In some embodiments, the cancer cells employed in determining activity (c) are treated by the test interferon and/or rSIFN-co or rSIFN-co substitute in a range of about 5 mcg/ml to about 20 mcg/ml; optionally, about 10 mcg/ml. In some embodiments, the cancer cells employed in determining activity (c) are treated by the test interferon and/or rSIFN-co or rSIFN-co substitute for at least about 20 hours; optionally, at least about 24 hours.

In some embodiments, in determining activity (d), when as compared to control, the presence in the test interferon of activity specified in (d) in a statistically significant manner (such as, $p<0.05$, optionally, $p<0.01$), signifies that the test interferon and rSIFN-co or rSIFN-co substitute have substantially the same potency and/or are substantial equivalence. In some embodiments, the control is untreated control (Mock).

In some embodiments, the cancer cells employed in determining activity (d), inhibition of beta-catenin/TCF transcriptional activity in cancer cells, comprise any one or more of: lung cancer cells, and colon cancer cells. In some embodiments, the cancer cells employed in determining activity (d) comprise any one or more of: A549 cells, H1299 cells, H460 cells, HT-29 cells, and SW620 cells; optionally, comprise any one or more of: A549 cells, H1299 cells, H460 cells, and SW620 cells. In some embodiments, the cancer cells in employed in determining activity (d) are treated by the test interferon and/or rSIFN-co or rSIFN-co substitute for at least about 20 hours; optionally, at least about 24 hours. In some embodiments, the cancer cells employed in determining activity (d) are treated by the test interferon and/or rSIFN-co or rSIFN-co substitute in a range of about 5 mcg/ml to about 20 mcg/ml; optionally, about 10 mcg/ml. In some embodiments, the transcriptional activity of beta-catenin/TCF is determined by use of a reporter system. In some embodiments, the reporter system comprises TOP-Flash or pSV40-RL plasmid.

In some embodiments, in determining activity (e), when as compared to control, the presence in the test interferon of activity specified in (e) in a statistically significant manner (such as, p<0.005, optionally, p<0.001, further optionally, p<0.0005), signifies that the test interferon and rSIFN-co or rSIFN-co substitute have substantially the same potency and/or are substantial equivalence. In some embodiments, the control is untreated control (Mock).

In some embodiments, the cancer cells employed in determining activity (e), down-regulation of expression of LRP6 and/or FZD6 in cancer cells, comprise any one or more of: lung cancer cells, and colon cancer cells. In some embodiments, the cancer cells employed in determining activity (e) comprise any one or more of: A549 cells, H460 cells, SW620 cells, and HT-29 cells; optionally, comprise any one or more of: A549 cells, SW620 cells, and HT-29 cells; more optionally, comprise HT-29 cells. In some embodiments, the cancer cells employed in determining activity (e) are treated by the test interferon and/or rSIFN-co or rSIFN-co substitute for at least about 20 hours; optionally, at least about 24 hours. In some embodiments, the cancer cells employed in determining activity (e) are treated by the test interferon and/or rSIFN-co or rSIFN-co substitute in a range of about 5 mcg/ml to about 20 mg/ml; optionally, about 10 mcg/ml. In some embodiments, in determining activity (e) the expression of LRP6 and/or FZD6 is determined by determining mRNA level of LRP6 and/or FZD6. In some embodiments, when mRNA level is determined, GAPDH is used as control.

In some embodiments, in determining activity (f), when as compared to control, the presence in the test interferon of activity specified in (f) in a statistically significant manner (such as, p<0.0005, optionally, p<0.0001), signifies that the test interferon and rSIFN-co or rSIFN-co substitute have substantially the same potency and/or are substantial equivalence. In some embodiments, the control is untreated control (Mock).

In some embodiments, the cancer cells employed in determining activity (f), inhibition of expression of any one or more of: Axin2, CD24, Survivin and ID2, comprise lung cancer cells; optionally, comprise A549 cells. In some embodiments, the cancer cells employed in determining activity (f) are treated by the test interferon and/or rSIFN-co or rSIFN-co substitute for at least about 20 hours; optionally, at least about 24 hours. In some embodiments, the cancer cells employed in determining activity (f) are treated by the test interferon and/or rSIFN-co or rSIFN-co substitute in a range of about 5 mcg/ml to about 20 mcg/ml; optionally, about 10 mcg/ml. In some embodiments, in determining activity (f) the expression of Axin2, CD24, Survivin and/or ID2 is determined by determining its corresponding mRNA level. In some embodiments, when mRNA level is determined, GAPDH is used as control.

In some embodiments, in determining activity (f), when the test interferon decreases at least about 30%; optionally, at least about 40%; more optionally, at least about 50%; still more optionally, at least about 60% in expression of any one or more of: Axin2, CD24, Survivin and ID2 in the cancer cells as compared to control, the test interferon and/or rSIFN-co or rSIFN-co substitute are considered to have substantially the same potency and/or substantial equivalence.

In some embodiments, in determining activity (g), when the pseudopod formation in cancer cells is substantially inhibited by the test interferon, signifies that the test interferon and rSIFN-co or rSIFN-co substitute have substantially the same potency and/or are substantial equivalence. For purposes herein, "substantially inhibited" means at least about 60% inhibition; optionally, at least about 70% inhibition; still optionally, at least about 80% inhibition; further optionally, at least about 90% inhibition; still further optionally, at least about 95% inhibition.

In some embodiments, the cancer cells employed in determining activity (g), inhibition of pseudopod formation, comprise lung cancer cells; optionally, A549 cells. In some embodiments, the cancer cells employed in determining activity (g) are treated by the test interferon and/or rSIFN-co or rSIFN-co substitute for at least about 4 days; optionally, at least about 8 days. In some embodiments, the cancer cells employed in determining activity (g) are treated by the test interferon and/or rSIFN-co or rSIFN-co substitute in a range of about 5 mcg/ml to about 20 mcg/ml; optionally, about 10 mcg/ml. In some embodiments, the cancer cells employed in determining activity (g) are cultured in Matrigel.

In some embodiments, in determining activity (h), when the level of beta-catenin in the cancer cells is significantly decreased by the test interferon, signifies that the test interferon and rSIFN-co or rSIFN-co substitute have substantially the same potency and/or are substantial equivalence. For purposes herein, the level of beta-catenin in cancer cells is significantly decreased after treatment when, e.g. on a Western Blot, the band representing the protein becomes faint or absent as compared to that before treatment.

In some embodiments, the cancer cells employed in determining activity (h), inhibition of beta-catenin expression in cancer cells, comprise any one or more of: lung cancer cells and colon cancer cells. In some embodiments, the cancer cells employed in determining activity (h) comprise any one or more of: A549 cells and SW480 cells. In some embodiments, in determining activity (h) the inhibition of beta-catenin expression is determined by Western Blot. In some embodiments, the cancer cells employed in determining activity (h) are treated by the test interferon and/or rSIFN-co or rSIFN-co substitute for at least about 48 hours; optionally, at least about 72 hours. In some embodiments, the cancer cells employed in determining activity (h) are treated by the test interferon and/or rSIFN-co or rSIFN-co substitute in a range of about 5 mcg/ml to about 20 mcg/ml; optionally, about 10 mcg/ml.

In some embodiments, in determining activity (i), when the test interferon can more effective up-regulate the expression of any one or more of: DKK-3, KLF-4, and BATF2 in cancer cells as compared to IFNα-2b, signifies that the test interferon and rSIFN-co or rSIFN-co substitute have substantially the same potency and/or are substantial equivalence.

In some embodiments, the cancer cells employed in determining activity (i), up-regulation of expression of any one or more of: DKK-3, KLF-4, and BATF2 in cancer cells, comprise any one or more of: lung cancer cells, and colon cancer cells. In some embodiments, the cancer cells employed in determining activity (i) comprise any one or more of: A549 cells, H460 cells, SW620 cells, and HT-29 cells; optionally, comprise any one or more of: A549 cells, and SW620 cells. In some embodiments, the cancer cells employed in determining activity (i) are treated by the test interferon and/or rSIFN-co or rSIFN-co substitute for at least about 20 hours; optionally, at least about 24 hours. In some embodiments, the cancer cells employed in determining activity (i) are treated by the test interferon and/or rSIFN-co or rSIFN-co substitute in a range of about 5 mcg/ml to about 20 mcg/ml; optionally, about 10 mcg/ml. In some embodiments, in determining activity (i) the expression of DKK-3, KLF-4 and/or BATF2 is determined by determining its corresponding mRNA level. In some embodiments, when mRNA level is determined, GAPDH is used as control.

In some embodiments, statistical significance means a p value of less than or equal to 0.05, or less than or equal to 0.01, or less than or equal to 0.005, or less than or equal to 0.001, or less than or equal to 0.0005, or less than or equal to 0.0001, when compared to a control.

In some embodiments, the control is not treated with the test interferon or rSIFN-co or rSIFN-co substitute, or is treated with normal saline or PBS, or is treated with IFNα-2b, or the control is untreated control (Mock).

In one aspect, the present invention provides a method of determining or comparing the potency of a compound, such as a test interferon, comprising: (a) providing a plurality of concentrations of the test interferon; (b) determining a first dose response of the test interferon, using the plurality of concentrations of the test interferon, on the viability of a first set of cancer cells under specified conditions; (c) providing a plurality of concentrations of rSIFN-co or a substitute of rSIFN-co (hereafter, "rSIFN-co substitute"); (d) determining a second dose response of the rSIFN-co or rSIFN-co substitute, using the plurality of concentrations of the rSIFN-co or the rSIFN-co substitute, on viability of a second set of cancer cells under the same specified conditions; and (e) comparing the first dose response with the second dose response. In such a manner, the potency of the compound, such as the test interferon, is determined relative to rSIFN-co or rSIFN-co substitute.

In some embodiments of the invention, the rSIFN-co (SEQ ID NO: 1) is made as described in U.S. Pat. No. 7,364,724 (Recombinant Super-Compound Interferon) by expression of the novel polynucleotide (SEQ ID NO:2) in a *E. coli* host, optionally under the control of promoter $P_{BAD}$ in a *E. coli* host. In some embodiments of the invention, the rSIFN-co is obtainable by a process comprising introducing into *E. coli* the polynucleotide sequence shown in SEQ ID NO:2. In some embodiments of the invention, the rSIFN-co has the amino acid sequence of SEQ ID NO: 1, and is encoded by the nucleotide sequence of SEQ ID NO: 2, wherein the interferon has increased inhibitory activities on the expression of hepatitis B surface antigen (HBsAg) and hepatitis B e antigen (HBeAg) of Hepatitis B Virus as compared to an interferon not encoded by the nucleotide sequence of SEQ NO: 2, such as interferon alfacon-1 (INFERGEN®).

In some embodiments, the rSIFN-co used in the methods herein comprises a specified specific activity, and the specific activity can be, for example, in the range between about $4 \times 10^8$ IU/mg to about $1 \times 10^9$ IU/mg. In some embodiments, the specific activity is in the range between about $4.4 \times 10^8$ IU/mg to about $9 \times 10^8$ IU/mg. In some embodiments, the specific activity is in the range between about $5 \times 10^8$ IU/mg to about $8 \times 10^8$ IU/mg. In some embodiments, the specific activity is in the range between about $6 \times 10^8$ IU/mg to about $7.5 \times 10^8$ IU/mg. Optionally, the specific activity is in the range between about $4 \times 10^8$ IU/mg to $5 \times 10^8$ IU/mg.

In some embodiments, in the methods of determining or comparing the potency of a compound, the concentrations of the test interferon or rSIFN-co are in a range between about 0.2 mcg/ml and about 100 mcg/ml. In some embodiments, the concentrations of the test interferon or rSIFN-co are at least two or more of the following: 0.2 mcg/ml, 0.39 mcg/ml, 0.78 mcg/ml, 1.56 mcg/ml, 3.13 mcg/ml, 6.25 mcg/ml, 12.5 mcg/ml, 25 mcg/ml, 50 mcg/ml, and 100 mcg/ml.

In some embodiments, the cells used in the methods herein for determining the effect of rSIFN-co are cancer cells, whether human or animal cells. The cells are treated with the test interferon or rSIFN-co for at least about 24 hr, optionally, at least about 48 hr, and still optionally, at least about 72 hr, and unless otherwise stated, under standard cultural conditions, in complete medium, at 37° C., in a 5% $CO_2$ atmosphere. The culture medium can be any standard complete medium suitable for culture of tumor cells, such as that available from Shanghai Cell Collection (Shanghai, China) and supplemented with 10% fetal bovine serum (Biochrom, Germany), 4 mM glutamine, 50 U/ml penicillin and 50 mcg/ml streptomycin. The IFN alpha-2b may be obtained from Shanghai Hua-xin High Biotechnology, Inc. (Shanghai, China) and rSIFN-co may be obtained from Sichuan Huiyang Life-Engineering Co., Ltd. (Chengdu, China).

In some embodiments, the invention provides rSIFN-co that has the ability to reduce viability of the cancer cells by 50% at a concentration in the range of between about 6.25 mcg/ml and about 25 mcg/ml, depending on the cancer cell type. In some embodiments, the rSIFN-co is capable of reducing viability of the cells by 50% at a concentration in the range of between about 6.25 mcg/ml and 12.5 mcg/ml. In another embodiment, the rSIFN-co is capable of reducing viability of the cells by 50% at a concentration in the range of between about 12.5 mcg/ml and 25 mcg/ml. In some embodiments, the IC50 of the rSIFN-co is in the range of about 10 mcg/ml to about 18 mcg/ml.

In some embodiments, the test interferon is also an interferon, but is obtained from a different manufacturing lot than the rSIFN-co being used in the comparison.

Thus, for example, in determining the potency of a compound such as a test interferon, the test interferon is diluted to various concentrations, and a certain number of prepared cells appropriate for the container being used, such as 5×103 cells in 100 microliter of complete medium, are incubated for a certain period of time with such various concentrations of the test interferon, such as 48 hr. After incubation, the viability of the cells are determined and compared with the viability of cells similarly treated but with rSIFN-co instead of the test interferon. The dose response curves for each of the test interferon-treated and rSIFN-co-treated cells can be generated from the results and compared. In such a manner, the potency of the test interferon, in terms of 50% effective dose or IC50 can be determined relative to that of the rSIFN-co.

In another aspect, the present invention provides a method of determining or comparing potency of a compound, such as a test interferon, relative to rSIFN-co or rSIFN-co substitute, on viability of cancer cells, comprising: (a) providing a plurality of cancer cells; (b) testing a first set of the cancer cells with an amount of the test interferon under specified conditions to generate a first set of viability data; (c) treating a second set of the cancer cells with an effective amount of rSIFN-co or rSIFN-co substitute under the same specified conditions to generate a second set of viability data; and (d) comparing the first set of viability data with the second set of viability data, whereby the potency of the test interferon is determined.

In some embodiments, the cancer cells are treated for a range from about 1 day to about 6 days. In some embodiments, the rSIFN-co is used at a concentration in the range of about 6.25 mcg/ml to about 50 mcg/ml; optionally, about 7 mcg/ml to about 25 mcg/ml; further optionally, about 8 mcg/ml to about 12.5 mcg/ml; still optionally, about 10 mcg/ml. In some embodiments, the rSIFN-co or comprises a specified specific activity.

In some embodiments, the cancer cells used herein are chosen from among human tumor cells and animal tumor cells. In some embodiments, the tumor cells are lung tumor cells, or cervical tumor cells, or liver tumor cells, or colon tumor cells, or breast tumor cells, or pancreatic tumor cells, or prostate tumor cells, or viral-induced tumor cells or virally transformed cells. In some embodiments, the cancer cells are chosen from at least one of: A549 cells, Calu-1 cells, CL-1 cells, H460, H1299, Hela cells, HT29, Huh-7 cells, MDA-MB-231 cells, PANC-1, RAW264.7, SMMC-7721 cells, SW480 cells, and SW620 cells.

Thus, for example, a certain number of cancer cells in an appropriate volume suitable for the test container, such as $2 \times 10^3$ cells in 100 microliter of complete medium, can be placed in 96 well plates and either treated with about 10 mcg/ml of the test interferon or rSIFN-co or left untreated as control, for 1, 2, 3, 4, 5, or 6 days, and the viability of the treated cells determined on each day relative to the viability of the untreated control. At the conclusion of the experiment, the viability of the treated cells relative to that of the untreated control can be plotted against the number of days of interferon treatment. In this way, the ability of the test compound to reduce viability of cancer cells can be compared and its potency determined relative to that of rSIFN-co.

In some embodiments, the present invention provides a method of inhibiting cell migration, such as that occurring in tumor metastases, comprising exposing the cells to an effective amount of rSIFN-co, for a specified period of time, whereby cell migration is inhibited.

In some embodiments, exposure of the cells, such as tumor cells, to rSIFN-co as mentioned herein can be effected in vitro or in vivo, by incubating the cells in the presence of an effective amount of rSIFN-co at 37° C. for a period of time, such as for 24 hr, or by administration of an effective amount of the rSIFN-co to animals or subjects such that a certain concentration of the rSIFN-co is maintained for a period of time sufficient to obtain the desired effect, such as inhibition of tumor cell migration as in metastases, or inhibition of pseudopod formation, inhibition of beta-catenin/TCF transcriptional activity, inhibition of expression of beta-catenin protein, down-regulation of Wnt-related receptors and/or co-receptors, down-regulation of Wnt signaling downstream target genes, up-regulation of tumor suppressor genes, and others as described herein.

The cell migration assay may be performed using any suitable commercially available kits. For example, an 8 micrometer insert containing a microporous membrane placed in a 24-well plate from Becton-Dickinson Biosciences (N.J., USA) can be used herein. For the assay, warm bicarbonate based culture medium at 37° C. without FBS can be added to the interior of the inserts and the bottom of the wells, and allowed to rehydrate for about 2 hr in a humidified tissue culture incubator at 37° C., in 5% $CO_2$ atmosphere. After rehydration, the medium can be carefully removed and about 500 microliter of the prepared cells (such as cells pretreated with rSIFN-co for 24 hr at 37° C.), suspended in FBS-free medium can be seeded onto the upper sides of the insert filters at a density of about $0.5 \times 10^4$ cells/insert. Then 500 microliter of complete medium with 10% FBS can be added to the lower compartment of the 24-well plates. The cells/inserts/plate can then be incubated at 37° C. for about 24 hr, and the non-migrated cells on the upper side of the chamber membranes can be removed, such as with a cotton swab. The lower surfaces of the culture inserts containing the migrated cells can be fixed, such as with 4% paraformaldehyde and stained with 2% crystal violet. The number of migrated cells on the opposite side of the chamber membranes can be counted and the mean number of migrating cells per field determined. In this way, the ability of the test interferon to inhibit tumor cell migration can be demonstrated.

In some embodiments, the effective amount of the rSIFN-co comprises about 5 mcg/ml to about 100 mcg/ml; optionally, about 8 mcg/ml to about 50 mcg/ml; still optionally, about 10 mcg/ml to about 25 mcg/ml; further optionally, about 12 mcg/ml to about 18 mcg/ml.

In another aspect, the invention provides a method of inhibiting pseudopod formation in cancer cells, comprising exposing the cancer cells to an effective amount of rSIFN-co, for a specified period of time, whereby pseudopod formation is inhibited.

In a further aspect, the invention provides a method of inhibiting beta-catenin/TCF-mediated transcriptional activity in cells, comprising exposing the cells to an effective amount of rSIFN-co for a specified period of time.

In some embodiments, the beta-catenin/TCF-mediated transcriptional activity can be determined using a luciferase reporter system. In some embodiments, the reporter system is TOPFlash reporter. In some embodiments, the plasmid pSV40-RL is used. Thus, for example, the cells to be assessed can be plated onto 96-well plates, such as at about $1 \times 10^4$ cells per well, and incubated for about 12 hr at 37° C., after which, they are transiently transfected with about 100 ng of TOPFlash (Millipore Corporation, Billerica, Mass., USA). For normalization of transfection efficiency, the cells can be further co-transfected with 1 ng of internal control reporter *Renilla reniformis* luciferase driven under the SV40 promoter (pRL-SV40) (Promega, Madison, Wis.). After 6 hr of transfection, the cells for in vitro analysis can then be treated with rSIFN-co for about 24 hr. After rSIFN-co treatment for in vitro analysis or after transfection for the in vivo analysis, luciferase assay can be performed using the Dual Luciferase Assay System kit according to the manufacturer's protocols (Cat #: E1960, Promega). Relative luciferase activity can be determined as a ratio of firefly/renilla luciferase activity.

In another aspect, the invention additionally provides a method of decreasing beta-catenin protein level in cells comprising exposing cells to an effective amount of rSIFN-co for a specified period of time. In some embodiments, the protein level of beta-catenin is detected by Western Blot using its specific antibody. In some embodiments, GAPDH is used as a control.

For Western Blot analysis to determine the level of beta-catenin in the cells, cell from in vitro culture or from in vivo tumor samples, standard procedures can be employed. For example, total cellular proteins can be extracted using extraction reagents (Cat #: P0013) following manufacturer's protocol (Beyotime, China). Protein concentrations can be determined with Bio-Rad Lowry protein assay system. Total proteins can be separated by SDS-PAGE on 10%-12% gel and then transferred to a 0.45 micrometer nitrocellulose membrane (Millipore Corporation, Billerica, Mass., USA). The membrane can be blocked with blocking buffer (5% bovine serum albumin, 10 mmol/L Tris-HCl, ph 8.0, 150 mol/L NaCl, and 0.05% Tween 20) overnight at 4° C., then incubated with primary antibodies (1:1000 dilution) followed by secondary HRP-conjugated antibodies. The antibodies can be from any vendor, for example, the following antibodies can be used: mouse monoclonal anti-beta-catenin (1:1000, Santa Cruz Technology, Santa Cruz, Calif.), mouse monoclonal anti-GAPDH (1:2000, Kangwei Biotechnology, China), and anti-mouse HRP-conjugated secondary antibody (1:2000, Santa Cruz Technology). Blots can be visualized using Luminescence/Fluorescence Imaging LAS4000 System (GE Healthcare Life Sciences, USA) with super signal west pico chemiluminescent substrate kit (Thermo Scientific, USA).

In another aspect, the invention provides a method for down-regulating expression of a Wnt-related receptor or co-receptor in cells, comprising exposing the cells to an effective amount of rSIFN-co for a specified time, whereby the Wnt-related receptor or co-receptor is down-regulated. In some embodiments, the Wnt-related receptor or co-receptor comprises a LRP protein, such as LRP6. In some embodiments, the Wnt-signaling receptor or co-receptor comprises a FZD protein, such as FZD6. As stated above, the method of exposing cells to rSIFN-co can be an in vitro method or an in vivo method.

In some embodiments, determining the expression of the Wnt-related receptor or co-receptor comprises determining the mRNA level of such receptor or co-receptor. Such mRNA level can be determined by any standard methods. In some embodiments, cDNA corresponding to such mRNA is made to determine such mRNA levels. For example, total mRNA can be isolated using TRIZOL Reagent (Invitrogen, Carlsbad, Calif.) according to manufacturer's instructions. Complementary DNA (cDNA) can be synthesized using a RT-PCT Kit (Cat #: FSQ-101, TOYOBO, Japan) according to manufacturer's instructions and then subjected to quantitative PCR (qPCR) with a SYBR Green PCR kit (Cat #: QPK-201, TOYOBO, Japan). Suitable primers can be used. For example, the primers for LRP6 can be sense primers: 5'-TGAAGAACCAGCACCACAGG-3' (SEQ ID NO: 4); antisense primers: 5'-CATAACCAAGAGGCACAGAAGC-3' (SEQ ID NO:5), and the primers for FZD6 can be sense primers: 5'-GCGGAGTGAAGGAAGGATTAGTC-3' (SEQ ID NO: 6); and antisense primers: 5'-TGAACAAGCAGA-GATGTGGAACC-3' (SEQ ID NO: 7). The amplification protocol can be incubations at 95° C. for 1 minute, 40 cycles (95° C. for 15 seconds, 60° C. for 15 seconds, and 72° C. for 30 seconds). Incorporation of the SYBR Green dye into the PR products can be monitored in real time with a Bio-Rad Detection System and then analyzed using Bio-Rad CDC manager 2.1 software. The samples can be pooled for each condition and run in duplicated. The interferon-treated samples can be compared with the Mock untreated samples using the $2^{-\Delta\Delta Ct}$ method and plotted as fold change. GAPDH can be used as a normalization control. This $2^{-\Delta\Delta Ct}$ method is conventionally used to analyze relative changes in gene expression from real-time quantitative PCR experiments.

In a further aspect, the invention provides a method of down-regulating the expression of certain genes in cells, including at least one target gene of the Wnt-signaling pathway, such as for the treatment of a disease or condition in which the target gene is mutated or is over-active. Such down-regulated genes include, for example, one or more of Axin2, CD24, Survivin, and/or ID2. The method comprises exposing the cells to an effective amount of rSIFN-co for a specified period of time, whereby expression of the target gene is inhibited. The extent of down-regulated can be determined by standard techniques such as by qPCR as previously mentioned. For example, for such qPCR, for Axin2, the sense primers: 5'-CGTGGATACCTTAGACTT-3' (SEQ ID NO: 8) and the antisense primers: 5'-GCTGT-TGTTCTCAATGTA-3' (SEQ ID NO: 9) can be used; for CD24, the sense primers: 5'-TGAAGAACATGTGAGAG-GTTTGAC-3' (SEQ ID NO: 10) and the antisense primers: 5'-GAAAACTGAATCTCCATTCCACAA-3' (SEQ ID NO: 11) can be used; for Survivin, the sense primers: 5'-ACCG-CATCTCTACATTCAAG-3' (SEQ ID NO: 12) and the antisense primers: -5'CAAGTCTGGCTCGTTCTC-3' (SEQ ID NO: 13) can be used; and for ID2, the sense primers: 5'-CACAACAACAACAACAAC-3' (SEQ ID NO: 14) and antisense primers: 5'-CACAGTCCAAGTAAGAGA-3' (SEQ ID NO: 15) can be used.

In some embodiments of the invention, the specified period of time for exposure of cells to rSIFN-co is at least about 12 hr; optionally, at least about 24 hr; further optionally, for at least about 36 hr; still optionally, at least for about 48 hr; yet still optionally, at least about 72 hr. In some embodiments, the cells being treated by rSIFN-co are cancer cells.

In a further aspect, the invention provides a method of up-regulating expression of certain genes in cells, including at least one tumor suppressor gene, comprising exposing the cells to an effective amount of rSIFN-co for a specified period of time, whereby up-regulation of expression at least one tumor suppressor gene is effected. In some embodiments, the up-regulated gene comprises at least one of DKK3, KLF4, and BATF2. The extent of up-regulation of such genes can be determined by standard techniques. In some embodiments, the expression of the up-regulated gene is determined by measuring mRNA level. In some embodiments, cDNA is synthesized from such mRNA and is optionally amplified for such measurement purposes. As an example, for amplification purposes, the following primers can be used: for BATF2, sense primers: 5'-CAGAGCA-GGGAGCACAAACC-3' (SEQ ID NO: 16) and antisense primers: 5'-TGAGCAGAGGAGAGCAGAGG-3' (SEQ ID NO: 17); for DKK3, sense primers: 5'-GGAGCCTGACT-GAAGAGATGG-3' (SEQ ID NO: 18) and antisense primers: 5'-ACGCCTAAAGCACACACCTG-3' (SEQ ID NO: 19); for KLF4, sense primers: 5'-CCTTCAACCTGGCG-GACATCAAC-3' (SEQ ID NO: 20) and antisense primers: 5'-GGCTGCTGCGGCGGAATG-3' (SEQ ID NO: 21).

In another aspect, the invention provides a method of establishing substantial equivalence between a test compound and rSIFN-co or rSIFN-co substitute in at least one, optionally at least 2, 3, 4, 5, 7, 8 or 9 of the following, comprising comparing the activities thereto and showing substantially the same responses: (a) inhibition of in vivo cancer cell growth in any one or more tumor-bearing animal models; (b) Reduction in cancer cell viability; (c) Inhibition of cancer cell migration; (d) Inhibition of beta-catenin/TCF transcriptional activity in cancer cells; (e) Down-regulation of expression of LRP6 and/or FZD6 in cancer cells; (f) Inhibition of expression of any one or more of: Axin2, CD24, Survivin and ID2 in cancer cells; (g) Inhibition of pseudopod formation in cancer cells; (h) Inhibition of beta-catenin expression in cancer cells; and (i) Up-regulation of expression of any one or more of: DKK-3, KLF-4, and BATF2 in cancer cells. In some embodiments, the invention provides establishing substantial equivalence in at least 2 of the fore-mentioned activities, such as (a) and (b); (a) and (c); (a) and (d); (a) and (e); (a) and (f); (a) and (g); (a) and (h); (a) and (i); (b) and (c); (b) and (d); (b) and (e); (b) and (f); (b) and (g); (b) and (h); (b) and (i); (c) and (d); (c) and (e); (c) and (f); (c) and (g); (c) and (h); (c) and (i); (d) and (e); (d) and (f); (d) and (g); (d) and (h); (d) and (i); (e) and (f); (e) and (g); (e) and (h); (e) and (i); (f) and (g); (f) and (h); (f) and (i); (g) and (h); (g) and (i); (h) and (i); optionally, the invention provides establishing substantial equivalence in at least 3 of the fore-mentioned activities, such as (a), (b) and (c); (a), (b) and (d); (a), (b) and (e); (a), (b) and (f); (a), (b) and (g); (a), (b) and (h); (a), (b) and (i); (a), (c) and (d); (a), (c) and (e); (a), (c) and (f); (a), (c) and (g); (a), (c) and (h); (a), (c) and (i); (a), (d) and (e); (a), (d) and (f); (a), (d) and (g); (a), (d) and (h); (a), (d) and (i); (a), (e) and (f); (a), (e) and (g); (a), (e) and (h); (a), (e) and (i); (a), (f) and (g); (a), (f) and (h); (a), (f) and (i); (a), (g) and (h); (a), (g) and (i); (a), (h) and (i); (b), (c) and (d); (b), (c) and (e); (b), (c) and (f); (b), (c) and (g); (b), (c) and (h); (b), (c) and (i); (b), (d) and (e); (b), (d) and (f); (b), (d) and (g); (b), (d) and (h); (b), (d) and (i); (b), (e) and (f), (b), (e) and (g); (b), (e) and (h); (b), (e) and (i); (b), (f) and (g); (b), (f) and (h); (b), (f) and (i); (b), (g) and (h); (b), (g) and (i); (b), (h) and (i); (c), (d) and (e); (c), (d) and (f); (c), (d) and (g); (c), (d) and (h); (c), (d) and (i); (c), (e) and (f); (c), (e) and (g); (c), (e) and (h); (c), (e) and (i); (c), (f) and (g); (c), (f) and (h); (c), (f) and (i); (c), (g) and (h); (c), (g) and (i); (c), (h) and (i); (d), (e) and (f); (d), (e) and (g); (d), (e) and (h); (d), (e) and (i); (d), (f) and (g); (d), (f) and (h); (d), (f) and (i); (d), (g) and (h); (d), (g) and (i); (d), (h) and (i); (e), (f) and (g); (e), (f) and (h); (e), (f) and (i); (e), (g) and (h); (e), (g) and (i); (e), (h) and (i); (f), (g) and (h); (f), (g) and (i); (g), (h) and (i); optionally, in at least 4 of the fore-mentioned activities, such as (a), (b), (c) and (d); (a), (b), (c), and (e); (a), (b), (c) and (f); (a), (b), (c) and (g); (a), (b), (c) and (h); (a), (b), (c) and (i); (a), (c), (d) and (e); (a), (c), (d) and (f); (a), (c), (d) and (g); (a), (c), (d) and (h); (a), (c), (d) and (i); (a), (d), (e) and (f); (a), (d), (e) and (g); (a), (d), (e) and (h); (a), (d), (e) and (i); (a), (e), (f) and (g); (a), (e), (f) and (h); (a), (e), (f) and (i); (a), (f), (g) and (h); (a), (f), (g) and (i); (a), (g), (h) and (i); (b), (c), (d) and (e); (b), (c), (d) and (f); (b), (c), (d) and (g); (b), (c), (d) and (h); (b), (c), (d) and (i); (b), (d), (e) and (f); (b), (d), (e) and (g); (b), (d), (e) and (h); (b), (d), (e) and (i); (b), (e), (f) and (g); (b), (e), (f) and (h); (b), (e), (f) and (i); (b), (f), (g), and (h); (b), (g), and (i); (b), (g), (h), and (i); (c), (d), (e), and (f); (c), (d), (e), and (g); (c), (d), (e), and (h); (c), (d), (e), and (i); (c), (d), (f) and (g); (c), (d), (f) and (h); (c), (d), (f) and (i); (c), (d), (g), and (h); (c), (d), (g) and (i); (c), (d), (h), and (i); (c), (e), (f) and (g); (c), (e), (f) and (h); (c), (e), (f) and (i); (c), (g) and (h); (c), (g) and (i); (c), (g), (h) and (i); (d), (e), (f) and (g); (d), (e), (f) and (h); (d), (e), (f) and (i); (d), (f), (g) and (h); (d), (f), (g), and (i); (d), (g), (h) and (i); (e), (g) and (h); (e), (f), (g) and (i); (e), (g), (h) and (i); (f), (g), (h) and (i); still optionally, in at least 5 of the fore-mentioned activities, such as (a), (b), (c), (d), and (e); (a), (b), (c), (d), and (f); (a), (b), (c), (d), and (g); (a), (b), (c), (d), and (h); (a), (b), (c), (d), and (i); (a), (c), (d), (e) and (f); (a), (c), (d), (e) and (g); (a), (c), (d), (e) and (h); (a), (c), (d), (e) and (i); (a), (d), (e), (f) and (g); (a), (d), (e), (f) and (h); (a), (d), (e), (f) and (i); (a), (e), (f), (g) and (h); (a), (e), (f), (g) and (i); (a), (f), (g), (h) and (i); (b), (c), (d), (e) and (f); (b), (c), (d), (e) and (g); (b), (c), (d), (e) and (h); (b), (c), (d), (e) and (i); (b), (d), (e), (f) and (g); (b), (d), (e), (f) and (h); (b), (d), (e), (f) and (i); (b), (e), (f), (g) and (h); (b), (e), (f), (g) and (i); (b), (f), (g), (h) and (i); (c), (d), (e), (f) and (g); (c), (d), (e), (f) and (h); (c), (d), (e), (f) and (i); (c), (e), (f), (g), (h) and (i); (d), (e), (f), (g), and (h); (d), (e), (f), (g), and (i); (d), (f), (g), (h) and (i); further optionally, in at least 6 of the fore-mentioned activities, such as (a), (b), (c), (d), (e), and (f); (a), (b), (c), (d), (e), and (g); (a), (b), (c), (d), (e), and (h); (a), (b), (c), (d), (e), and (i); (a), (c), (d), (e), (f), and (g); (a), (c), (d), (e), (f), and (h); (a), (c), (d), (e), (f), and (i); (a), (d), (e), (f), (g) and (h); (a), (d), (e), (f), (g) and (i); (a), (e), (f), (g), (h) and (i); (b), (c), (d), (e), (f), and (g); (b), (c), (d), (e), (f), and (h); (b), (c), (d), (e), (f), and (i); (b), (d), (e), (f), (g) and (h); (b), (d), (e), (f), (g) and (i); (b), (e), (f), (g), (h) and (i); (c), (d), (e), (f), (g), and (h); (c), (d), (e), (f), (g), and (i); (c), (e), (f), (g), (h) and (i); (d), (e), (f), (g), (h) and (i); still further optionally, in at least 7 of the fore-mentioned activities, such as (a), (b), (c), (d), (e), (f), and (g); (a), (b), (c), (d), (e), (f), and (h); (a), (b), (c), (d), (e), (f), and (i); (a), (c), (d), (e), (f), (g) and (h); (a), (c), (d), (e), (f), (g) and (i); (a), (d), (e), (g), (h) and (i); (b), (c), (d), (e), (f), (g) and (h); (b), (c), (d), (e), (f), (g) and (i); (b), (d), (e), (f), (g), (h) and (i); (c), (d), (e), (f), (g), (h) and (i); yet further optionally, in at least 8 of the fore-mentioned activities, such as (a), (b), (c), (d), (e), (f), (g) and (h); (a), (b), (c), (d), (e), (f), (g) and (i); (b), (c), (d), (e), (f), (g), (h) and (i); (a), (c), (d), (e), (g), (h) and (i); (a), (b), (d), (e), (f), (g), (h) and (i); (a), (b), (c), (e), (f), (g), (h) and (i); (a), (b), (c), (d), (f), (g), (h) and (i); (a), (b), (c), (d), (e), (g), (h) and (i); (a), (b), (c), (d), (e), (f), (h) and (i); (a), (b), (c), (d), (e), (f), (g) and (i); or optionally, all 9 of the fore-mentioned activities, such as (a), (b), (c), (d), (e), (f), (g), (h) and (i).

In another aspect, the present invention provides assay kits comprising (a) rSIFN-co or rSIFN-co substitute and (b) at least one of: instructions for performing one or more of the methods described herein and reagents for performing such methods. The reagent may include Phosphate Buffered Saline (PBS) or a buffer. In some embodiments, the rSIFN-co or rSIFN-co substitute in the assay kit comprises a specified specific activity.

In some embodiments, the test interferon also signals through the JAK/STAT signaling pathway in cancer cells and/or shares the common IFNAR1/2 receptor with rSIFN-co, and is, hence, a substantial equivalence of rSIFN-co or has substantially the same potency as rSIFN-co. In some embodiments signaling through the JAK/STAT pathway is detected by means of detecting the presence of phosphorylated proteins from the STAT family, such as STAT1, STAT2 and/or STAT3. In some embodiments, Western Blots are used for such detection. In some embodiments, cancer cells A549 and/or Hela cells can be used for such detection. In some embodiments, the cancer cells are treated with about 10 mcg/ml of the test interferon or the rSIFN-co. In some embodiments the cancer cells are treated with the test interferon or rSIFN-co for about 5, 15, 30, 60, 120, and/or 240 minutes. In some embodiments, after treatment with the interferon, cellular proteins are collected for the Western Blot analysis. In some embodiments, GAPDH is used as a control.

In some embodiments, the tests or activities to be performed to establish equivalence or potency to rSIFN-co or rSIFN-co substitute can be conducted in any conventional manner and are not limited to manner disclosed herein.

EXAMPLES

The invention herein is further illustrated by the following examples, but the examples are not intended to limit the scope of the invention. The invention may be practiced in the presence or absence of any element or elements, limitation or limitations, not specifically mentioned but is recognized to be useful by one of ordinary skill in the art. Further, the descriptions of the invention herein are not intended to be limitations but, unless otherwise specified, should be read to include equivalents or modifications of the features, elements or limitations described, or portions thereof as understood by a person of ordinary skill in the art. It is understood that various other embodiments may be practiced, given the general description provided herein. Other objects, features, and advantages of the invention will become apparent to those skilled in the art from the foregoing, and from the detailed description and examples and appended claims, in conjunction with the accompanying drawings.

All data are displayed as means±standard deviation (SD). T-tests (and nonparametric tests) were applied to analyze the relationship between the different variables. Statistical significance was assumed when p<0.05.

Example 1. Activity of rSIFN-co on Human Hepatoma

This study was conducted to demonstrate the activity and efficacy of rSIFN-co on human hepatoma, using human hepatoma SMMC-7721 as a model, in an in vivo system. The activity of the test article, rSIFN-co, was compared with that of Mitomycin C ("MMC"). rSIFN-co, a colorless liquid, at a concentration of 1 mg/ml, was provided by Huiyang Life Science and Technology Corp. (Chengdu, P.R. China). The test article was used without dilution. It was stored at 4° C. until thawed for injection. Mitomycin C ("MMC"), lot #505 AGB, at a concentration of 2 mg/vial, was provided by Kyowa Hakko Kogyo Co., Ltd. (Japan). MMC was diluted with normal saline at the time of injection.

The animal experiments were operated in accordance with the National Institutes of Health Guide for the Care and Use of Laboratory Animals.

The animals used were 4-6 weeks old male BALB/cA nu/nu mice, weighing about 23±2 g, obtained from the Shanghai Institute of Materia Medica (Shanghai, P.R. China). The study protocol was reviewed by the Committee on the Use and Care of Animals of Shanghai Institute of Materia Medica for compliance with regulations, and Committee approval was obtained prior to study initiation. Wherever possible, procedures used in this study were designed to avoid or minimize discomfort, distress, and pain to the animals. Animals that experience severe or chronic pain or distress that could not be relieved were painlessly euthanized, in accordance to regulations. Animals were housed 6 to a cage. They were ear-marked with ear hole punch identification. The room temperature was maintained at 25° C.±1° C. Lighting was set at 12 hr on and 12 hr off. Food was provided ad libitum. City tap water, filtered with a 5 micrometer (µm) filter, was provided to the animals ad libitum via water bottles. Neither the Study Director nor Huiyang Life Science and Technology Corp. was aware of any contaminant in the food or water that would interfere with or influence the intent and purpose of this study.

The test article (rSIFN-co) and the vehicle control were each administered intratumorally (i.t.). The test article was administered in a volume of 0.05 ml-0.15 ml per mouse per treatment, depending on the group to which the animal was assigned. MMC was administered intravenously (i.v.) at 10 microliter (µl)/g. Normal saline was injected in a volume of 0.15 ml per mouse, which was used as vehicle control.

Animals were assigned to treatment groups randomly. Initially, all animals were placed in one large animal cage. For assignment to the study, they were later separately housed, with 6 animals per cage per treatment group. The dose and dosing regimen for each group were as set forth in Table 1. Groups 1 and 2 are Control groups in which the animals were each administered the vehicle every other day after the first treatment. The animals in Group 3 were given MMC at a dose of 5 mg/kg on days 1 and 6 after initiation of treatment. The animals in Groups 4, 5 and 6 were each given rSIFN-co every other day after the first treatment at 0.15 mg/mouse (Group 4) or 0.10 mg/mouse (Group 5) or 0.05 mg/mouse (Group 6), respectively. Tumor growth was monitored by measuring the length and width of each tumor twice a week during the course of the study. Each animal was also weighed twice a week during the course of the study.

The tumors, human hepatoma SMMC-7721 xenografts, were established in each animal by inoculating $5 \times 10^6$ cells subcutaneously (s.c.) into each mouse. Before commencement of this study, the xenografts were passaged twice in nude mice. Under sterile conditions, well-grown tumors were cut into 1.5 mm$^3$ fragments and one such fragment was injected by trocar needle into the right flank of each study animal. When tumors reached a volume in the range of 100 mm$^3$-200 mm$^3$, the mice were randomized to either control or treated groups and each group received either vehicle (Groups 1 and 2), rSIFN-co (Groups 4, 5 and 6) or MMC (Group 3) at the doses and under the schedule set forth in Table 1, for a period of 3 weeks. Individual tumor size (length and width) was measured twice per week with microcalipers. Tumor volume (V) was calculated using the formula: V=(length×width$^2$)/2. Individual relative tumor volume (RTV) was calculated using the formula: RTV=Vt/V$_0$, where Vt is the tumor volume on the day of measurement and V$_0$ is the tumor volume on the day of first treatment. Therapeutic effect of the test article or control article was expressed in terms of T/C (%), using the formula: T/C (%) (mean RTV of the treated group/mean RTV of the control group)×100%; and in terms of % Inhibition, using the formula: % Inhibition=100%−T/C %.

TABLE 1

Dose Levels and Group Identification for Example 1.

| Group | n | Treatment | Dose | Dosing Schedule |
|---|---|---|---|---|
| 1 | 6 | Vehicle | NA | Every other day |
| 2 | 6 | Vehicle | NA | Every other day |
| 3 | 6 | MMC | 5 mg/kg | d 1 and d 16 |
| 4 | 6 | rSIFN-co | 0.15 mg/mouse | Every other day |
| 5 | 6 | rSIFN-co | 0.10 mg/mouse | Every other day |
| 6 | 6 | rSIFN-co | 0.05 mg/mouse | Every other day |

Results are shown in Table 2 and FIG. 1. Table 2 shows, for each treatment group, the beginning tumor size on day 0, the ending tumor size on day 21, as well as the calculated mean RTV, T/C % and % Inhibition.

TABLE 2

Activity of rSIFN-co on human hepatoma SMMC-7721

| Treatment | TV(mm³, mean ± SD) (D0) | TV(mm³, mean ± SD) (D21) | RTV (mean ± SD) | T/C (%) | % Inhibition | P value |
|---|---|---|---|---|---|---|
| normal saline (12 mice) | 129 ± 26 | 1172 ± 302 | 9.36 ± 3.9 | | | |
| MMC | 125 ± 35 | 621 ± 247 | 5.05 ± 2.1* | 52.82 | 47.18 | p < 0.05 |
| 0.15 mg rSIFN-co | 123 ± 20 | 505 ± 226 | 4.13 ± 1.9** | 43.20 | 56.80 | p < 0.01 |
| 0.10 mg rSIFN-co | 124 ± 15 | 573 ± 287 | 4.57 ± 2.3* | 47.80 | 52.20 | p < 0.05 |
| 0.05 mg rSIFN-co | 124 ± 26 | 592 ± 139 | 4.97 ± 1.7* | 51.99 | 48.01 | p < 0.05 |

Table 2 shows that rSIFN-co was active and effective in inhibiting growth of human hepatoma cells at all the 3 doses tested. The mean RTV on day 21 (D21) was 9.36±3.9 for the Vehicle Control group, 5.05±2.1 for the MMC treated group, 4.13±1.9 for the 0.15 mg rSIFN-co-treated group, 4.57±2.3 for the 0.10 mg rSIFN-co-treated group, and 4.97±1.7 for the 0.05 mg rSIFN-co-treated group. The % Inhibition on day 21 (D21) was: 47.18% for the MMC treated group, 56.80% for the 0.15 mg rSIFN-co-treated group, 52.20% for the 0.10 mg rSIFN-co-treated group, and 48.10 for the 0.05 mg rSIFN-co-treated group. The differences in RTV between each of the treated groups and the Vehicle Control group were determined to be statistically significant.

FIG. 1 shows the progression of growth of human hepatoma, SMMC-7721, in nude mice, as represented by RTV, for each treatment group over the 21-day study period, reflecting the tumor measurements made on days 3, 7, 10, 14, 17 and 21 after the start of treatment. Results show retardation of tumor growth in each of the MMC-treated group and rSIFN-co-treated groups by day 7, which was maintained until day 21. Results also show a trend towards greater inhibition at higher doses of rSIFN-co.

All animals treated with the test article tolerated the tested dosages well with no signs of toxicity or weight loss. The mean body weights (in gram) of the animals for the Vehicle group, the MMC-treated group, the 0.15 mg rSIFN-co-treated group, the 0.10 mg rSIFN-co-treated group, and the 0.05 mg rSIFN-co-treated group were, respectively on day 0 (and day 21): 22.7 (24.8); 23.9 (25.4); 23.7 (25.3); 24.3 (26.2); and 22.6 (24.4).

Example 2. Activity of rSIFN-co on Human Cervical Cancer

This study demonstrates the activity and efficacy of rSIFN-co on treatment of human cervical tumor, using Hela cells as a model. Results show that rSIFN-co was active and effective in inhibiting growth of human cervical cancer cells.

The study was conducted as in Example 1 except as specifically indicated otherwise. Human cervical cancer xenografts were first established and prepared in a similar manner as in Example 1, by inoculating 5×10⁶ Hela cells subcutaneously in nude mice and passaging the well-grown xenografts twice in nude mice. Then 1.5 mm³ fragments were prepared for s.c. implantation into the animals. The body weight of the animals averaged 19±2 g at dose initiation In contrast to Example 1, the animals used were all female. The doses and dosing regimens for each treatment group were similar to those for Example 1, except that MMC was injected on days 1 and 13 after initiation of treatment on day 0 and the study continued over a 28 day period after initiation of treatment.

Figure 2:
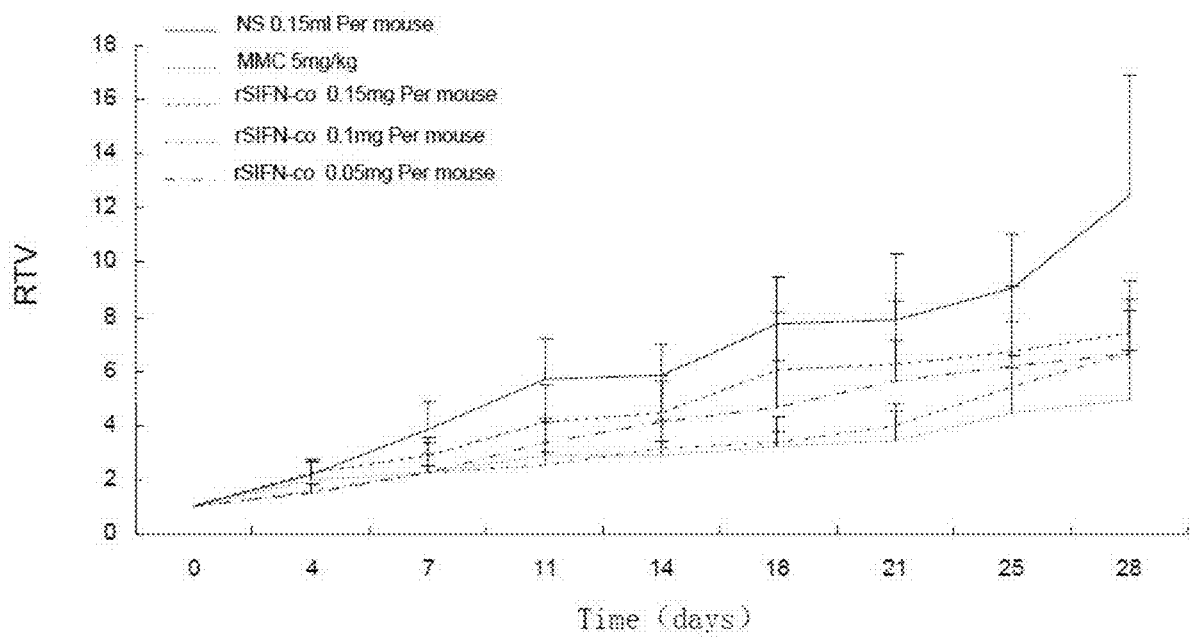
FIG. 2 shows the growth curves of human cervical tumor in nude mice, as described in Example 2, as represented by RTV, for each of the groups treated with either MMC (at 5 mg/kg) or rSIFN-co at 0.15 mg/mouse, 0.10 mg/mouse, or 0.05 mg/mouse, or was injected with vehicle, normal saline (0.15 ml per mouse), over the 28-day treatment period.

Results are shown in Table 3 and FIG. 2. Table 3 shows the calculated mean TVs on day 0 and day 28, as well as the calculated mean RTV, TIC (%) and % Inhibition. The RTV on day 28 (D28) was 12.45±4.46 for the Vehicle Control group, 4.97±1.85 for the MMC treated group, 7.42±1.91 for the 0.15 mg rSIFN-co-treated group, 6.64±2.04 for the 0.10 mg rSIFN-co-treated group, and 6.64±1.60 for the 0.05 mg rSIFN-co-treated group. The Inhibition on day 28 was: 60.08% for the MMC treated group, 40.40% for the 0.15 mg rSIFN-co-treated group, 46.67% for the 0.10 mg rSIFN-co-treated group, and 46.67% for the 0.05 mg rSIFN-co-treated group. The corresponding T/C (%) for the MMC-treated group, the 0.15 mg rSIFN-co-treated group, 0.10 mg rSIFN-co-treated group, and the 0.05 mg rSIFN-co-treated group were: 39.92%, 59.60%, 53.33% and 53.33%, respectively. The differences in RTV between each of the treated groups and the Vehicle Control group were determined to be statistically significant. Results showed that rSIFN-co was effective in inhibiting growth of human cervical cancer in the test animals.

TABLE 3

Activity of rSIFN-co on Human Cervical Cancer Hela Xenografts

| Treatment | TV (mm³, mean ± SD) (D0) | TV (mm³, mean ± SD) (D28) | RTV (mean ± SD) | T/C (%) | % Inhibition | P value |
|---|---|---|---|---|---|---|
| normal saline (12 mice) | 138 ± 25 | 1720 ± 756 | 12.45 ± 4.46 | | | |
| MMC | 130 ± 28 | 676 ± 358 | 4.97 ± 1.85** | 39.92 | 60.08 | p < 0.01 |
| 0.15 mg rSIFN-co | 136 ± 25 | 1025 ± 400 | 7.42 ± 1.91* | 59.60 | 40.40 | p < 0.05 |
| 0.10 mg rSIFN-co | 135 ± 28 | 865 ± 186 | 6.64 ± 2.04** | 53.33 | 46.67 | p < 0.01 |
| 0.05 mg rSIFN-co | 135 ± 26 | 886 ± 232 | 6.64 ± 1.60** | 53.33 | 46.67 | p < 0.01 |

FIG. 2 shows the progression of RTV for each treatment group over the 28-day study period, reflecting the tumor measurements made on days 4, 7, 11, 14, 18, 21, 25 and 28 after the start of treatment. Results showed retardation of human cervical tumor growth in each of the MMC-treated group and rSIFN-co-treated groups by day 7, which was maintained until day 28.

All animals in the study tolerated the rSIFN-co treatments with no signs of toxicity. Very little change in average body weight was observed over the 28-day treatment period.

Example 3. Activity of rSIFN-co on Human Colon Cancer

This study was conducted to demonstrate the activity and efficacy of rSIFN-co on treatment of human colon cancer, using a HT-29 as a model. Results showed that rSIFN-co was active and efficacious in inhibiting the growth of human colon cancer cells. This study was conducted as in Example 1, except as specifically indicated otherwise. Human colon cancer xenografts were first established and prepared in a similar manner as in Example 1, by inoculating 5×10⁶ HT-29 cells subcutaneously into nude mice and passaging the well-grown xenografts twice in nude mice. Then, 1.5 mm³ fragments were prepared for s.c. implantation into the test animals. The body weight of the animals averaged 20±2 g at dose initiation In contrast to Example 1, the animals used in this study were all female. The doses and dosing regimens for each treatment group are as set forth in Example 1 except that MMC was administered to Group 3 on days 1 and 10, and an additional group, Group 7, was added in which each mouse in the group was treated with IFN alpha-2b in a volume of 0.15 ml and at a dose of 0.15 mg/mouse, every other day as in the rSIFN-co-treated groups, and that treatment was carried out for a total of 4 weeks. This IFN-alpha-2b, at a concentration of 1.41 mcg/ml, was provided by Huiyang Life Science and Technology Corp. Results are shown in Table 4 and FIG. 3.

TABLE 4

Activity of rSIFN-co on Human Colon Cancer HT-29 Xenografts

| Treatment | TV (mm³, mean ± SD) (D0) | TV (mm³, mean ± SD) (D28) | RTV (mean ± SD) | T/C (%) | % Inhibition | P value |
|---|---|---|---|---|---|---|
| normal saline (12 mice) | 131 ± 23 | 1107 ± 424 | 8.41 ± 2.82 | | | |
| MMC (5 mg/kg) | 132 ± 22 | 395 ± 95 | 3.12 ± 1.19*** | 37.10 | 62.9 | p < 0.001 |
| rSIFN-co 0.15 mg | 131 ± 36 | 570 ± 144 | 4.51 ± 1.25** | 53.63 | 46.37 | p < 0.01 |
| rSIFN-co 0.10 mg | 128 ± 39 | 541 ± 196 | 4.22 ± 0.87** | 50.18 | 49.82 | p < 0.01 |
| rSIFN-co 0.05 mg | 130 ± 26 | 416 ± 166 | 3.28 ± 1.25*** | 39 | 61 | p < 0.001 |
| IFNalpha-2b 0.15 mg | 128 ± 44 | 831 ± 420 | 6.26 ± 1.43 | 74.44 | 25.56 | p > 0.05 |

Table 4 shows the calculated beginning mean TV on day 0 and the ending mean TV on day 28, as well as the calculated mean RTV, TIC (%) and % Inhibition. The RTV on day 28 (D28) was 8.41±2.82 for the Vehicle Control group, 3.12±1.19 for the MMC treated group, 4.51±1.25 for the 0.15 mg rSIFN-co-treated group, 4.22±0.87 for the 0.10 mg rSIFN-co-treated group, 3.28±1.25 for the 0.05 mg rSIFN-co-treated group, and 6.26±1.43 for the IFN alpha-2b-treated group. The % Inhibition on day 28 was: 62.9% for the MMC treated group, 46.37% for the 0.15 mg rSIFN-co-treated group, 49.82% for the 0.10 mg rSIFN-co-treated group, 61% for the 0.05 mg rSIFN-co-treated group, and 25.56% for the IFN alpha-2b-treated group. The corresponding TIC (%) for the MMC-treated group, the 0.15 mg rSIFN-co-treated group, 0.10 mg rSIFN-co-treated group, the 0.05 mg rSIFN-co-treated group, and the IFN alpha2b-treated group were: 37.10%, 53.63%, 50.18%, 39.00% and 74.44%, respectively. Results showed that rSIFN-co was more effective than IFN alpha-2b in inhibiting growth of human colon cancer cells. The differences in RTV between each of the treated groups and the Vehicle Control group were determined to be statistically significant.

Figure 3:
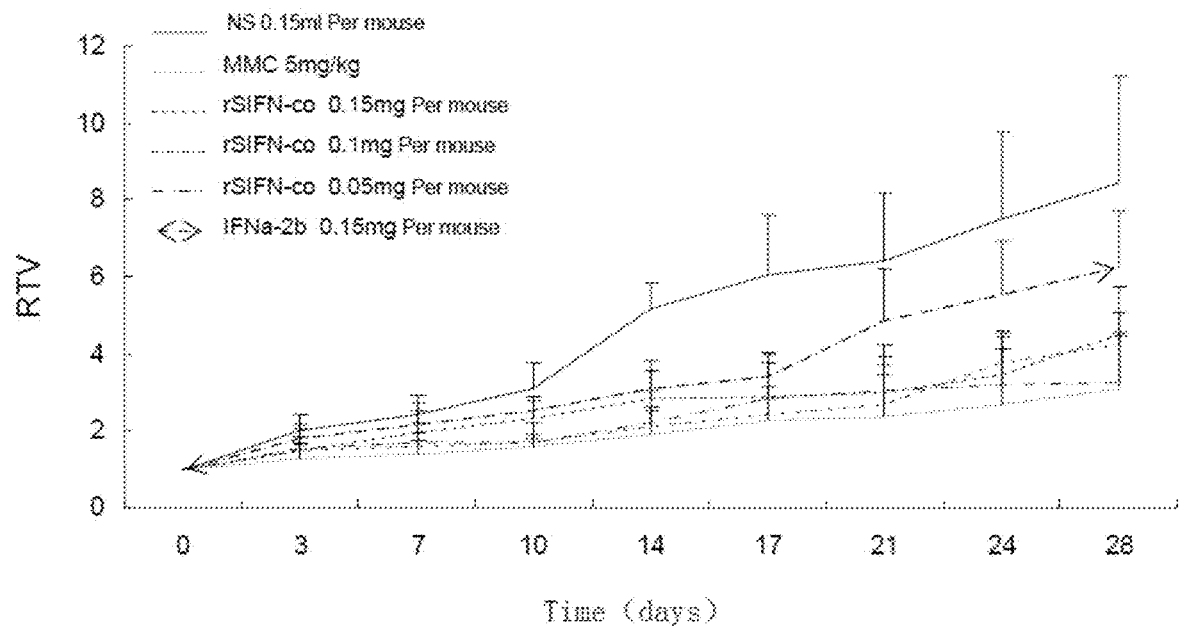
FIG. 3 shows the growth curves of human colon tumor, HT-29, in nude mice, as described in Example 3, as represented by RTV for each of the groups treated with either MMC (at 5 mg/kg) or rSIFN-co at 0.15 mg/mouse, 0.10 mg/mouse, or 0.05 mg/mouse, or IFNalpha-2b at 0.15 mg/mouse, or was injected with vehicle, normal saline (0.15 ml per mouse), over the 28-day treatment period.

FIG. 3 shows the inhibition of growth of human colon tumor, as represented by RTV for each of the treatment groups over the 28-day study period, reflecting the tumor measurements made on days 3, 7, 10, 14, 17, 21, 24 and 28, after the start of treatment. Results showed retardation of human colon tumor growth in each of the MMC-treated group and the rSIFN-co-treated groups by day 7, which was maintained until day 28. Each of the 3 doses of rSIFN-co caused more inhibition of tumor growth than IFN alpha-2b.

As in Examples 1 and 2, all rSIFN-co-treated animals tolerated the tested dosages and showed no signs of drug toxicity and minimal changes in weight.

Example 4. Activity of rSIFN-co on Human Lung Cancer

This study was conducted to demonstrate the activity and efficacy of rSIFN-co on treatment of human lung cancer, using a SPC-A4 as a model. Results showed significant inhibition of human lung tumor growth by rSIFN-co and that rSIFN-co was much more effective than IFN alpha-2b. The study was conducted as in Example 3, except as specifically indicated otherwise. Human xenografts for injection into the test animals were first established and prepared in a similar manner as in Example 1, but by inoculating $2.5 \times 10^6$ SPC-A4 cells subcutaneously (s.c.) in nude mice and passaging the well-grown tumors twice in nude mice. The 1.5 mm$^3$ fragments were then used for s.c. implantation into the test animals. The body weight of the animals averaged 22±2 g at dose initiation. In contrast to Example 3, the animals used in this study were all male and the study was conducted over a 21 day treatment period. The doses and dosing regimens for each treatment group are as set forth in Example 3 except that MMC was administered to Group 3 on days 1 and 6. Results are shown in Table 5 and FIG. 4.

TABLE 5

Effect of rSIFN-co on growth of human lung cancer SPC-A4 xenografts in nude mice.

| Treatment | TV (mm$^3$, mean ± SD) (D0) | TV (mm$^3$, mean ± SD) (D21) | RTV (mean ± SD) | T/C (%) | % Inhibition | P value |
|---|---|---|---|---|---|---|
| normal saline (12 mice) | 168 ± 42 | 7133 ± 2708 | 42.54 ± 2.82 | | | |
| MMC (5 mg/kg) | 166 ± 42 | 1831 ± 540 | 11.54 ± 4.37*** | 27.13 | 72.87 | p < 0.001 |
| rSIFN-co 0.15 mg | 169 ± 40 | 2284 ± 653 | 13.72 ± 3.96** | 32.25 | 67.75 | p < 0.01 |
| rSIFN-co 0.10 mg | 168 ± 49 | 2388 ± 1544 | 14.91 ± 11.19** | 35.05 | 64.95 | p < 0.01 |
| rSIFN-co 0.05 mg | 170 ± 41 | 2244 ± 1043 | 15.45 ± 9.07** | 36.32 | 63.68 | p < 0.01 |
| IFNalpha-2b 0.15 mg | 191 ± 44 | 4908 ± 2433 | 27.84 ± 15.51 | 65.47 | 34.53 | p > 0.05 |

Figure 4:
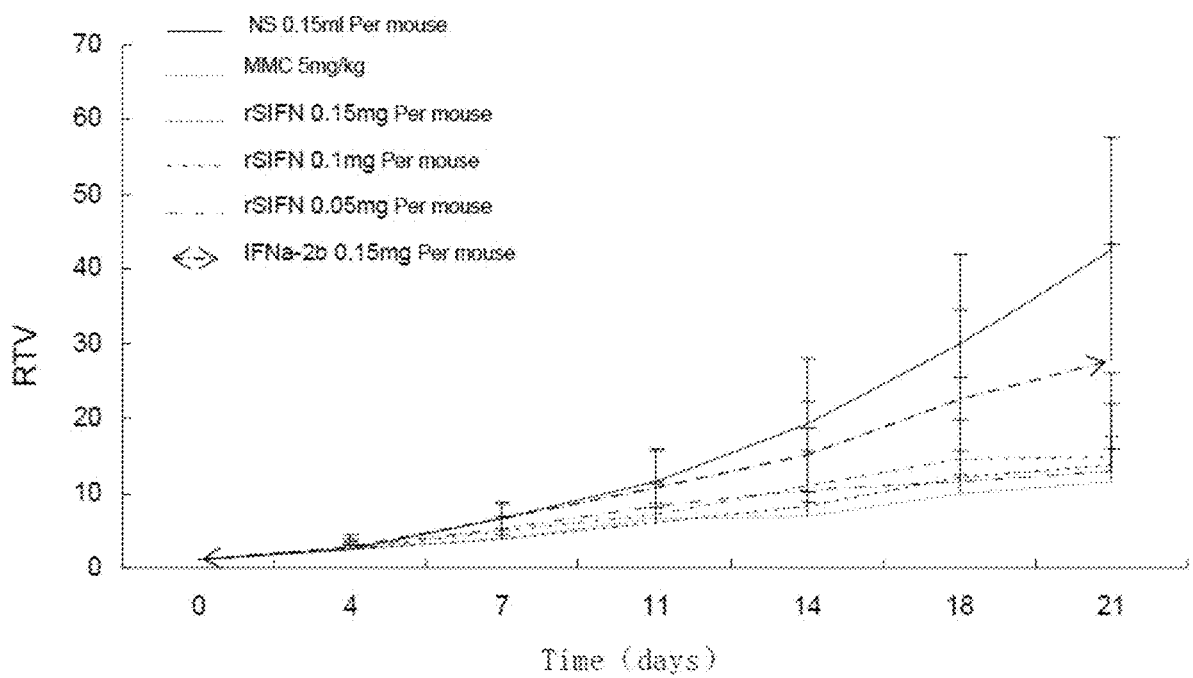
FIG. 4 shows the growth curves of human lung tumor, SPC-A4, in nude mice, as described in Example 4, as represented by RTV for each of the groups treated with either MMC (at 5 mg/kg) or rSIFN-co at 0.15 mg/mouse, 0.10 mg/mouse, or 0.05 mg/mouse, or IFNalpha-2b at 0.15 mg/mouse, or was injected with vehicle, normal saline (0.15 ml per mouse), over the 21-day treatment period.
Figure 5A:
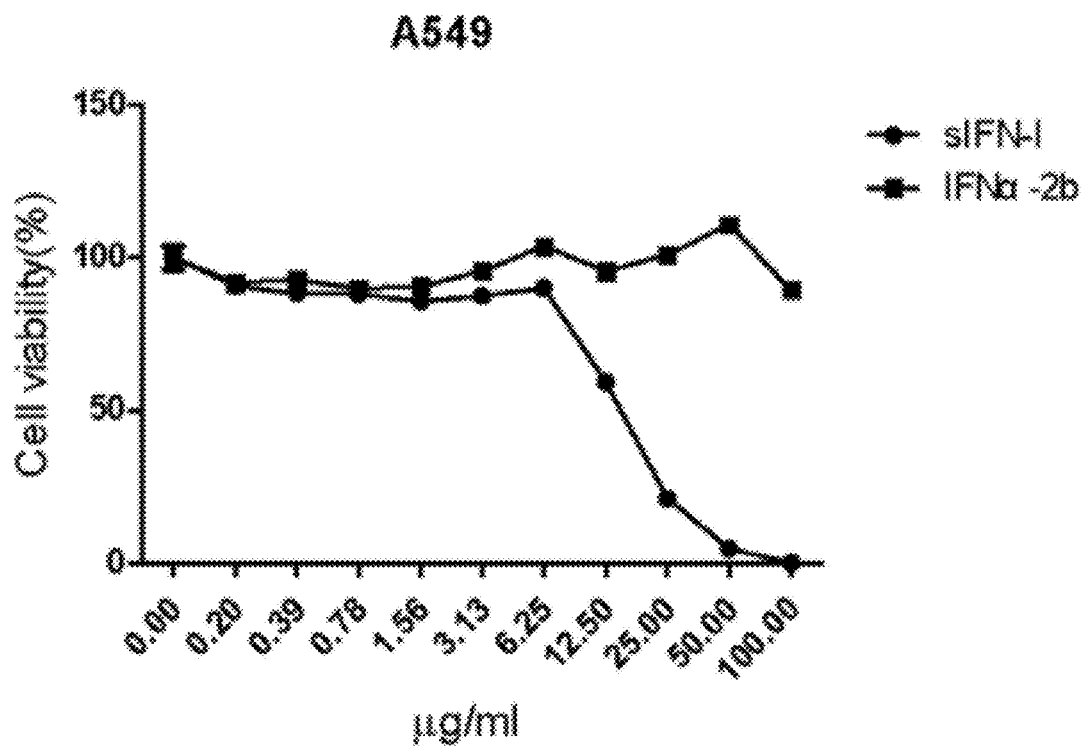
FIG. 5 shows dose response curves on the viability of different tumor cells after treatment for 48 hr with either rSIFN-co or IFN alpha-2b (IFNα-2b) at the concentrations indicated in mcg/ml (μg/ml): 0, 0.2, 0.39, 0.78, 1.56, 3.13, 6.25, 12.50, 25, 50, and 100. The cells tested were: A549 lung tumor cells (FIG. 5A); Hela cervical tumor cells (FIG. 5B); CL-1 liver tumor cells (FIG. 5C); Huh-7 liver tumor cells (FIG. 5D); SW480 colon tumor cells (FIG. 5E); MDA-MB-231 breast tumor cells (FIG. 5F); Calu-1 lung tumor cells (FIG. 5G); SMMC-7721 liver tumor cells (FIG. 5H); and PANC-1 pancreatic tumor cells (FIG. 5I). Results are expressed as a percentage of cell viability relative to control cells, and represent the mean of at least two independent experiments.
Figure 5B:
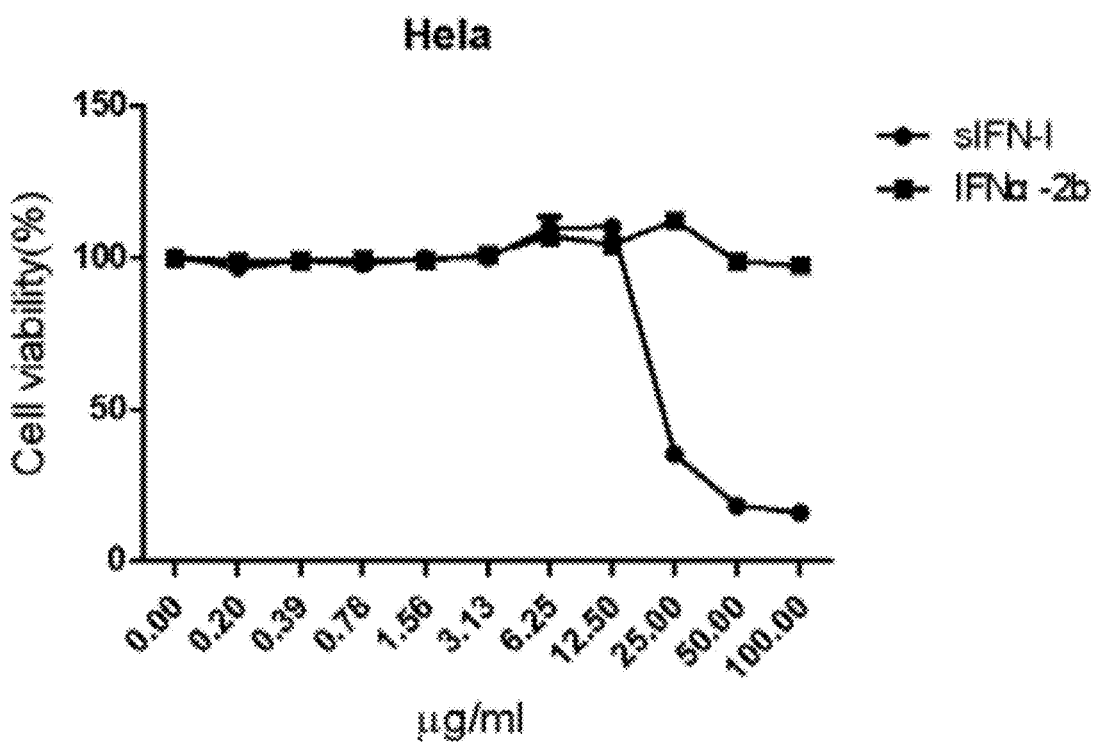
Figure 5C:
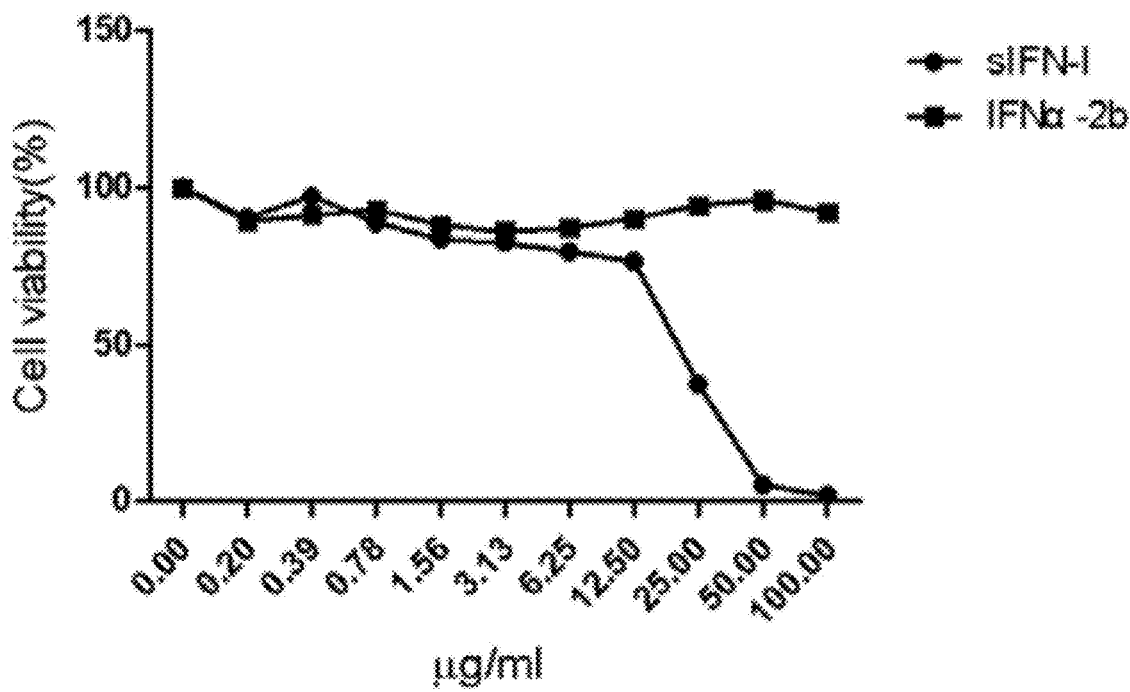
Figure 5D:
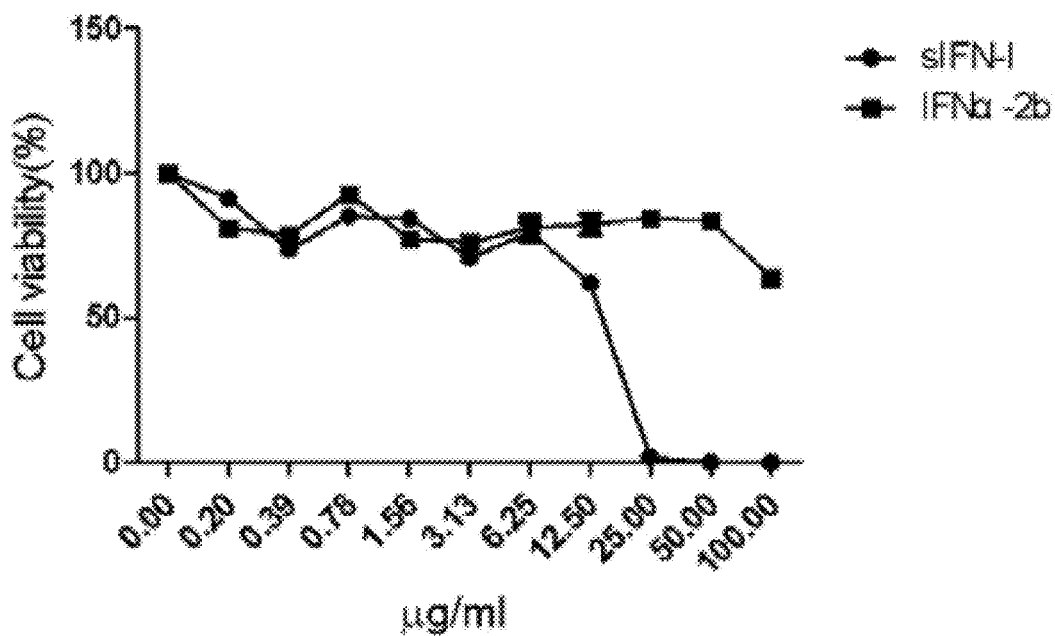
Figure 5E:
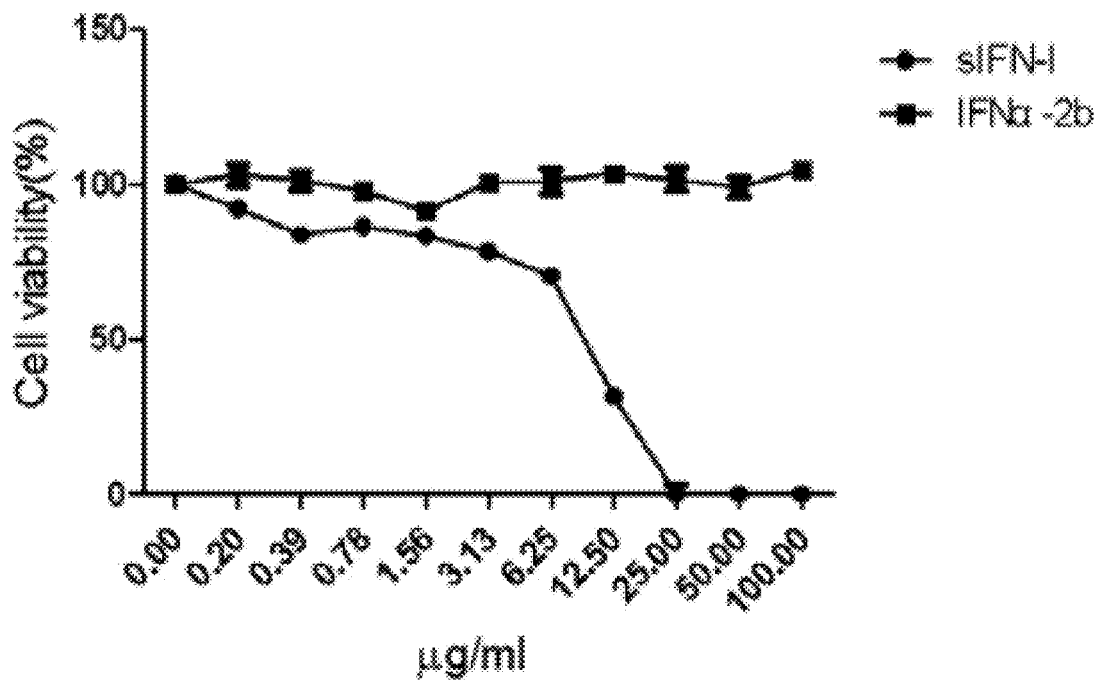
Figure 5F:
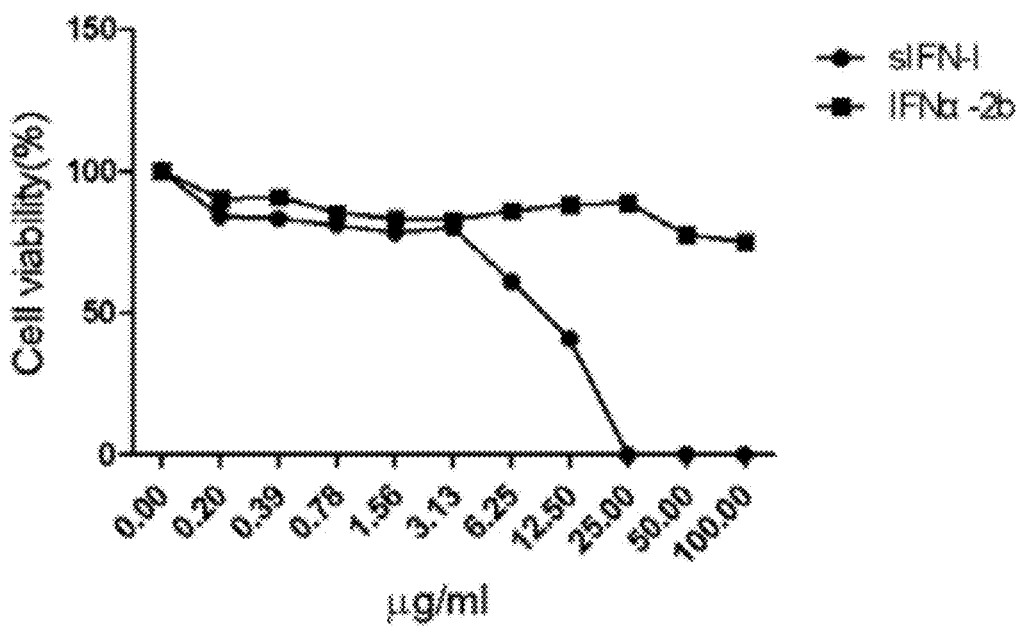
Figure 5G:
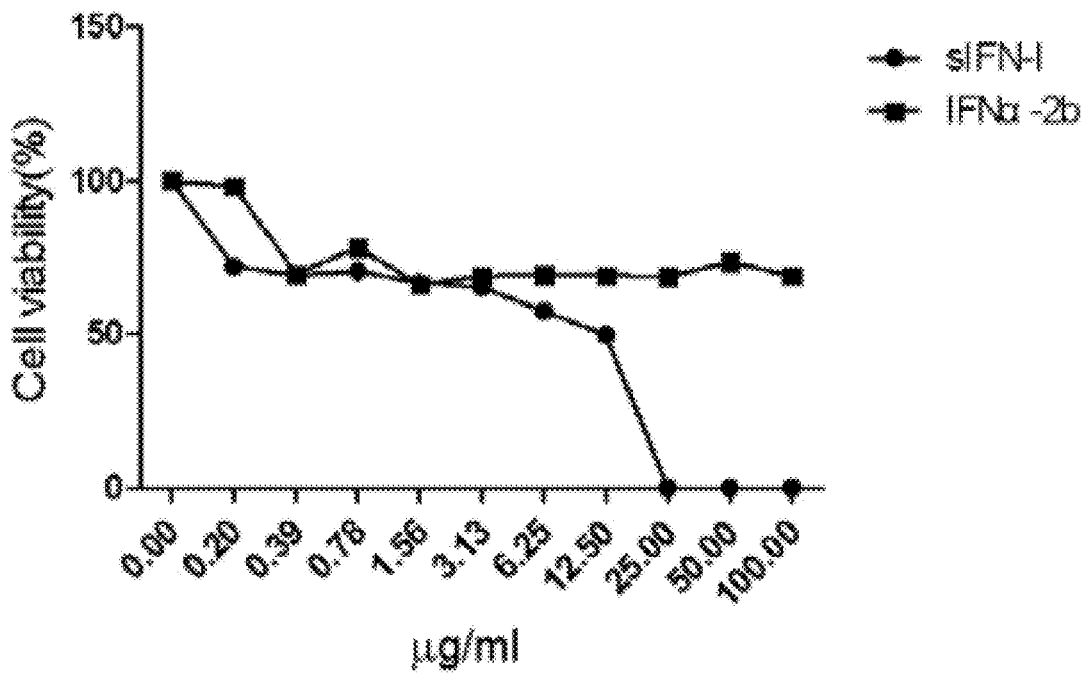
Figure 5H:
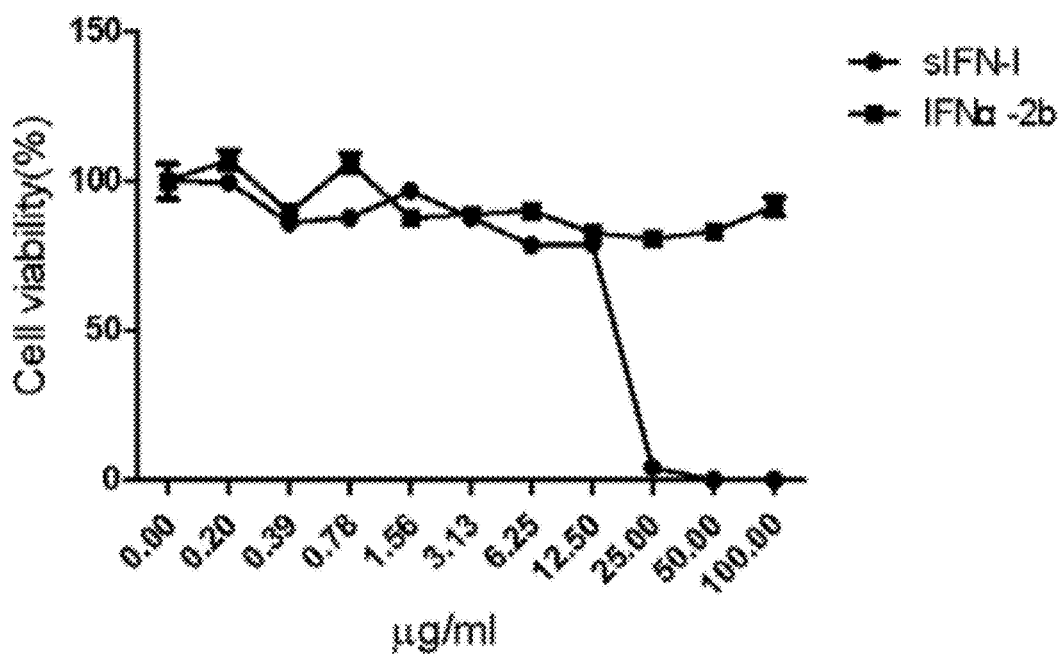
Figure 5I:
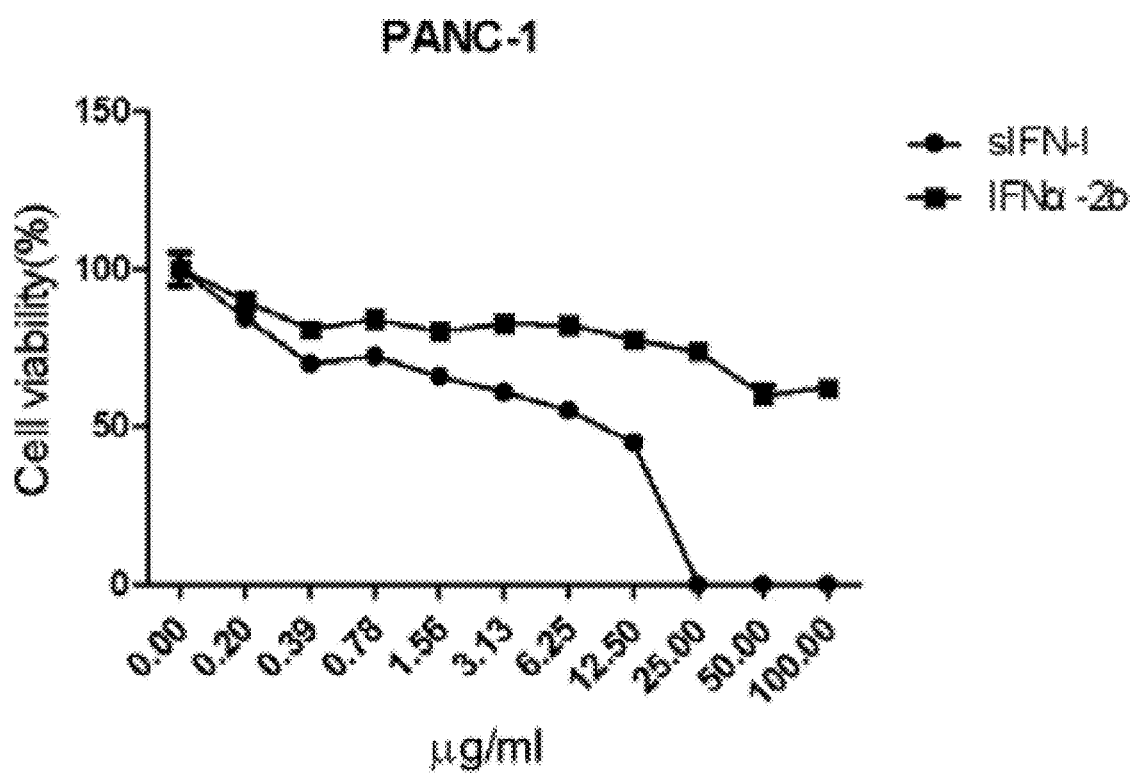

FIG. 4 shows the inhibition of growth of human lung tumor in nude mice, as represented by RTV for each of the treatment groups over the 21-day study period, reflecting the tumor measurements made on days 4, 7, 11, 14, 18, and 21, after the start of treatment. Results showed retardation of tumor growth in each of the MMC-treated group and rSIFN-co-treated groups by day 7, which was maintained until day 21 when the study ended. Tumor inhibition was not seen with the IFN alpha-2b treated group until day 11. Inhibition of tumor growth by IFN alpha-2b was less than that by any of the rSIFN-co-treated groups and was not statistically significant (p>0.05). Hence, rSIFN-co was more effective in inhibiting growth of human lung cancer cells than IFN alpha-2b.

As in Examples 1-3, all animals tolerated the tested dosages of test articles and no signs of toxicity or weight loss were observed, except that one mouse in the 0.05 mg rSIFN-co-treated group died on day 17, for reasons unknown.

Example 5. rSIFN-co Reduced Viability of Various Human Solid Cancer Cells

Cell culture and reagents human lung cancer cell lines (A549, H1299, H460, Calu-1), human liver cancer cell lines (SMMC-7721, Huh-7, CL-1), human cervical carcinoma cell line (Hela), human breast cancer cell line (MDA-MB-231), human pancreatic cancer cell line (PANC-1) and human colon cancer cell lines (SW620, HT29, SW480) were purchased from the Shanghai Cell Collection (Shanghai, China). The above cell lines were cultured in 5% $CO_2$ at 37° C. in corresponding complete growth medium formulated by the Shanghai Cell Collection, with 10% heat-inactivated fetal bovine serum (Biochrom, Germany), supplemented with 4 mM glutamine, 50 U/ml penicillin and 50 mg/ml streptomycin. The complete growth media were: F-12K (lot # GNM21127; Hangzhou Gino Bio-Medical Technology Ltd.) for A549; L-1.5 (lot #41300-039, GIBCO) for SW620 and MDA-MB-231; DMEM (lot # C11995, GIBCO) for SMMC-7721, Hela, Huh-7, CL-1, and PANC-1; RMPI-1640 (lot # C11875, GIBCO) for H460, H1299, and SW480; Macro5a (lot # M4892, Sigma) for HT-29; and DMEM+ 10% FBS for Calu-1.

About $5 \times 10^3$ cells in 100 μl complete medium per well were plated in 96-well plates, incubated overnight, and then treated with IFN α-2b or rSIFN-co at concentrations of 100 μg/ml, 50 μg/ml, 25 μg/ml, 12.5 μg/ml, 6.25 μg/ml, 3.13 μg/ml, 1.56 μg/ml, 0.78 μg/ml, 0.39 μg/ml, and 0.20 μg/ml, respectively, for about 48 hr, at which time the cells were harvested for analysis. The cell viability rate was evaluated by SunBio Am-Blue assay kit (Cat #: SBAB8025, Shanghai SBO Medical Biotechnology Co., Ltd, Shanghai, China). According to its protocol, 10 μl Am-Blue was added to each well. Then the cells were incubated in 5% $CO_2$ at 37° C. for 4 hours. After shaking the plates for 30 seconds, the absorbance for each well was read at both 570 nm and 595 nm by a Thermo Scientific Microplate Reader (Thermon Fisher Scientific, Inc., Lowell, Mass.), The relative cell viability was calculated as follows: Cell viability=(Treated Group$_{(OD570-OD595)}$ minus Blank$_{(OD570-OD595)}$)/(Control group$_{(OD570-OD595)}$ minus Blank$_{(OD570-OD595)}$)×100%, where the Control group was the corresponding untreated cells. Results are shown in FIG. 5, in which viability of the tumor cells was expressed as a percentage relative to control cells that were not treated. Each data point represented the mean of at least two independent experiments.

FIG. 5 shows the dose response curve for each cancer cell line, (A) through (I), treated with either rSIFN-co or IFNα-2b in reducing the viability of the cancer cells. (A) A549 cells; (B) Hela cells; (C) CL-1 cells; (D) Huh-7 cells; (E) SW480 cells; (F) MDA-MB-231 cells; (G) Calu-1 cells; (H) SMMC-7721 cells; (I) PANC-1 cells.

Results showed that IFNα-2b even at the highest concentration tested (100 μg/ml) had no or very little effect in reducing the viability of A549 cells, Hela cells, CL-1 cells, SW480 cells, and SMMC-7721 cells. Less than 50% reduction in viability was seen when IFNα-2b at 100 mcg/ml (μg/ml) was used to treat Huh-7 cells, MDA-MB-231 cells, Calu-1 cells, and PANC-1 cells. In contrast, rSIFN-co was able to reduce tumor cells viability in a dose dependent manner at much lower doses, with close to 50% reduction in cell viability at concentrations between 6.25 μg/ml and 12.5 μg/ml for SW480 cells, MDA-MB-231 cells, and PANC-1 cells and between 12.5 μg/ml and 25 μg/ml for A549 cell, Hela cells, CL-1 cells, Huh-7 cells, Calu-1 cells, and SMMC-7721 cells. Generally, $IC_{50}$ for rSIFN-co in decreasing cell viability was in a range of about 10 mcg/ml to 18 mcg/ml for different, cancer cells. At 100 mcg/ml of rSIFN-co, cell viability could not be detected for any of the cancer cell lines. Thus, rSIFN-co was more effective in reducing tumor cell viability than IFN alpha-2b at each of the concentrations tested.

Example 6A. rSIFN-co was More Effective in Effective in Reducing Cell Viability than IFN Alpha-2b To demonstrate the ability of rSIFN-co to reduce cell viability, A549 and SW620 tumor cells, each at $2 \times 10^3$ in 100 μl of complete medium per well were plated onto 96-well plates, and treated with 10 μg/ml of rSIFN-co or IFN alpha-2b, respectively, for 1-6 days. The cell survival rate was evaluated in a standard MTT assay (3-(4,5-dimethyl-thiazol-2-yl)-2,5-diphenyltetrazolium bromide assay, Sigma, St. Louis, Mo.). For the assay, about 20 μl MTT (at 4 mcg/ml) was added to each well. The cells were incubated at 37° C. for 4 hr. After that, the supernatant of each well was drawn off carefully and then an equal volume (150 microliter) of dimethyl sulfoxide (DMSO) was added to each well and mixed thoroughly on a shaker for 15 min. The absorbance from the plates was read at 595 nm with a Thermo Scientific Microplate Reader (Thermo Fisher Scientific Inc., Lowell, Mass.). The relative cell viability was calculated as follows: Cell viability=(Treated group$_{(OD595)}$ minus blank$_{(OD595)}$)/(Control group$_{(OD595)}$ minus blank$_{(OD595)}$)× 100%.

Figure 6:
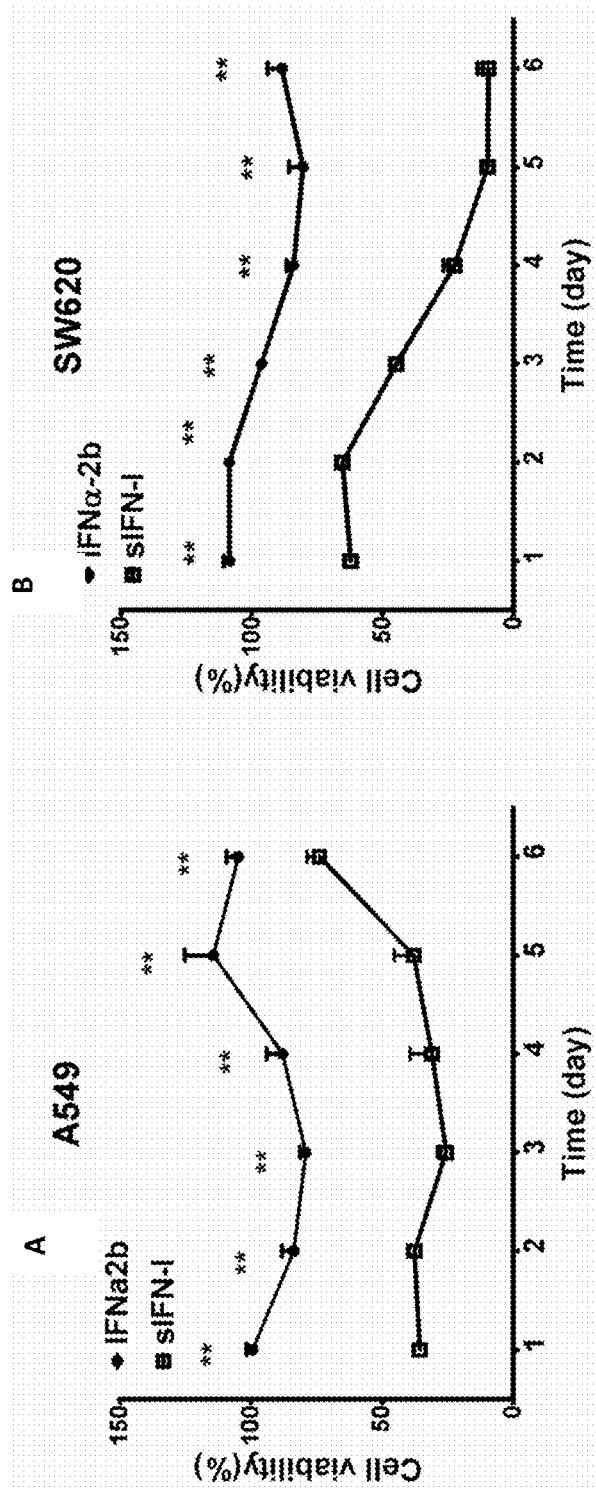
FIG. 6 are viability curves showing the effect of IFN alpha-2b treatment and rSIFN-co treatment, respectively, at 10 mcg/ml, on the viability of A549 cells (FIG. 6A) and SW620 (FIG. 6B) cells after treatment for the indicated number of days: 1, 2, 3, 4, 5, and 6. Cell viability was evaluated by the MTT assay. Results are expressed as percentage cell viability relative to control cells and represent the mean of at least 2 independent experiments. (**$p<0.01$).

Results are expressed as a percentage relative to untreated control cells. Each data point represents the mean of at least two (2) independent experiments. As shown in FIG. 6, rSIFN-co strongly decreased cell viability of SW620 cells in a time-dependent manner in contrast to IFN alpha-2b, which had little time-dependent effect, if any. The time dependent effect of rSIFN-co was also apparent for A549 cells for only about the first 3 days of treatment. The difference in effect between rSIFN-co and IFN alpha-2b at each time point for each cell line was statistically significant (p<0.01). These data showed a strong anti-tumor effect of rSIFN-co in a time-dependent manner.

Example 6B. rSIFN-co Inhibited Tumor Growth In Vivo

Figure 16:
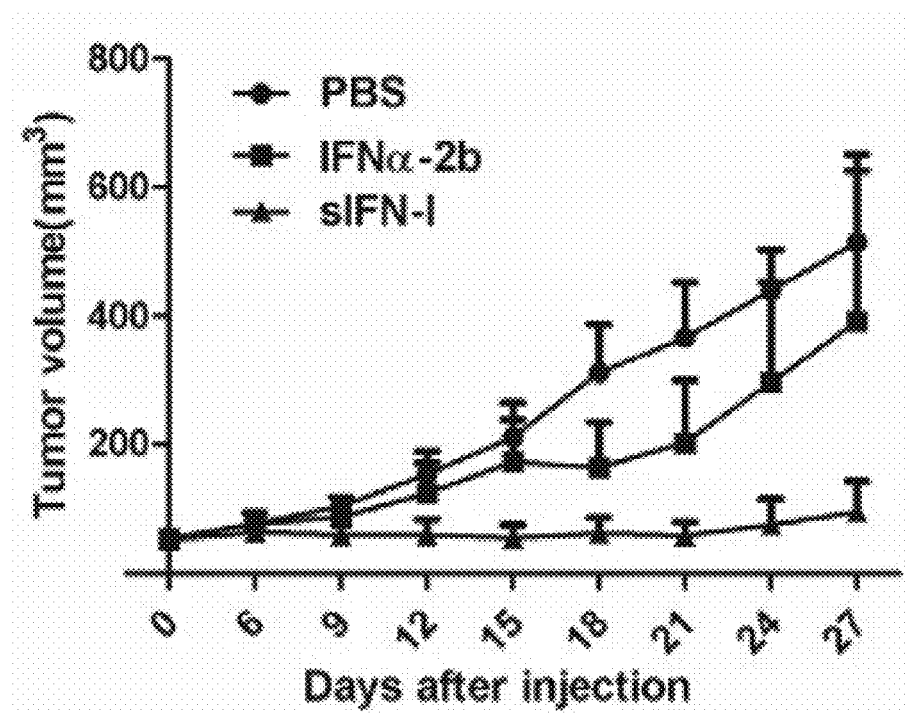
FIG. 16 is a tumor growth curve showing the inhibition of tumor growth after treatment by either IFN alpha-2b or rSIFN-co as compared to PBS-treated controls over a period of 27 days after initiation of treatment. Data are presented as mean tumor volume (mm$^3$)±SD (n=8).

This experiment was conducted in accordance to the National Institutes of Health Guide for the Care and Use of Laboratory Animals. Female BALB/c nude mice, 4-5 weeks old, were obtained from Shanghai Experimental Animal Center (Shanghai, China). About $5 \times 10^6$ A549 cells were subcutaneously injected into each mouse to establish xenograft tumors. The animals were divided into three (3) groups at random (8 mice per group), and treated with PBS (1×PBS, pH 7.2-7.4), rSIFN-co at 100 μg/100 μl per mouse or with IFNα-2b, also at 100 μg/100 μl per mouse, intratumorally, every other day, for 12 times. The tumors were measured every three (3) days and the tumor volumes were calculated as follows: tumor volume (mm$^3$)=(length×width$^2$)/2. The results are shown in FIG. 16. Data are shown as Mean±SD (n=8). Results demonstrate that rSIFN-co could almost completely inhibit growth of established tumors as compared to the PBS-treated group (p<0.0001). However, IFNα-2b did not exhibit remarkable suppression of tumor growth. Results indicated that rSIFN-co was more effective than IFNα-2b in inhibiting tumor growth in vivo.

Example 6C. rSIFN-co Inhibited Colony Formation and Invasive Feet Formation (Pseudopod Formation) by Tumor Cells in Three Dimensional Culture Systems Matrigel (from BD Corporation, Cat #: 356234) was thawed on ice in a 4° C. refrigerator overnight, and a 24-well plate was frozen at −20° C. overnight. Thereafter, each well of the frozen 24-well plate was coated with 150 μl of the Matrigel at 1.0 mcg/ml. The Matrigel coated plate was then incubated 37° C. for 20-30 min. Lung cancer cells, A549, were trypsinized and counted. About $5 \times 10^3$ cells in conditioned medium containing 2% Matrigel, and either 10 mcg/ml of IFN alpha-2b or rSIFN-co, or with no interferons as control were seeded on the Matrigel coated wells. The cells were incubated at 37° C. for at least about 8 days. About 200 μl of the above conditioned medium was added every 3 days to prevent the medium from drying. On the $4^{th}$ or $8^{th}$ day, photographs were taken to observe the size of the colonies and invasive feet (pseudopod) formation. The experiment was conducted in triplicate.

Figure 7:
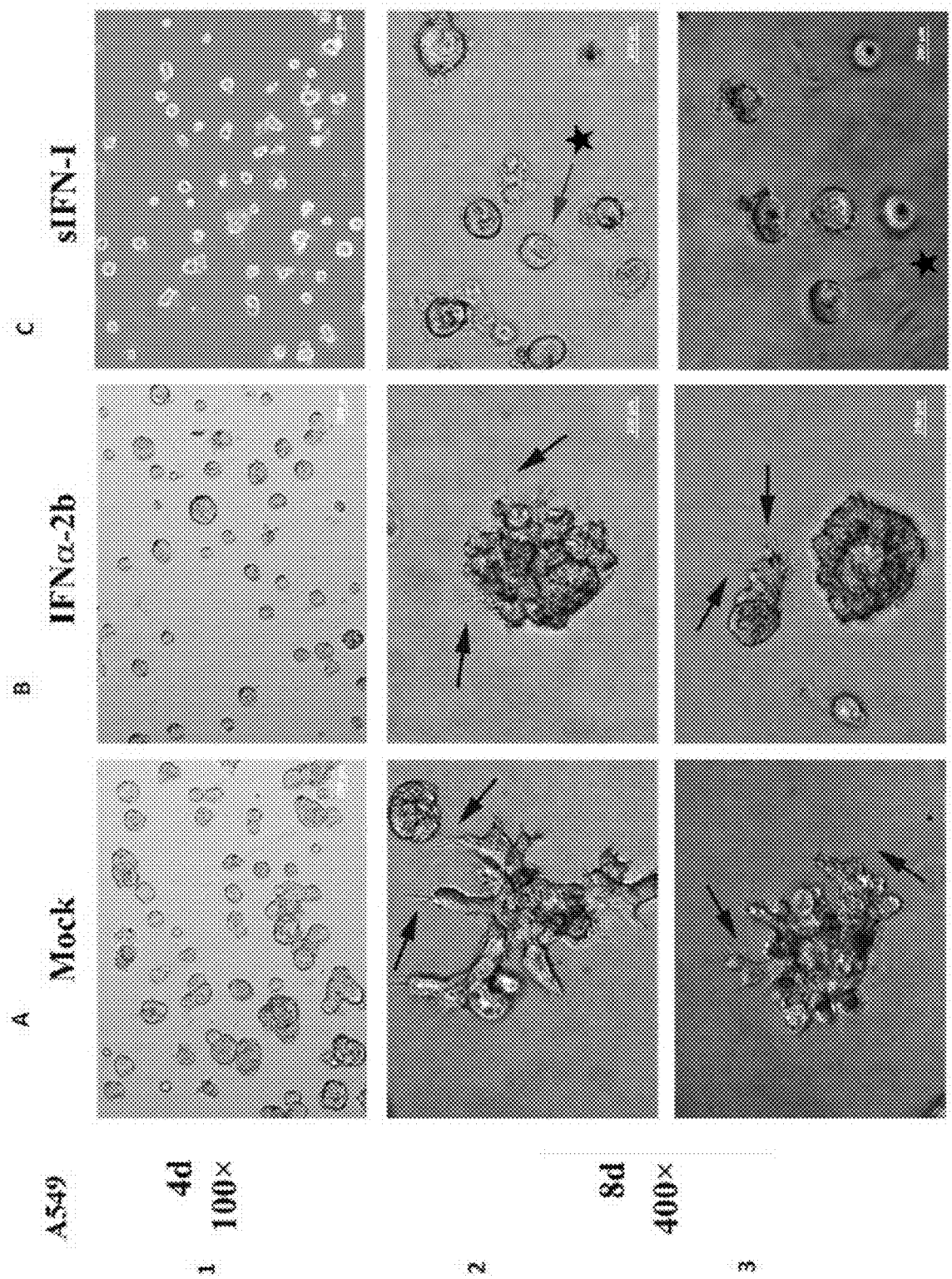
FIG. 7 are photomicrographs showing the effect of rSIFN-co treatment (FIG. 7, column C) and IFN alpha-2b treatment (FIG. 7, column B), respectively, as compared to Mock control (FIG. 7, column A) on lung cancer cells, A549, on colony formation after 4 days (row 1) (magnified 100×) and invasive feet (pseudopods) formation after 8 days (rows 2 and 3)(magnified 400×), in 3D culture. Black arrows in columns A and B point to pseudopods protruding from the cancer cells. Arrows with a star in column C point to cells without pseudopod.

Results are shown in FIG. 7. After 4 days, rSIFN-co treated group (FIG. 7C) was found to have the smaller colonies than the untreated group (FIG. 7A). After 8 days, the rSIFN-co-treated group not only had the smallest colonies of the 3 groups, it was found that there was almost no extrusive pseudopodium around the cells (FIG. 7C, rows 2 and 3), while pseudopod formation was obvious in the cells of the untreated group (FIG. 7A, rows 2 and 3) and the IFN alpha-2b treated group (FIG. 7B, rows 2 and 3). This experiment shows that rSIFN-co not only could suppress the growth of cancer cell colony, but also could inhibit invasive feet formation in the cancer cells, a feature that is necessary for metastasis.

Example 7. Inhibition of Beta-Catenin/TCF Transcriptional Activity by rSIFN-co

Beta-Catenin/TCF Transcription Reporter Assay.
The effect of rSIFN-co on Wnt/Beta-catenin signaling in vitro was determined. Cancer cells were plated in 96-well plates (at $1 \times 10^4$ cells per well), and incubated for 12 hours, after which they were transiently transfected with 100 ng TOPFlash (Millipore Corporation, Billerica, Mass., USA). To normalize transfection efficiency, cells were co-transfected with 1 ng of internal control reporter *Renilla reniformis* luciferase driven under the SV40 promoter, pRL-5V40 (Promega, Madison, Wis., USA), and then treated with 10 mcg/ml interferons, rSIFN-co or IFN alpha-2b, or left untreated as Control (Mock) after transfection for 6 hours. After interferon treatment for 24 hours, luciferase assay was performed using the Dual Luciferase Assay System kit according to the manufacturer's protocols (Cat #: E1960, Promega). Relative luciferase activity was reported as a ratio of firefly/renilla luciferase activity. Experiments were performed in triplicate.

Figure 8:
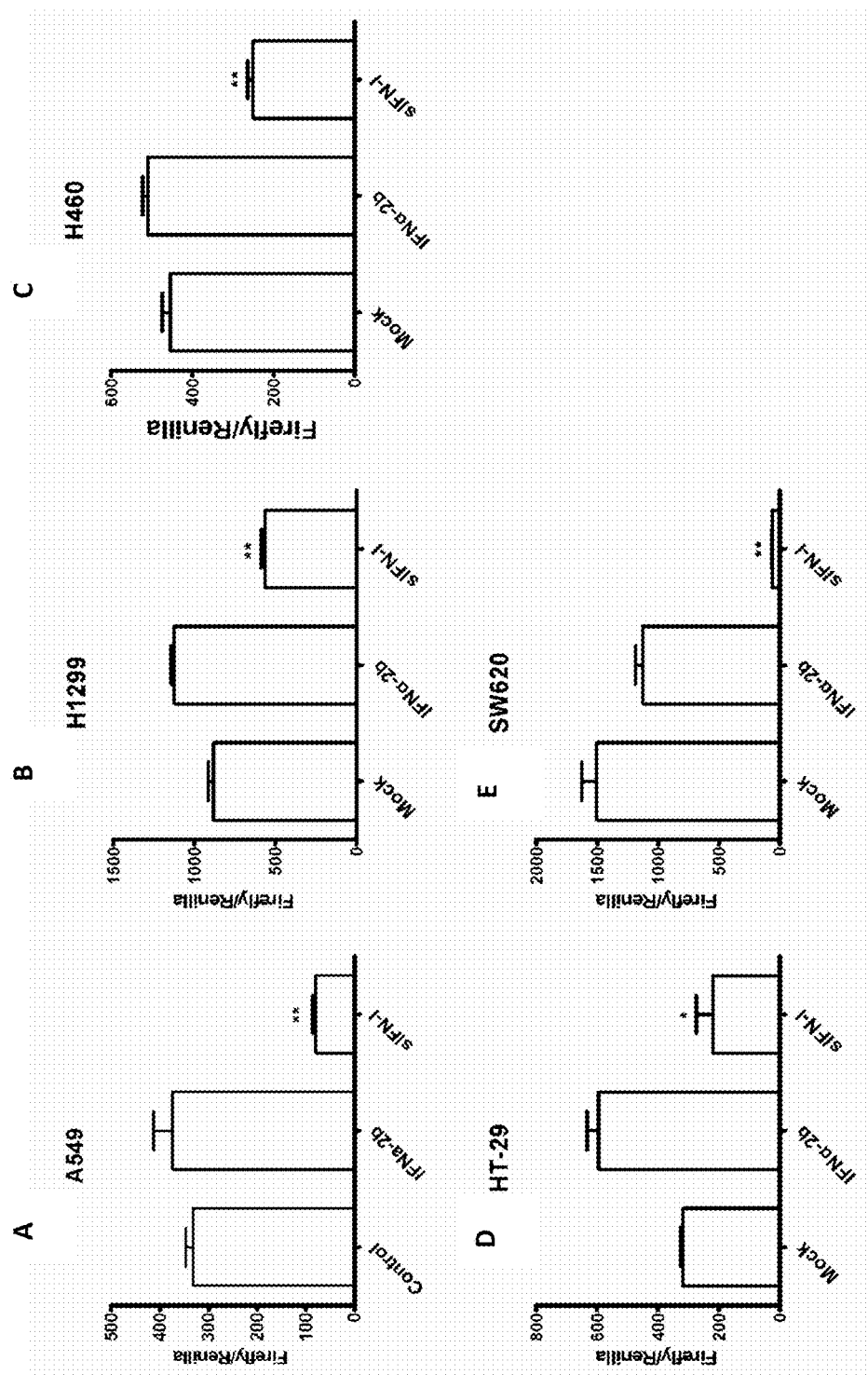
FIG. 8, A-E are bar diagrams showing the effect of rSIFN-co treatment and IFN alpha-2b treatment, respectively, on beta-catenin/TCF-mediated transcriptional activity in different lung cancer cells: A549 (FIG. 8A); H1299 (FIG. 8B); and H460 (FIG. 8C); and different colon cancer cells: HT-29 (FIG. 8D); and SW620 (FIG. 8E) as compared to mock control. Values were averages of 3 experiments. (*$p<0.05$, **$p<0.01$).

Results, shown in FIG. 8, indicated that rSIFN-co decreased beta-catenin/TCF mediated transcriptional activity in human solid cancer cells. After treatment for 24 hours, the beta-catenin/TCF-mediated transcriptional activity was significantly suppressed by rSIFN-co in three lung cancer cells (A549, H1299, H460) and two colon cancer cells (HT-29, SW620) (*, $p<0.05$, **, $p<0.01$). However, the inhibitory effect of IFN alpha-2b was non-existent for A549 cells, H1299 cells, H460 cells and HT-29 cells and had resulted in enhancement, instead of inhibition.

Briefly, the Firefly/Renilla ratios for the Control group, the IFN alpha-2b-treated group and the rSIFN-co-treated groups were, respectively: (A) for the A549 cells: about 310, about 350, and about 100; (B) for the H1299 cells: about 800, about 1000, and about 500; (C) for the H460 cells: about 450, about 500, and about 280; (D) for the HT-29 cells: about 300, about 600, and about 200; (E) for the SW620 cells: about 1500, about 1200, and about less than 100. This study shows that rSIFN-co was superior to IFNα-2b in the suppression of Wnt/TCF signaling and hence, in its antitumor effect.

Example 8. rSIFN-co Decreased Beta-Catenin Protein Level in Cancer Cells

Cancer cells, A549 and Sw480, were cultured to about 85% confluency and put into 6 well plates. The cells were treated with either 10 mcg/ml IFNα-2b or rSIFN-co or left untreated as control (Mock) for 24 hr, 48 hr, or 72 hr, respectively. After treatment, the cells were harvested for Western Blot to detect the beta-catenin protein level, using its specific antibody, with GAPDH as endogenous loading control. The experiment was conducted in triplicate.

Western Blot Analysis.

To determine the expression of various proteins, cells were harvested from the plates and total cellular protein were extracted using extraction reagents (Cat #: P0013) according to the manufacturer's protocol (Beyotime, China). The total protein concentration was determined by the Lowry Protein Assay kit (Bio-Rad, USA). Total proteins were separated by sodium dodecylsulfate-polyacrylamide gel electrophoresis (SDS-PAGE) on 10%-12% gel and transferred to 0.22 or 0.45 μm PVDF membranes (Millipore Corporation, Billerica, Mass., USA). The membranes were blocked with 5% skimmed milk, bovine serum albumin, 10 mmol/L Tris-HCl at pH 8.0, 150 mmol/L NaCl, and 0.05% Tween 20 overnight at 4° C. The blocked membranes were then incubated with primary antibodies (1:1000 dilutions), followed by secondary HRP-conjugated antibodies. Blots were visualized using Luminescence/Fluorescence Imaging LAS4000 System (GE Healthcare Life Sciences, USA) with super signal west pico chemiluminescent substrate kit (Thermo scientific, USA).

Figure 10:
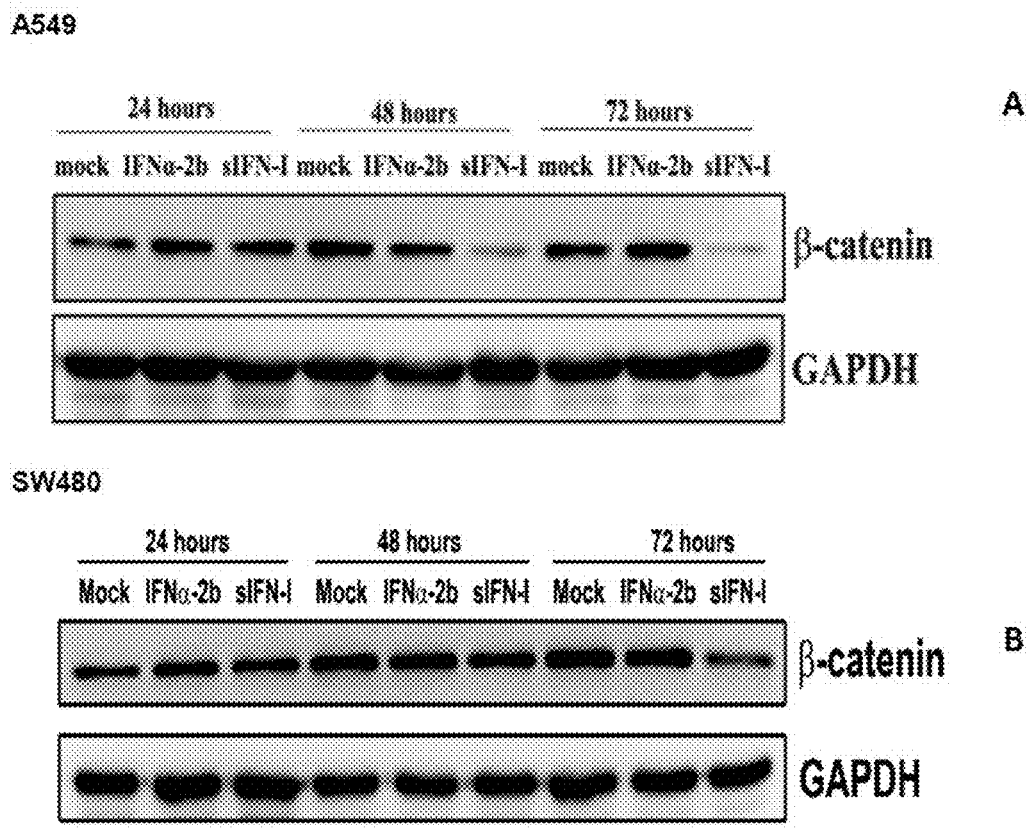
FIGS. 10, A and B, are Western Blots and showing the effect of rSIFN-co treatment and IFN alpha-2b treatment, respectively, as compared to mock control, on beta-catenin protein level in cancer cells: A549 (FIG. 10A) and SW480 (FIG. 10B), after 24, 48 and 72 hr of treatment, respectively. GAPDH expression was used as a control. Experiment was conducted in triplicate.

For this determination, the primary antibodies used were mouse monoclonal anti-beta-catenin antibodies (1:1000; Santa Cruz Technology, Santa Cruz, Calif.) and mouse monoclonal anti-GAPDH antibodies (1:2000) (Kangwei Biotechnology, China). Anti-mouse HRP-conjugated secondary antibodies (Santa Cruz Technology, Santa Cruz, Calif.) were used at concentrations of 1:2000. Results, shown in FIG. 10, demonstrate that as for A549 cells, rSIFN-co dramatically decreased beta-catenin protein level after treatment for 2 days (48 hr). Further decrease was observed, for these cells, after treatment for 3 days (72 hr). Decrease in beta-catenin protein level in the SW480 cells was obvious after 72 hours of treatment with rSIFN-co. Down-regulation of beta-catenin was apparently time dependent in both the lung cancer A549 cells and the colon cancer SW480 cells. In contrast, IFN alpha-2b did not cause any apparent decrease in beta-catenin level, suggesting that it had no effect on the down-regulation of beta-catenin.

Example 9. rSIFN-co Induced Transcriptional Down-Regulation of Wnt Pathway Mediated Target Genes The lung cancer A549 cells were seeded into 6-well plates and treated with 10 μg/ml of either IFN alpha-2b or rSIFN-co, respectively, or were left untreated as control (Mock). After 24 hr of treatment, cellular total mRNA was isolated using TRIZOL Reagent and cDNA was synthesized and further subjected to qPCR, using specific primers of four (4) Wnt signaling downstream genes, Axin2, CD24, Survivin and ID2. Experiments were conducted in triplicate and normalized with the Mock group.

Quantitative PCR (qPCR) Analysis.

Total mRNA was isolated using TRIZOL Reagent (Invitrogen, Carlsbad, Calif.) according to the manufacturer's instructions. Complementary DNA (cDNA) was synthesized using a RT-PCR Kit (Cat #: FSQ-101, TOYOBO, Japan) according to the manufacturer's instructions and then subjected to qPCR with a SYBR Green PCR kit (Cat #: QPK-201, TOYOBO, Japan). The primers of the four Wnt pathway target genes were as follows: Axin2 sense primer: 5'-CGTGGATACCTTAGACTT-3' (SEQ ID NO:8) and antisense primer: 5'-GCTIGTIUTTCTCAATGTA-3' (SEQ ID NO: 9); CD24 sense primer: 5'-TGAAGAACATGT-GAGAGGTTTGAC-3' (SEQ ID NO: 10) andantisense primer: 5'-GAAAACTGAATCTCCATFCCACAA-3' (SEQ ID NO: 11); Survivin sense primer: 5'-ACCGCATCTCFA-CATTCAAG-3' (SEQ ID NO: 12) and antisense primer: 5'-CAAGTCTGGCTCGTTCTC-3' (SEQ ID NO: 13) and ID2 sense primer: 5'-CACAACAACAACAACAAC-3' (SEQ ID NO: 14) and antisense primer: 5'-CACAGTC-CAAGTAAGAGA-3' (SEQ ID NO: 15).

The amplification protocol consisted of incubations at 95° C. for 1 minute, 40 cycles (95° C. for 15 seconds, 60° C. for 15 seconds, 72° C. for 30 seconds). Incorporation of the SYBR Green dye into PCR products was monitored in real time with a Bio-Rad Detection System and subsequently analyzed using Bio-Rad CFX manager 2.1 software. The samples were pooled for each condition and run in duplicate. Treated samples were compared to Mock using the $2^{-\Delta\Delta Ct}$ method and plotted as fold change. GAPDH was used as the normalization control.

Figure 11:
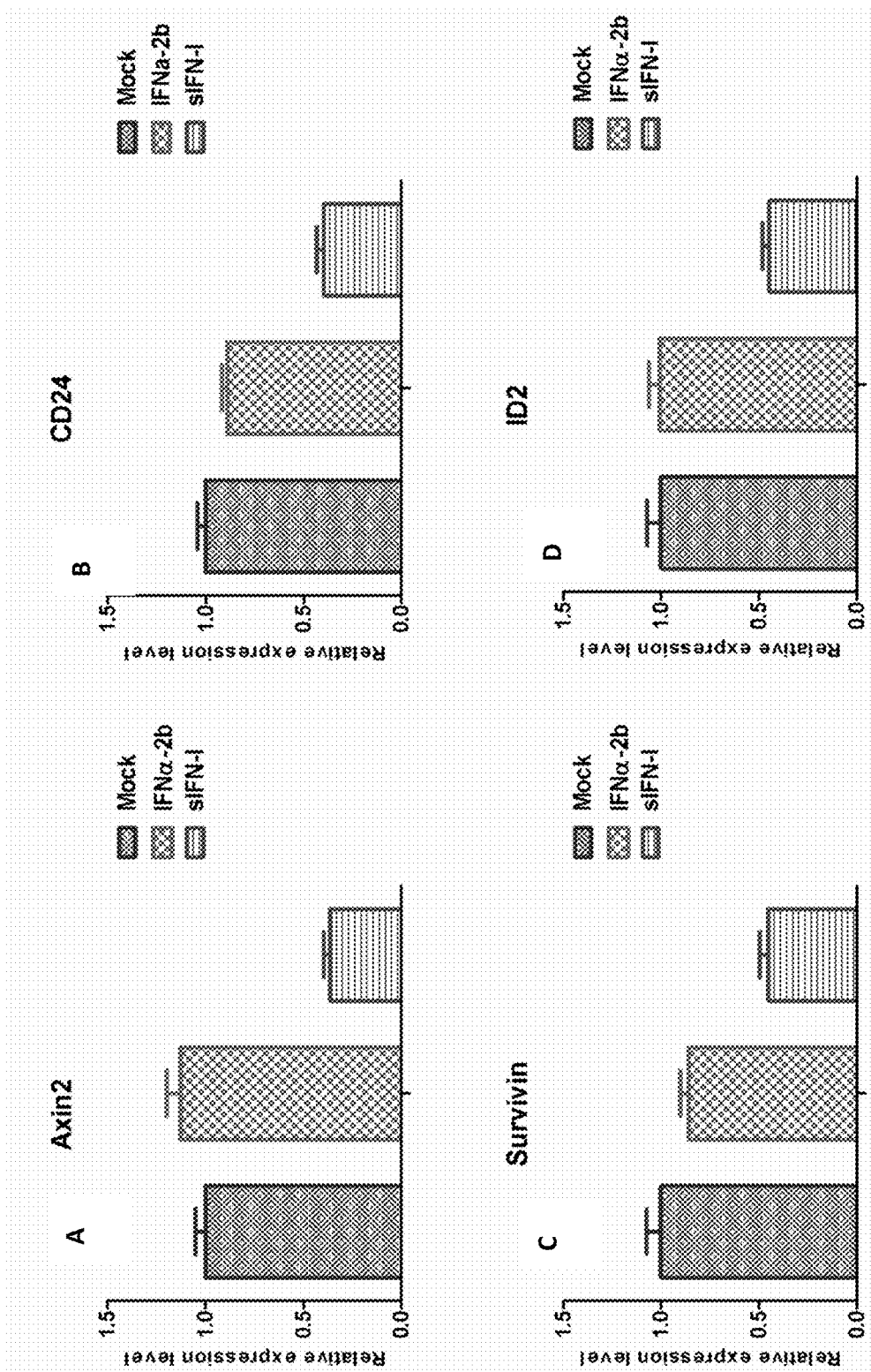
FIG. 11, A-D, are bar diagrams showing the relative mRNA expression level of four (4) genes that are downstream of the Wnt-signaling pathway after A549 lung cancer cells were treated for twenty-four (24) hours with either rSIFN-co or IFN alpha-2b, as compared to mock control: Axin2 (FIG. 11A); CD24 (FIG. 11B); Survivin (FIG. 11C); and ID2 (FIG. 11D). Experiment was conducted in triplicate and normalized with the mock control group.

Results, shown in FIG. 11, demonstrate that rSIFN-co induced down-regulation of Wnt pathway mediated target genes, Axin2, CD24, survivin, and ID2. The mRNA level of these genes were significantly reduced after rSIFN-co treatment but not after interferon IFN alpha-2b treatment.

Briefly, when the relative expression level for the Mock control was set at 1, for the Axin2 gene (FIG. 11A), the IFN alpha-2b treatment resulted in a level of slightly over 1, while rSIFN-co treatment resulted in a level of about 0.4 (p<0.0001, comparing rSIFN-co treatment with no treatment). The corresponding levels for the CD24 gene (FIG. 11B) were 1, about 0.9 and about 0.4 (p<0.0001), respectively; for the Survivin gene (FIG. 11C) were 1, about 0.9, and about 0.4 (p<0.0005), respectively; for the ID2 (FIG. 11D) gene were 1, about 1, and about 0.4 (p<0.0001), respectively, for Mock untreated cells, IFNalpha-2b-treated cells and the rSIFN-co-treated cells, respectively.

Example 10. rSIFN-co Could Down-Regulate Wnt-Related Receptors or Co-Receptors LRP6/FZD6 mRNA Level in Different Cells The regulation of LRP6/FZD6 by rSIFN-co was investigated. This was conducted by qPCR as performed in Example 9. Cancer cells, A549, H460, SW620 and HT-29, were seeded into 6-well plates and treated with 10 µg/ml IFN alpha-2b or rSIFN-co or was left untreated as control (Mock). After 24 hr of treatment, total cellular mRNA was isolated using TRIZOL Reagent, and cDNA was subjected to qPCR using specific primers of LRP6 and FZD6. The primers used were: LRP6 sense primer: 5'-TGAAGAAC-CAGCACCACAGG-3' (SEQ ID NO: 4) and antisense primer: 5'-CATAACCAAGAGGCACAGAAGC-3' (SEQ ID NO: 5), and FZD6 sense primer: 5'-GCGGAGT-GAAGGAAGGATTAGTC-3' (SEQ ID NO: 6) and antisense primer: 5'-TGAACAAGCAGAGATGTGGAACC-3' (SEQ ID NO: 7). Experiments were conducted in triplicate and normalized with the Mock control group. Results were recorded as relative mRNA level of either LRP6 or FZD6 relative to GAPDH.

Figure 9:
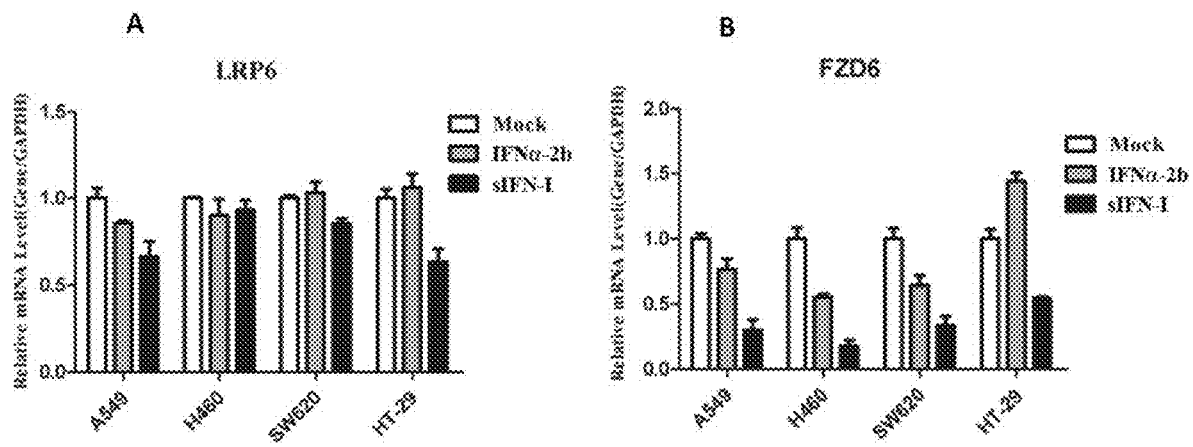
FIGS. 9, A and B, are bar diagrams showing the effect of rSIFN-co treatment and IFN alpha-2b treatment, respectively, as compared to mock control on the expression of Wnt-related receptors or co-receptors, LRP6 (FIG. 9A) and FZD6 (FIG. 9b) in different cancer cells as measured by mRNA levels relative to expression of GAPDH: A549, H460, SW620, and HT-29. Experiment was conducted in triplicate and results were normalized with the mock control group.

Results, shown in FIG. 9, indicated that both LRP6 and FZD6 were down-regulated to various extents by rSIFN-co in the four cancer cell lines. FIG. 9A shows significant reduction in the relative expression of the LRP6 mRNA in the A549 cells (p<0.005), SW620 cells (p<0.005) and the HT-29 cells (p<0.005) after rSIFN-co treatment but no significant reduction was seen with the IFN alpha-2b treatment. FIG. 9B shows significant reduction in relative expression of FZD6 mRNA in all 4 cell lines, A549 (p<0.001), H460 (p<0.0005), SW620 (p<0.001), and HT-29 (p<0.0005) after treatment with rSIFN-co. The other interferon, IFN alpha-2b caused enhancement of FZD6 mRNA expression in HT-29 cells, but induced some reduction in FZD6 mRNA expression, though not to the same extent as rSIFN-co, in A549 cells, H460 cells and SW620 cells. Results indicate that the suppression of Wnt signaling pathway by rSIFN-co might have resulted from the inhibition of expression of the Wnt related cellular surface receptors LRP6 and FZD6. rSIFN-co was found to be superior to interferon IFNα-2b in suppressing the Wnt pathway, in the human cancer cells tested, such as human lung cancer and human colon cancer cells, including the down-regulation of beta-catenin/TCF-mediated transcriptional activity and beta-catenin protein level, as well as Wnt signaling pathway related receptors, co-receptors and target genes.

Example 11. rSIFN-co Up-Regulated the Expression of Tumor Suppressor Genes

The effect of rSIFN-co on the up-regulation of tumor suppressor genes was demonstrated in this study. Cancer cells, A549, H460, SW620 and HT-29, were seeded into 6-well plates and treated with 10 mcg/ml of IFN alpha-2b or rSIFN-co, or were left untreated as Mock control. After 24 hr of treatment, total cellular mRNA was isolated using TRIZOL Reagent, and cDNA was synthesized, and further subjected to qPRC using specific primers for DKK3, KLF4 and BATF2. The following primers were used: for BATF2, sense primers: 5'-CAGAGCAGGGAGCACAAACC-3' (SEQ ID NO: 16) and antisense primers: 5'-TGAGCAGAG-GAGAGCAGAGG-3' (SEQ ID NO: 17); for DKK3, sense primers: 5'-GGAGCCTGACTGAAGAGATGG-3'(SEQ ID NO: 18) and antisense primers: 5'-ACGCCTAAAGCACA-CACCTG-3' (SEQ ID NO: 19); for KLF4, sense primers: 5'-CCTTCAACCTGGCGGACATCAAC-3' (SEQ ID NO: 20) and antisense primers: 5'-GGCTGCTGCGGCG-GAATG-3' (SEQ ID NO: 21).

Figure 12:
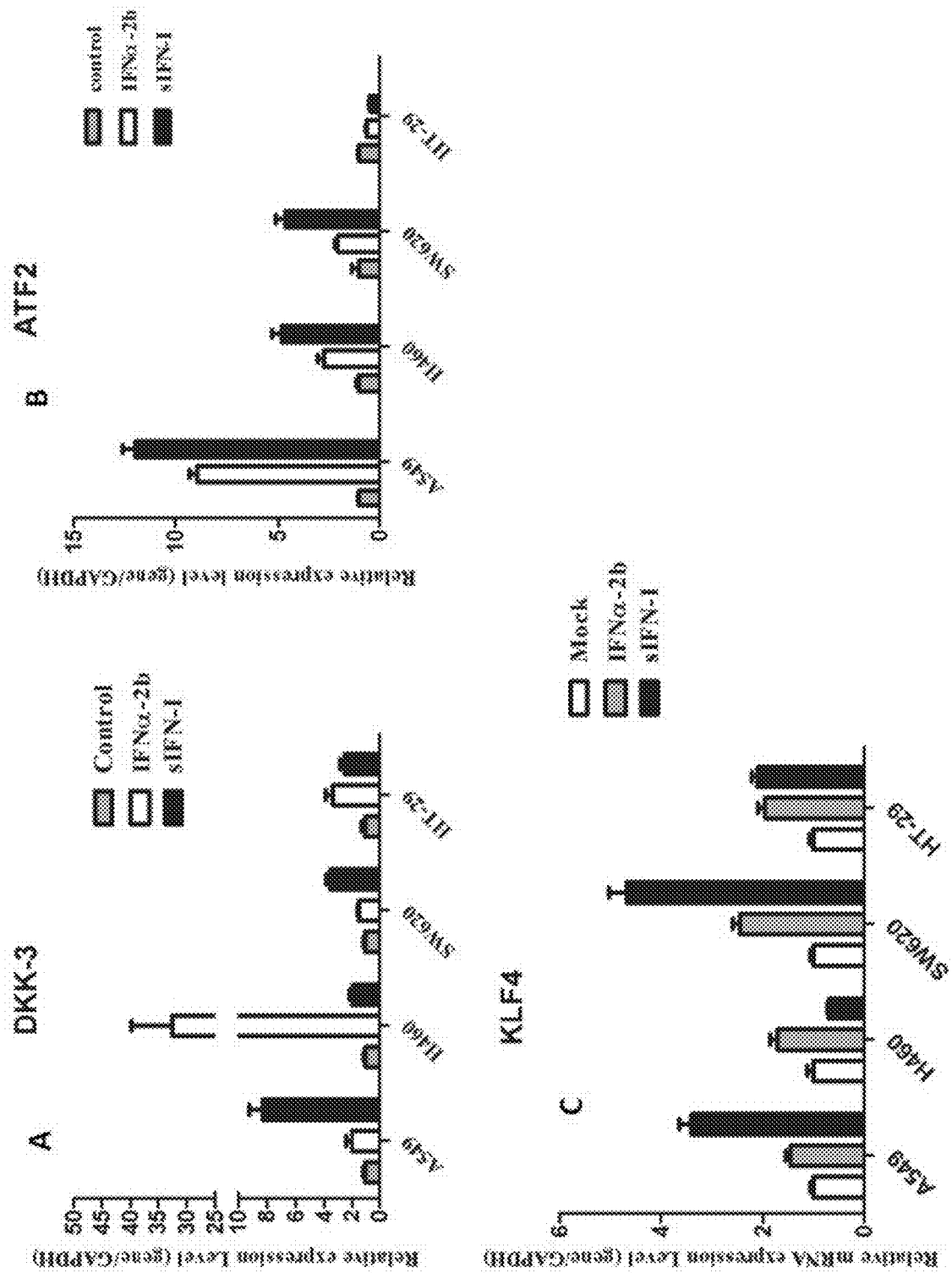
FIG. 12, A-C, are bar diagrams showing the relative mRNA expression level of 3 tumor suppressor genes: DKK-3 (FIG. 12A); BATF2 (FIG. 12B); and KLF4 (FIG. 12C) in different tumor cells: A549, H460, SW620, and HT-29, that were treated with either rSIFN-co or IFN alpha-2b, as compared to mock control. Experiment was conducted in triplicate and normalized with the mock control group.

The experiment was conducted in triplicate and normalized with the mock control group. Results, shown in FIG. 12, were expressed as relative mRNA expression level in relation to that of GAPDH. For the A549 cells, treatment with rSIFN-co dramatically increased the expression of all 3 tumor suppressor genes, DKK-3 (FIG. 12A), BATF2 (FIG. 12B), and KLF4 (FIG. 12C) and was much more effective than IFN alpha-2b. In SW620 cells, up-regulation of KLF4 expression after rSIFN-co treatment was also dramatically increased as compared to control and IFN alpha-2b treatment. IFN alpha-2b treatment dramatically enhanced DKK-3 expression in H460 cells.

Example 12. rSIFN-co Inhibited Cancer Cell Migration

The ability of rSIFN-co to suppress tumor cell migration was demonstrated by determining the ability of lung cancer A549 cells and colon cancer SW620 cells to migrate across microporous membranes after treatment with IFN alpha-2b or rSIFN-co for 24 hr, as compared to untreated control (Mock). The cell migration assay was performed using 8 µm cell culture inserts in 24-well plates (Becton-Dickinson Biosciences, NJ, USA). Warm (37° C.) bicarbonate based culture medium without FBS was added to the interior of the inserts and to the bottoms of the wells, and were allowed to rehydrate for 2 hr in humidified tissue culture incubator at 37° C. in 5% $CO_2$. After rehydration, the culture medium was carefully removed. Subsequently, the 500 µl of prepared cells (after treatment with either 10 µg/ml of IFN alpha-2b or 10 µg/ml of rSIFN-co, or not having been treated at all) suspended in FBS-free medium were seeded onto the upper part of the insert filters at a density of $0.5 \times 10^4$ cells/insert. In the lower compartment of the 24-well plates were placed 500 µl of complete medium with 10% FBS. After 24 hr at 37° C. under the regular culture conditions, the non-migrated cells in the upper part of the chamber membranes were removed with a cotton swab. The lower part of the culture inserts were fixed with 4% paraformaldehyde and stained with 2% crystal violet. The number of migrated cells on the opposite side of the chamber membranes from where the cells were placed was counted in each of the triplicate wells. Each experiment was repeated at least two times, each time with triplicate wells.

Figure 13:
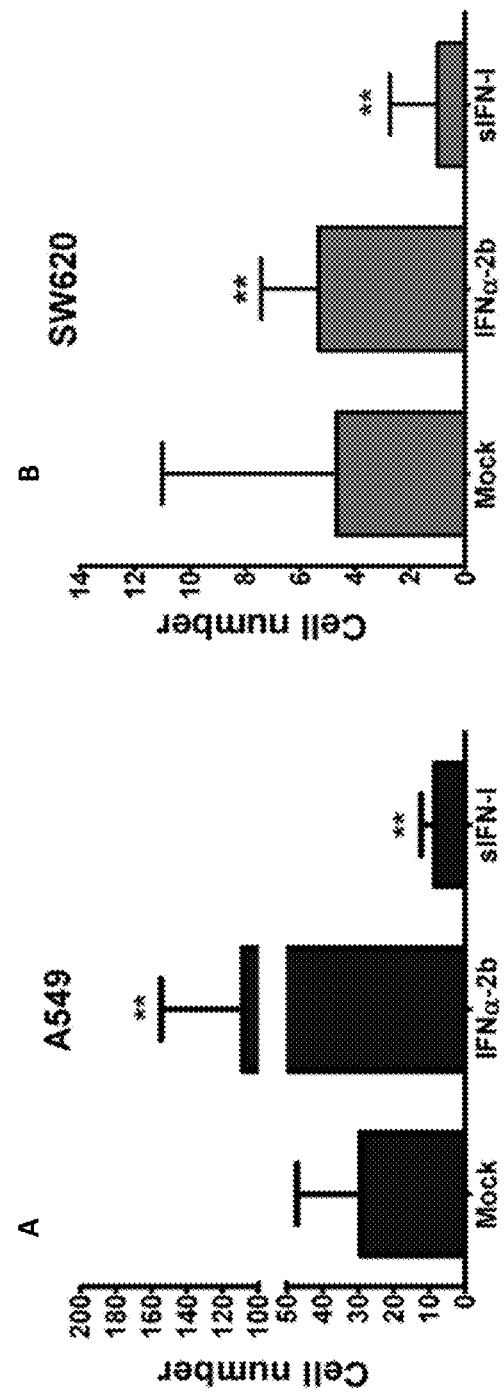
FIGS. 13, A and B, are bar diagrams showing the tumor cell migration after treatment with either IFN alpha-2b or rSIFN-co as compared to Mock controls, for A549 cells (FIG. 13A) and SW620 cells (FIG. 13B). Results are presented as the mean number of migrating cells per field SD after such treatment. (**p<0.01)

Results, shown in FIG. 13, showed the mean number of migrating cells per field for each of the Mock, IFN alpha-2b-treated cells, and rSIFN-co-treated cells. For the A549 cells that had migrated across the membrane, about 30 cells per field were observed in the untreated Mock group, about 110 cells were seen in the IFN alpha-2b group, and about 10 cells were seen in the rSIFN-co-treated group. The enhancement of migration caused by IFN alpha-2b treatment and the inhibition of migration caused by the rSIFN-co treatment were statistically significant (p<0.01). Significant inhibition by rSIFN-co was also observed with SW620 cells. In contrast, IFN alpha-2b treatment resulted in enhancement of tumor cell migration in SW620 cells. Hence, rSIFN-co was effective inhibiting tumor cell migration, and was much more effective than IFN alpha-2b.

Example 13. rSIFN-co Did Not Exert its Effect Through the Apopotosis Pathway

This study was performed to show that rSIFN-co exerted its effect on reducing the viability of tumor cells by other than the apoptotic pathway. Tumor cells A549 and SW620, were plated into 6-well plates, incubated overnight and then treated with either 10 mcg/ml of IFN alpha-2b, or 10 mcg/ml of rSIFN-co or with 5FU or were left untreated (as Mock control) for 24 hr or 48 hr. Thereafter, apoptosis-related molecular markers were monitored by Western Blot. The primary antibodies used were mouse monoclonal anti-beta-tubulin (1:2000, Cat #: CW0098A) and mouse monoclonal anti-GAPDH (1:2000, Cat #: CW0100A) (Kangwei Biotechnology, China); mouse monoclonal anti-PARP (1:1000, Cat #: se-2007, Santa Cruz Biotechnology, Inc.); rabbit monoclonal anti-procaspase 3 (1:1000, Cat #: 9665), and rabbit polyclonal anti-cleaved caspase 3 (1:1000, Cat #: 9661) (Cell Signaling Technology, USA); goat polyclonal anti-procaspase 8 (1:1000, Cat #: sc-6136, Santa Cruz Biotechnology, Inc); rabbit monoclonal anti-cleaved caspase 8 (1:1000, Cat #: 9496) (Cell Signaling Technology, USA).

Figure 14:
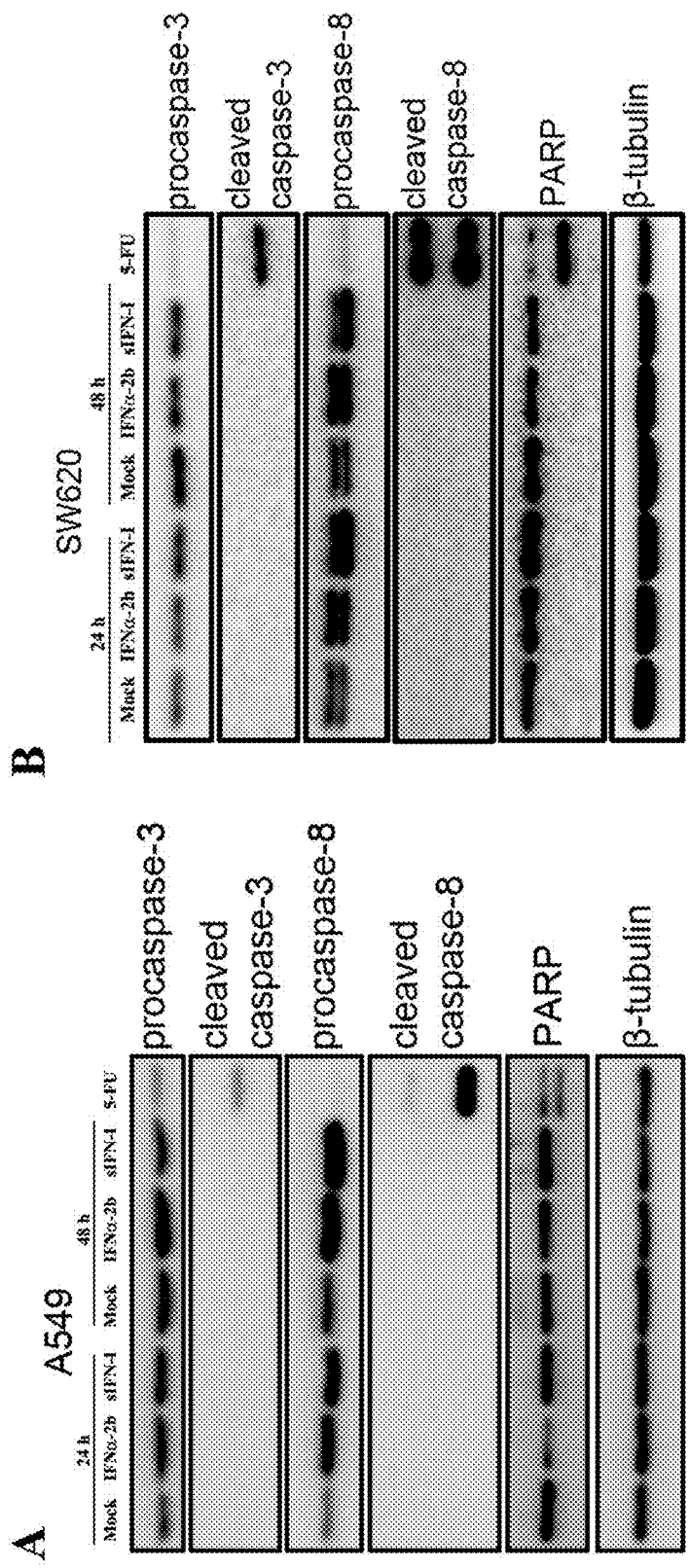
FIG. 14 are Western Blots, stained with specific antibodies to procaspase-3, cleaved caspase-3, procaspase-8, cleaved caspase-8, PARP, and beta-tubulin (β-tubulin), from A549 cells (FIG. 14A) and SW620 cells (FIG. 14B) after they were treated with either IFN alpha-2b or rSIFN-co for 24 hr or 48 hr as compared to Mock controls and 5FU-treated cells, respectively.

Results are shown in FIG. 14A, for A549 cells and FIG. 14B for SW620 cells. The Western Blots showed that after treatment with 5FU, a drug known to cause apoptosis, the cells exhibited a significant reduction of in the level of procaspase-3, procaspase-8 and PARP, but exhibited an enhanced level of cleaved caspase-3 and cleaved caspase-8. In contrast, neither of the interferons, IFN alpha-2b nor rSIFN-co, caused any reduction in the level of procaspase-3 or procaspase-8 or PARP, or induced any enhancement in the level of cleaved caspase-3 or cleaved caspase-8. Thus, results indicated that the two interferons, especially rSIFN-co, likely caused reduction in tumor cell viability by a different mechanism than through apoptosis.

Example 14. rSIFN-co Induced STAT Phosphorylation

This experiment was conducted to show that rSIFN-co utilized the JAK/STAT signaling pathway just as IFN alpha-2b. In this study, A549 cells and Hela cells were each plated into 3.3 cm dishes, incubated at 37° C. overnight, and then treated with 10 μg/ml of either IFN alpha-2b or rSIFN-co for 0, 5, 15, 30, 60, 120 and 240 minutes respectively. After treatment, the cells were collected, cellular proteins were extracted and loaded onto SDS-PAGE agarose for Western Blot analysis to observe the phosphorylation of STAT1 (Tyr701), STAT2 (Tyr690), and STAT3(Tyr705). GAPDH was used as a loading control.

The primary antibodies used were: STAT1 (1:1000, Cat #: 9175S), Tyr701 phosphorylated-STAT1 (1:1000, Cat #: 9167S), STAT2 (1:500, Cat #4594), Tyr690 phosphorylated-STAT2 (1:1000, Cat #: 441S), STAT3 (1:1000, Cat #: 9132), Tyr705 phosphorylated-STAT3 (1:1000, Cat #: 9145S). Anti-mouse (Cat #: sc-2005) or rabbit (Cat #: sc-2004) or goat (Cat #: sc-2020) HRP-conjugated secondary antibodies (Santa Cruz Technology, Santa Cruz, Calif.) were used at concentrations of 1:2000. Blots were visualized by use of Luminescence/Fluorescence Imaging LAS4000 System (GE Healthcare Life Sciences, USA) with super signal west pico chemiluminescnet substrate kit (Thermo Scientific, USA).

Figure 15:
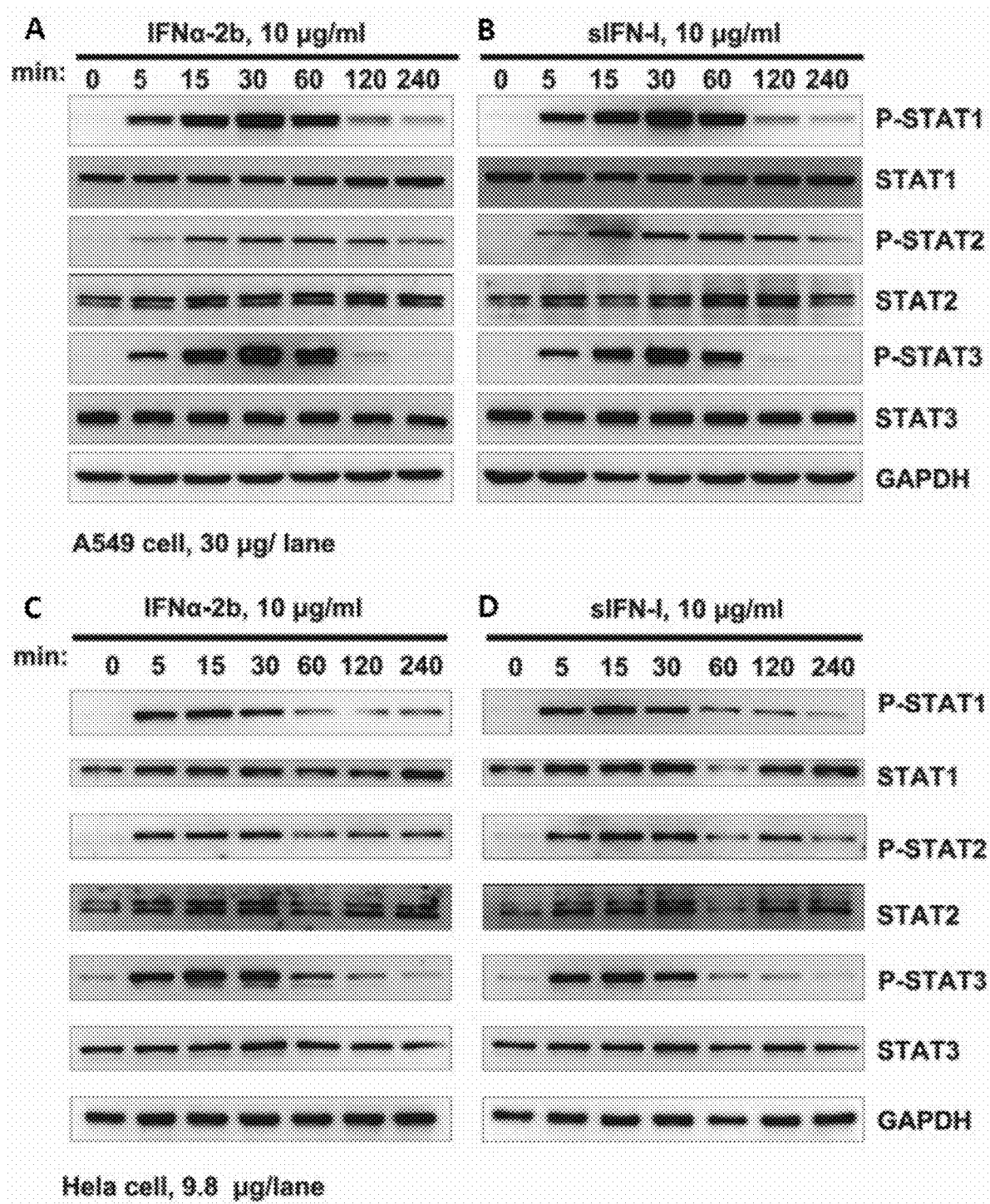
FIG. 15 are Western Blots, stained with specific antibodies to P-STAT1, STAT1, P-STAT2, STAT2, P-STAT3, STAT3 and GAPDH, after A549 cells were treated with IFN alpha-2b (FIG. 15A) at 10 mcg/ml, or rSIFN-co (FIG. 15B) at 10 mcg/ml, or after Hela cells were treated with IFN alpha-2b (FIG. 15C) at 10 mcg/ml, or rSIFN-co (FIG. 15D) at 10 mcg/ml.

Results, shown in FIG. 15, demonstrate that the 2 interferons, IFN alpha-2b and rSIFN-co behaved similarly in their phosphorylation patterns for STAT1, STAT2 and STAT3 in both A549 cells and Hela cells. Hence, rSIFN-co-mediated JAK/STATs signaling level was no different from that mediated by IFN alpha-2b, suggesting that rSIFN-co and IFN alpha-2b may share the common IFNAR1/2 receptors.

INDUSTRIAL APPLICABILITY

The methods and assay kits described herein are useful for determining the potency of a test compound, such as an interferon, and for treatment of certain diseases or conditions which are negatively affected by over-activity or over-expression of beta-catenin, or any one or more of LRP6, FZD6, Axin2, CD24, Survivin, and ID2 or by down-regulation of DKK3, BATF2 or KLF4.

What is claimed is:

1. A method of determining or comparing potency of a test interferon relative to super interferon (rSIFN-co), or establishing substantial equivalence between a test interferon and rSIFN-co, comprising the steps of:
   1) providing a first sample, a second sample and a third sample of cancer cells of the same type;
   2) treating the first sample with the test interferon, treating the second sample with rSIFN-co, and using the third sample as a control sample;
   3) measuring expression level of lipoprotein receptor-related protein 6 (LRP6) and/or Frizzled family receptor 6 (FZD6) in the first, second and third samples; wherein statistically significant down-regulation of expression of LRP6 and/or FZD6 in the first sample and the second sample compared to the control sample indicates substantial equivalence between the test interferon and rSIFN-co and/or that the test interferon and rSIFN-co have substantially the same potency.

2. The method of claim 1, wherein the cancer cells comprise one or more of: lung cancer cells, colon cancer cells, cervical cancer cells, liver cancer cells, breast cancer cells, and pancreatic cancer cells.

3. The method of claim 1, wherein the cancer cells comprise HT-29 cells.

4. The method of claim 1, wherein said statistically significant down-regulation exists when a p value between the control sample and the first sample and/or a p-value between the control sample and the second.

5. The method of claim 1, wherein the control sample is not treated with the test interferon or rSIFN-co, or is treated with normal saline or phosphate-buffered saline, or is treated with IFNα-2b, or is untreated.

6. The method of claim 1, wherein the amino acid sequence of the test interferon is at least 90%, identical to SEQ ID NO: 1.

7. The method of claim 1, wherein the nucleotide sequence encoding the test interferon is at least 90%, identical to SEQ ID NO: 2.

8. The method of claim 1, wherein the test interferon and rSIFN-co have the same amino acid sequence of SEQ ID NO: 1, and are encoded by the same nucleotide sequence of SEQ ID NO: 2.

9. The method of claim 1, wherein the test interferon and rSIFN-co have substantially the same specific activity.

10. The method of claim 9, wherein the specific activity is in the range of about $4\times10^8$ IU/mg to about $1\times10^9$ IU/mg.

11. The method of claim 1, wherein the step of measuring expression level of lipoprotein receptor-related protein 6 (LRP6) and/or Frizzled family receptor 6 (FZD6) comprises measuring messenger RNA level of LRP6 and/or FZD6.

* * * * *

UNITED STATES PATENT AND TRADEMARK OFFICE
CERTIFICATE OF CORRECTION

PATENT NO. : 10,677,782 B2
APPLICATION NO. : 15/035749
DATED : June 9, 2020
INVENTOR(S) : Guangwen Wei It is certified that error appears in the above-identified patent and that said Letters Patent is hereby corrected as shown below:

On the Title Page

Item (71), delete "Guangwen Wei, Chengdu (CN);".

Line 1, reference under OTHER PUBLICATIONS, please replace "Wht" with --Wnt--.

In the Claims

In Column 54, Claim 4, Line 63, replace "p value" with --p-value--, and Line 65, replace "the second" with --the second sample is 0.05 or less--.

Signed and Sealed this
Eleventh Day of August, 2020

Andrei Iancu
*Director of the United States Patent and Trademark Office*

SEQUENCE LISTING

```
<160> NUMBER OF SEQ ID NOS: 21

<210> SEQ ID NO 1
<211> LENGTH: 167
<212> TYPE: PRT
<213> ORGANISM: Artificial Sequence
<220> FEATURE:
<223> OTHER INFORMATION: Amino acid sequence of recombinant interferon

<400> SEQUENCE: 1

Met Cys Asp Leu Pro Gln Thr His Ser Leu Gly Asn Arg Arg Ala Leu
1               5                   10                  15

Ile Leu Leu Ala Gln Met Arg Arg Ile Ser Pro Phe Ser Cys Leu Lys
            20                  25                  30

Asp Arg His Asp Phe Gly Phe Pro Gln Glu Glu Phe Asp Gly Asn Gln
        35                  40                  45

Phe Gln Lys Ala Gln Ala Ile Ser Val Leu His Glu Met Ile Gln Gln
    50                  55                  60
```

Thr Phe Asn Leu Phe Ser Thr Lys Asp Ser Ser Ala Ala Trp Asp Glu
65                  70                  75                  80

Ser Leu Leu Glu Lys Phe Tyr Thr Glu Leu Tyr Gln Gln Leu Asn Asp
                85                  90                  95

Leu Glu Ala Cys Val Ile Gln Glu Val Gly Val Glu Thr Pro Leu
            100                 105                 110

Met Asn Val Asp Ser Ile Leu Ala Val Lys Lys Tyr Phe Gln Arg Ile
            115                 120                 125

Thr Leu Tyr Leu Thr Glu Lys Lys Tyr Ser Pro Cys Ala Trp Glu Val
        130                 135                 140

Val Arg Ala Glu Ile Met Arg Ser Phe Ser Leu Ser Thr Asn Leu Gln
145                 150                 155                 160

Glu Arg Leu Arg Arg Lys Glu
                165

<210> SEQ ID NO 2
<211> LENGTH: 504
<212> TYPE: DNA
<213> ORGANISM: Artificial Sequence
<220> FEATURE:
<223> OTHER INFORMATION: Nucleotide sequence encoding recombinant
      interferon

<400> SEQUENCE: 2
atgtgcgacc tgccgcagac ccactccctg ggtaaccgtc gtgctctgat cctgctggct    60
cagatgcgtc gtatctcccc gttctcctgc ctgaaagacc gtcacgactt cggtttcccg   120
caggaagaat tcgacggtaa ccagttccag aaagctcagg ctatctccgt tctgcacgaa   180
atgatccagc agaccttcaa cctgttctcc accaaagact cctccgctgc ttgggacgaa   240
tccctgctgg aaaaattcta caccgaactg taccagcagc tgaacgacct ggaagcttgc   300
gttatccagg aagttggtgt tgaagaaacc ccgctgatga cgttgactc catcctggct   360 gttaaaaaat acttccagcg tatcaccctg tacctgaccg aaaaaaaata ctccccgtgc   420
gcttgggaag ttgttcgtgc tgaaatcatg cgttccttct ccctgtccac caacctgcag   480
gaacgtctgc gtcgtaaaga ataa                                         504

<210> SEQ ID NO 3
<211> LENGTH: 504
<212> TYPE: DNA
<213> ORGANISM: Artificial Sequence
<220> FEATURE:
<223> OTHER INFORMATION: Nucleotide sequence encoding recombinant
      interferon

<400> SEQUENCE: 3
tacacgctgg acggcgtctg ggtgagggac ccattggcag cacgagacta ggacgaccga    60
gtctacgcag catagagggg caagaggacg gactttctgg cagtgctgaa gccaaagggc   120
gtccttctta agctgccatt ggtcaaggtc tttcgagtcc gatagaggca agacgtgctt   180
tactaggtcg tctggaagtt ggacaagagg tggtttctga ggaggcgacg aaccctgctt   240
agggacgacc tttttaagat gtggcttgac atggtcgtcg acttgctgga ccttcgaacg   300
caataggtcc ttcaaccaca acttctttgg ggcgactact tgcaactgag gtaggaccga   360 caattttta tgaaggtcgc atagtgggac atggactggc ttttttttat gagggcacg    420 cgaaccctc aacaagcacg actttagtac gcaaggaaga gggacaggtg gttggacgtc   480
cttgcagacg cagcatttct tatt                                         504

```
<210> SEQ ID NO 4
<211> LENGTH: 20
<212> TYPE: DNA
<213> ORGANISM: Artificial Sequence
<220> FEATURE:
<223> OTHER INFORMATION: Sense primer

<400> SEQUENCE: 4
tgaagaacca gcaccacagg                                              20

<210> SEQ ID NO 5
<211> LENGTH: 22
<212> TYPE: DNA
<213> ORGANISM: Artificial Sequence
<220> FEATURE:
<223> OTHER INFORMATION: Antisense primer

<400> SEQUENCE: 5
cataaccaag aggcacagaa gc                                           22

<210> SEQ ID NO 6
<211> LENGTH: 23
<212> TYPE: DNA
<213> ORGANISM: Artificial Sequence
<220> FEATURE:
<223> OTHER INFORMATION: Sense primer

<400> SEQUENCE: 6
gcggagtgaa ggaaggatta gtc                                          23

<210> SEQ ID NO 7
<211> LENGTH: 23
<212> TYPE: DNA
<213> ORGANISM: Artificial Sequence
<220> FEATURE:
<223> OTHER INFORMATION: Antisense primer

<400> SEQUENCE: 7
tgaacaagca gagatgtgga acc                                          23

<210> SEQ ID NO 8
<211> LENGTH: 18
<212> TYPE: DNA
<213> ORGANISM: Artificial Sequence
<220> FEATURE:
<223> OTHER INFORMATION: Sense primer

<400> SEQUENCE: 8
cgtggatacc ttagactt                                                18

<210> SEQ ID NO 9
<211> LENGTH: 18
<212> TYPE: DNA
<213> ORGANISM: Artificial Sequence
<220> FEATURE:
<223> OTHER INFORMATION: Antisense primer

<400> SEQUENCE: 9
gctgttgttc tcaatgta                                                18

<210> SEQ ID NO 10
<211> LENGTH: 24
<212> TYPE: DNA
<213> ORGANISM: Artificial Sequence
<220> FEATURE:
```

```
<223> OTHER INFORMATION: Sense primer

<400> SEQUENCE: 10
tgaagaacat gtgagaggtt tgac                                          24

<210> SEQ ID NO 11
<211> LENGTH: 24
<212> TYPE: DNA
<213> ORGANISM: Artificial Sequence
<220> FEATURE:
<223> OTHER INFORMATION: Antisense primer

<400> SEQUENCE: 11
gaaaactgaa tctccattcc acaa                                          24

<210> SEQ ID NO 12
<211> LENGTH: 20
<212> TYPE: DNA
<213> ORGANISM: Artificial Sequence
<220> FEATURE:
<223> OTHER INFORMATION: Sense primer

<400> SEQUENCE: 12
accgcatctc tacattcaag                                               20

<210> SEQ ID NO 13
<211> LENGTH: 18
<212> TYPE: DNA
<213> ORGANISM: Artificial Sequence
<220> FEATURE:
<223> OTHER INFORMATION: Antisense primer

<400> SEQUENCE: 13
caagtctggc tcgttctc                                                 18

<210> SEQ ID NO 14
<211> LENGTH: 18
<212> TYPE: DNA
<213> ORGANISM: Artificial Sequence
<220> FEATURE:
<223> OTHER INFORMATION: Sense primer

<400> SEQUENCE: 14
cacaacaaca acaacaac                                                 18

<210> SEQ ID NO 15
<211> LENGTH: 18
<212> TYPE: DNA
<213> ORGANISM: Artificial Sequence
<220> FEATURE:
<223> OTHER INFORMATION: Antisense primer

<400> SEQUENCE: 15
cacagtccaa gtaagaga                                                 18

<210> SEQ ID NO 16
<211> LENGTH: 20
<212> TYPE: DNA
<213> ORGANISM: Artificial Sequence
<220> FEATURE:
<223> OTHER INFORMATION: Sense primer

<400> SEQUENCE: 16
cagagcaggg agcacaaacc                                               20
```

```
<210> SEQ ID NO 17
<211> LENGTH: 20
<212> TYPE: DNA
<213> ORGANISM: Artificial Sequence
<220> FEATURE:
<223> OTHER INFORMATION: Antisense primer

<400> SEQUENCE: 17
tgagcagagg agagcagagg                                               20

<210> SEQ ID NO 18
<211> LENGTH: 21
<212> TYPE: DNA
<213> ORGANISM: Artificial Sequence
<220> FEATURE:
<223> OTHER INFORMATION: Sense primer

<400> SEQUENCE: 18
ggagcctgac tgaagagatg g                                             21

<210> SEQ ID NO 19
<211> LENGTH: 20
<212> TYPE: DNA
<213> ORGANISM: Artificial Sequence
<220> FEATURE:
<223> OTHER INFORMATION: Antisense primer

<400> SEQUENCE: 19
acgcctaaag cacacacctg                                               20

<210> SEQ ID NO 20
<211> LENGTH: 23
<212> TYPE: DNA
<213> ORGANISM: Artificial Sequence
<220> FEATURE:
<223> OTHER INFORMATION: Sense primer

<400> SEQUENCE: 20
ccttcaacct ggcggacatc aac                                           23

<210> SEQ ID NO 21
<211> LENGTH: 18
<212> TYPE: DNA
<213> ORGANISM: Artificial Sequence
<220> FEATURE:
<223> OTHER INFORMATION: Antisense primer

<400> SEQUENCE: 21
ggctgctgcg gcggaatg                                                 18
```